United States Patent
Kaneko et al.

(10) Patent No.: US 10,240,141 B2
(45) Date of Patent: Mar. 26, 2019

(54) BIOCATALYST SOLVENT USING IONIC LIQUID, AND BIOCATALYST SOLUTION CONTAINING BIOCATALYST AND SAID SOLVENT

(71) Applicant: MIYOSHI OIL & FAT CO., LTD., Tokyo (JP)

(72) Inventors: Kotaro Kaneko, Tokyo (JP); Nobuhiro Kaneko, Tokyo (JP); Koji Kawai, Tokyo (JP)

(73) Assignee: MIYOSHI OIL & FAT CO., LTD., Tokyo (JP)

( * ) Notice: Subject to any disclaimer, the term of this patent is extended or adjusted under 35 U.S.C. 154(b) by 194 days.

(21) Appl. No.: 15/302,179

(22) PCT Filed: Apr. 10, 2015

(86) PCT No.: PCT/JP2015/061281
§ 371 (c)(1),
(2) Date: Oct. 6, 2016

(87) PCT Pub. No.: WO2015/156398
PCT Pub. Date: Oct. 15, 2015

(65) Prior Publication Data
US 2017/0029801 A1    Feb. 2, 2017

(30) Foreign Application Priority Data

Apr. 10, 2014  (JP) ................... 2014-081483
Aug. 19, 2014  (JP) ................... 2014-166930

(51) Int. Cl.
| | | |
|---|---|---|
| C12N 9/96 | (2006.01) |
| C07C 215/08 | (2006.01) |
| C07C 215/10 | (2006.01) |
| C07C 229/12 | (2006.01) |
| C07C 215/12 | (2006.01) |
| C07C 215/40 | (2006.01) |

(52) U.S. Cl.
CPC .............. *C12N 9/96* (2013.01); *C07C 215/08* (2013.01); *C07C 215/10* (2013.01); *C07C 229/12* (2013.01); *C07C 215/12* (2013.01); *C07C 215/40* (2013.01)

(58) Field of Classification Search
CPC ... C07C 215/08; C07C 215/10; C07C 215/12; C07C 215/40; C07C 229/12; C12N 9/96
See application file for complete search history.

(56) References Cited

FOREIGN PATENT DOCUMENTS

| | | |
|---|---|---|
| EP | 1 995 305 | 11/2008 |
| JP | 6-70798 | 3/1994 |
| JP | 8-187095 | 7/1996 |
| JP | 2005-270007 | 10/2005 |
| JP | 2006-514832 | 5/2006 |
| JP | 2011-137807 | 7/2011 |
| JP | 2012-12313 | 1/2012 |
| JP | 2012-31137 | 2/2012 |
| JP | 2014-131974 | 7/2014 |
| JP | 2014-131975 | 7/2014 |

OTHER PUBLICATIONS

International Search Report dated Jul. 14, 2015 in International Application No. PCT/JP2015/061281.
João V. Rodrigues et al., "Protein stability in an ionic liquid milieu: on the use of differential scanning fluorimetry", Physical Chemistry Chemical Physics, 2011, 13(30), 13614-13616.
Vincerzo F. Curto, et al., "Probing the specific ion effects of biocompatible hydrated choline ionic liquids on lactate oxidase biofunctionality in sensor applications", Physical Chemistry Chemical Physics, 2014, 16(5), 1841-1849.
Christiane Wuensch et al., "Pushing the equilibrium of regio-complementary carboxylation of phenols and hydroxystyrene derivatives" Journal of Biotechnology 2013 168(3), 264-270.
B.L.A. Prabhavathi Devi et al., "Characterization of Ionic Liquid-Based Biocatalytic Two-Phase Reaction System for Production of Biodiesel", AIChE Journal, 2011, 57(6), 1628-1637.
Christina Kohlmann et al., "Ionic liquid facilitates biocatalytic conversion of hardly water soluble ketones", Journal of Molecular Catalysis B: Enzymatic, 2011, 68(2), 147-153.

(Continued)

Primary Examiner — Satyendra K Singh
(74) Attorney, Agent, or Firm — Wenderoth, Lind & Ponack, L.L.P.

(57) ABSTRACT

There is provided a biocatalyst solvent which is capable of dissolving a biocatalyst in a liquid state while maintaining the activity of the biocatalyst at a high concentration from a low temperature to a high temperature, and is capable of storing the biocatalyst for a long time period; and a biocatalyst solution using the biocatalyst solvent. Disclosed is a biocatalyst solvent which consists of an ionic liquid including a quaternary ammonium cation represented by the following Formula (I) and an anion:

[Chemical Formula 1]

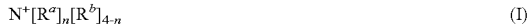

$$N^+[R^a]_n[R^b]_{4-n} \quad (I)$$

wherein $R^a$'s each independently represent a hydroxyalkyl group having one or more hydroxyl groups and an a linear or branched alkyl moiety having 1 to 10 carbon atoms, in which the alkyl moiety may contain an oxygen atom; a carboxyalkyl group having one or more carboxyl groups and a linear or branched alkyl moiety having 1 to 10 carbon atoms, in which the alkyl moiety may contain an oxygen atom; or a hydroxycarboxyalkyl group having one or more hydroxyl groups, one or more carboxyl groups and a linear or branched alkyl moiety having 1 to 10 carbon atoms, in which the alkyl moiety may contain an oxygen atom; $R^b$'s each independently represent a hydrogen atom, or a linear or branched alkyl group having 1 to 5 carbon atoms; and n represents an integer from 1 to 4.

7 Claims, No Drawings

(56) References Cited

OTHER PUBLICATIONS

Cristina Rodriquez, et al., "Ionic liquids for enhancing the enantioselectivity of isolated BVMO-catalysed oxidations", Green Chemistry, 2010 12(12), 2255-2260.

Numo M.T. Lourenco et al., "Ionic Acylating Agents for the Enzymatic Resolution of sec-Alchohols in Ionic Liquids", European Journal of Organic Chemistry, 2010, (36), 6938-6943.

Ranyere Lucena de Souza et al., "Protic ionic liquid as additive on lipase immobilization using silica sol-gel", Enzyme and Microbial Technology, 2013, 52(3), 141-150.

BIOCATALYST SOLVENT USING IONIC LIQUID, AND BIOCATALYST SOLUTION CONTAINING BIOCATALYST AND SAID SOLVENT

TECHNICAL FIELD

The present invention relates to a biocatalyst solvent that can dissolve a biocatalyst in a state of retaining the biocatalytic activity, and a biocatalyst solution containing the solvent and a biocatalyst.

BACKGROUND ART

Many of biocatalysts such as enzymes and yeasts are prone to undergo destruction of the molecular conformation and deterioration of the activity, that is, catalytic ability, under the influence of temperature, pH, solvent, or intermolecular electrostatic repulsion. Therefore, when a biocatalyst is stored or utilized in a biocatalytic reaction, it is necessary to maintain the conformation of an active site and the conformation of amino acid residues. Regarding a method for long-term storage of a biocatalyst, there are known a freeze drying method of storing a biocatalyst in a powdered form, and a freeze preservation method of storing a biocatalyst by dissolving the biocatalyst in a solution under cryogenic conditions at a low concentration.

Generally, storage as a solution is desirable in view of the convenience of operation; however, in the case of a freeze preservation method, special apparatuses are required, and also, there are a problem that since ice is produced at the time of freezing, the conformation of a biocatalyst is destroyed, and a problem that when a frozen solution is used after thawing, the structure of the biocatalyst changes, and the activity is deteriorated. Furthermore, the storage concentration is, for example, in the case of urease or catalase, generally as low as about 1 to 3 mg/mL, and efficient preservation is difficult.

In order to prevent deactivation of such a biocatalyst and to retain the activity of an enzyme, attempts have been made to add stabilizers. For example, a method of using a polyhydric alcohol such as glycerin or sorbitol for the preservation of uricase (Patent Literature 1), and a method for stabilizing cholesterol oxidase by adding bovine serum albumin and sugars to a solution containing cholesterol oxidase (Patent Literature 2) have been proposed. However, in these methods, there is a problem of deterioration of enzyme activity in relation to the storage concentration, storage temperature, or storage period.

Furthermore, an ionic liquid is an organic salt which consists of a cation and an anion, and generally, ionic liquids composed of imidazolium-based cations or quaternary ammonium cations and various anions are known. Due to their structural features, investigations have been conducted on various applications of ionic liquids. Under such circumstances, it has been reported that enzyme activity is retained by adding an ionic liquid to a reaction solution of an enzyme or using an ionic liquid as a solvent for the reaction solution (Patent Literatures 3 and 4, and Non-Patent Literature 1); however, there is a problem concerning the dissolution concentration and preservability.

CITATION LIST

Patent Literature

Patent Literature 1: JP 06-70798 A
Patent Literature 2: JP 08-187095 A
Patent Literature 3: JP 2005-270007 A
Patent Literature 4: JP 2006-514832 W

Non Patent Literature

Non Patent Literature 1: Biomacromolecules, 2005, 6, 1457-1464

SUMMARY OF INVENTION

Technical Problem

In regard to conventional biocatalyst solvents, there is room for improvements in dissolubility for biocatalysts and retainability for the conformation of amino acid residues, and there is a demand for a method of dissolving an enzyme in a solution at a high concentration and retaining the activity under the conditions of higher temperature for a long time.

The present invention was achieved in view of such circumstances, and it is an object of the invention to provide a biocatalyst solvent in which a biocatalyst can be dissolved in a liquid at a high concentration and stored for a long time, over a range from a low temperature to a high temperature while retaining the activity of the biocatalyst.

It is another object of the invention to provide a biocatalyst solution in which a biocatalyst is dissolved in such a biocatalyst solvent.

Solution to Problem

In order to solve the problems described above, a biocatalyst solvent of the present invention consists of an ionic liquid including a quaternary ammonium cation represented by the following Formula (I) and an anion:

[Chemical Formula 1]

$$N^+[R^a]_n[R^b]_{4-n} \qquad (I)$$

wherein $R^a$'s each independently represent a hydroxyalkyl group having one or more hydroxyl groups and a linear or branched alkyl moiety having 1 to 10 carbon atoms, the alkyl moiety optionally containing an oxygen atom; a carboxyalkyl group having one or more carboxyl groups and a linear or branched alkyl moiety having 1 to 10 carbon atoms, the alkyl moiety optionally containing an oxygen atom; or a hydroxycarboxyalkyl group having one or more hydroxyl groups, one or more carboxyl groups and a linear or branched alkyl moiety having 1 to 10 carbon atoms, the alkyl moiety optionally containing an oxygen atom; $R^b$'s each independently represent a hydrogen atom, or a linear or branched alkyl group having 1 to 5 carbon atoms; and n represents an integer from 1 to 4.

The biocatalyst solution of the present invention includes the biocatalyst solvent described above and a biocatalyst.

Advantageous Effects of Invention

When the biocatalyst solvent of the present invention is used, a biocatalyst can be dissolved at a high concentration, and the biocatalyst in that solution can be dissolved at a high concentration and stored for a long time, over a range from a low temperature to a high temperature while retaining the activity of the biocatalyst.

DESCRIPTION OF EMBODIMENTS

Hereinafter, the present invention will be described in detail.

The biocatalyst solvent of the present invention may be an anhydrous ionic liquid or a hydrous ionic liquid that has absorbed the moisture in air, and consists of an ionic liquid containing a quaternary ammonium cation represented by Formula (I) and an anion.

In Formula (I), $R^a$'s of the quaternary ammonium cation each independently represent a hydroxyalkyl group having one or more hydroxyl groups and having a linear or branched alkyl moiety having 1 to 10 carbon atoms, in which the alkyl moiety may contain an oxygen atom; a carboxyalkyl group having one or more carboxyl groups and having a linear or branched alkyl moiety (not including the carbon atom of the carboxyl group) having 1 to 10 carbon atoms, in which the alkyl moiety may contain an oxygen atom; or a hydroxycarboxyalkyl group having one or more hydroxyl groups, one or more carboxyl groups and a linear or branched alkyl moiety (not including the carbon atom of the carboxyl group) having 1 to 10 carbon atoms, in which the alkyl moiety may contain an oxygen atom.

Here, in a case in which the alkyl moiety contains an oxygen atom, the oxygen atom forms, for example, an ether bond (—O—), a carbonyl group (—C=O), an aldehyde group (—CHO), or an ester bond (—C(=O)O—) in the alkyl moiety.

Examples of the hydroxyalkyl group for $R^a$ in Formula (I) include a mono-, di-, tri-, tetra-, penta-, hexa-, hepta- or octahydroxyalkyl group, a hydroxylalkoxyalkyl group, an alkoxyhydroxyalkyl group, and a hydroxypolyalkyleneoxy-alkyl group.

Examples of a monohydroxyalkyl group include a hydroxymethyl group, a 1-hydroxyethyl group, a 2-hydroxyethyl group, a 1-hydroxypropan-1-yl group, a 2-hydroxypropan-1-yl group, a 3-hydroxypropan-1-yl group, a 1-hydroxypropan-2-yl group, a 2-hydroxypropan-2-yl group, a 1-hydroxybutan-1-yl group, a 2-hydroxybutan-1-yl group, a 3-hydroxybutan-1-yl group, a 4-hydroxybutan-1-yl group, a 1-hydroxy-2-methylpropan-1-yl group, a 2-hydroxy-2-methylpropan-1-yl group, a 3-hydroxy-2-methylpropan-1-yl group, a 1-hydroxybutan-2-yl group, a 2-hydroxybutan-2-yl group, a 3-hydroxybutan-2-yl group, a 4-hydroxybutan-2-yl group, a 1-hydroxy-2-methylpropan-2-yl group, a 5-hydroxypentan-1-yl group, a 6-hydroxyhexan-1-yl group, a 7-hydroxyheptan-1-yl group, a 8-hydroxyoctan-1-yl group, a 9-hydroxynonan-1-yl group, and a 10-hydroxydecan-1-yl group. Among these monohydroxyalkyl groups, a group having 1 to 5 carbon atoms is preferred, and a group having 1 to 3 carbon atoms is more preferred.

Examples of a di-, tri-, tetra-, penta-, hexa-, hepta- or octahydroxyalkyl group include a dihydroxyethyl group such as a 1,2-dihydroxyethyl group; a dihydroxypropan-1-yl group such as a 1,2-dihydroxypropan-1-yl group or a 2,3-dihydroxypropan-1-yl group; a dihydroxypropan-2-yl group such as a 1,2-dihydroxypropan-2-yl group or a 1,3-dihydroxypropan-2-yl group; a trihydroxypropan-1-yl group; a trihydroxypropan-2-yl group; a dihydroxybutan-1-yl group such as a 1,2-dihydroxybutan-1-yl group, a 1,3-dihydroxybutan-1-yl group, a 1,4-dihydroxybutan-1-yl group, a 2,3-dihydroxybutan-1-yl group, a 2,4-dihydroxybutan-1-yl group, or a 3,4-dihydroxybutan-1-yl group; a trihydroxybutan-1-yl group such as a 1,2,3-trihydroxybutan-1-yl group, a 1,2,4-trihydroxybutan-1-yl group, a 1,3,4-trihydroxybutan-1-yl group, or a 2,3,4-trihydroxybutan-1-yl group; a tetrahydroxybutan-1-yl group; a dihydroxy-2-methylpropan-1-yl group such as a 1,2-dihydroxy-2-methylpropan-1-yl group, a 1,3-dihydroxy-2-methylpropan-1-yl group, or a 2,3-dihydroxy-2-methylpropan-1-yl group; a trihydroxy-2-methylpropan-1-yl group; a tetrahydroxy-2-methylpropan-1-yl group; a dihydroxybutan-2-yl group such as a 1,2-dihydroxybutan-2-yl group, a 1,3-dihydroxybutan-2-yl group, a 1,4-dihydroxybutan-2-yl group, a 2,3-dihydroxybutan-2-yl group, a 2,4-dihydroxybutan-2-yl group, or a 3,4-dihydroxybutan-2-yl group; a trihydroxybutan-2-yl group such as a 1,2,3-trihydroxybutan-2-yl group, a 1,2,4-trihydroxybutan-2-yl group, a 1,3,4-trihydroxybutan-2-yl group, or a 2,3,4-trihydroxybutan-2-yl group; a tetrahydroxybutan-2-yl group; a 1,3-dihydroxy-2-methylpropan-2-yl group, a 1,3-dihydroxy-2-ethylpropan-2-yl group, a 1,3-dihydroxy-2-hydroxymethylpropan-2-yl group; a di-, tri-, tetra- or pentahydroxypentan-1-yl group; a di-, tri-, tetra-, penta- or hexahydroxyhexan-1-yl group; a di-, tri-, tetra-, penta-, hexa- or heptahydroxyheptan-1-yl group; and a di-, tri-, tetra-, penta-, hexa-, hepta- or octahydroxyoctan-1-yl group. Among these hydroxyalkyl groups, a linear hydroxyalkyl group having 2 to 6 hydroxyl groups and 3 to 8 carbon atoms, or a branched hydroxyalkyl group represented by the following formula is preferred:

[Chemical Formula 2]

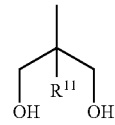

wherein $R^{11}$ represents a hydrogen atom, a linear alkyl group having 1 to 3 carbon atoms, or a linear monohydroxyalkyl group having 1 to 3 carbon atoms. Among these hydroxyalkyl groups, a 2,3-dihydroxypropan-1-yl group, a 1,3-dihydroxypropan-2-yl group, a 1,3-dihydroxy-2-ethylpropan-2-yl group, a 1,3-dihydroxy-2-hydroxymethylpropan-2-yl group, and a pentahydroxyhexan-1-yl group are preferred.

An example of the carboxyalkyl group for $R^a$ in Formula (I) may be a group obtained by substituting the hydroxyl groups of a mono-, di-, tri-, tetra-, penta-, hexa-, hepta- or octahydroxyalkyl group mentioned above as examples, with carboxyl groups.

Examples of a monocarboxyalkyl group include a carboxymethyl group, a 1-carboxyethyl group, a 2-carboxyethyl group, a 1-carboxypropan-1-yl group, a 2-carboxypropan-1-yl group, a 3-carboxypropan-1-yl group, a 1-carboxypropan-2-yl group, a 2-carboxypropan-2-yl group, a 1-carboxybutan-1-yl group, a 2-carboxybutan-1-yl group, a 3-carboxybutan-1-yl group, a 4-carboxybutan-1-yl group, a 1-carboxy-2-methylpropan-1-yl group, a 2-carboxy-2-methylpropan-1-yl group, a 3-carboxy-2-methylpropan-1-yl group, a 1-carboxybutan-2-yl group, a 2-carboxybutan-2-yl group, a 3-carboxybutan-2-yl group, a 4-carboxybutan-2-yl group, a 1-carboxy-2-methylpropan-2-yl group, a 5-carboxypentan-1-yl group, a 6-carboxyhexan-1-yl group, a 7-carboxyheptan-1-yl group, a 8-carboxyoctan-1-yl group, a 9-carboxynonan-1-yl group, and a 10-carboxydecan-1-yl group. Among these carboxyl group-containing alkyl groups, a group having 1 to 5 carbon atoms is preferred, and a group having 1 to 3 carbon atoms is more preferred.

An example of the hydroxycarboxyalkyl group for Formula (I) may be a group obtained by substituting some hydroxyl groups of the di-, tri-, tetra-, penta-, hexa-, hepta-, or octahydroxyalkyl group mentioned above as examples, with carboxyl groups.

In regard to Formula (I), $R^b$'s each independently represent a hydrogen atom or a linear or branched alkyl group having 1 to 5 carbon atoms. Examples of the alkyl group include a methyl group, an ethyl group, a propan-1-yl group, a propan-2-yl group, a butan-1-yl group, a 2-methylpropan-1-yl group, a butan-2-yl group, a 2-methylpropan-1-yl group, a penta-1-yl group, a 1-methylbutan-1-yl group, a 2-methylbutan-1-yl group, a 3-methylbutan-1-yl group, a 1-ethylbutan-1-yl group, a 1,1-dimethylpropan-1-yl group, a 1,2-dimethylpropan-1-yl group, and a 2,2-dimethylpropan-1-yl group. Among them, a hydrogen atom or an alkyl group having 1 to 3 carbon atoms is preferred, and a hydrogen atom, a methyl group and an ethyl group are more preferred.

In regard to Formula (I), n represents an integer from 1 to 4, and an integer from 1 to 3 is preferred.

The anion of the ionic liquid used for the present invention is not particularly limited, and examples thereof include a halogen-based anion, a sulfur-based anion, a phosphorus-based anion, a cyan-based anion, a boron-based anion, a fluorine-based anion, a nitrogen oxide-based anion, and a carboxylate anion.

Examples of the halogen-based anion include chloride ion, bromide ion, and iodide ion.

Examples of the sulfur-based anion include sulfate anion, hydrogen sulfate anion, an alkylsulfonate anion (for example, methanesulfonate anion, ethylsulfonate anion, butylsulfonate anion, benzenesulfonate anion, p-toluenesulfonate anion, 2,4,6-trimethylbenzenesulfonate anion, styrenesulfonate anion, 3-sulfopropylmethacrylate anion, and 3-sulfopropylacrylate anion), and an alkylsulfate anion (for example, methylsulfate anion, ethylsulfate anion, butylsulfate anion, octylsulfate anion, and 2-(2-methoxyethoxy) ethylsulfate anion).

Examples of the phosphorus-based anion include phosphate anion, hydrogen phosphate anion, dihydrogen phosphate anion, phosphonate anion, hydrogen phosphonate anion, phosphinate anion, an alkylphosphate anion (for example, dimethylphosphate anion, diethylphosphate anion, dipropylphosphate anion, or dibutylphosphate anion), an alkylphosphonate anion (for example, methylphosphonate anion, ethylphosphonate anion, propylphosphonate anion, butylphosphonate anion, or methylmethylphosphonate anion), an alkylphosphinate anion, and a hexaalkylphosphate anion.

Examples of the cyan-based anion include tetracyanoborate anion, dicyanamide, thiocyanate anion, and isothiocyanate anion.

Examples of the boron-based anion include tetrafluoroborate anion, bisoxalatoborate anion, and a tetraalkylborate anion such as tetraphenylborate.

Examples of the fluorine-based anion include bis(fluorosulfonyl)imide anion, a bis(perfluoroalkylsulfonyl)imide anion (for example, bis(trifluoromethylsulfonyl)imide anion, bis(pentafluoroethylsulfonyl)imide, bis(heptafluoropropansulfonyl)imide anion, or bis(nonafluorobutylsulfonyl)imide), a perfluoroalkylsulfonate anion (for example, trifluoromethanesulfonate anion, pentafluoroethanesulfonate anion, heptafluoropropansulfonate anion, nonaflate anion, or perfluorooctanesulfonate anion), a fluorophosphate anion (for example, hexafluorophosphate anion, or tri(pentafluoroethyl)trifluorophosphate anion), a tris(perfluoroalkylsulfonyl)methide anion (for example, tris(trifluoromethanesulfonyl)methide anion, tris(pentafluoroethanesulfonyl)methide anion, tris(heptafluoropropansulfonyl)methide anion, or tris(nonafluorobutanesulfonyl)methide anion), and fluorohydrogenate anion.

Examples of the nitrogen oxide-based anion include nitrate anion and nitrite anion.

The carboxylate anion is an organic acid anion having at least one or more carboxylate anion ($-COO^-$) in the molecule, and may contain a functional group having a heteroatom such as an oxygen atom, a nitrogen atom or a sulfur atom. There are no particular limitations, but examples of the carboxylate anion include a saturated aliphatic carboxylate anion, an unsaturated aliphatic carboxylate anion, an alicyclic carboxylate anion, an aromatic carboxylate anion, a saturated aliphatic hydroxycarboxylate anion, an unsaturated aliphatic hydroxycarboxylate anion, an alicyclic hydroxycarboxylate anion, an aromatic hydroxycarboxylate anion, a carbonylcarboxylate anion, an alkyl ether carboxylate anion, a halogen carboxylate anion, and an amino acid anion.

The saturated aliphatic carboxylate anion is formed from a linear or branched, saturated aliphatic hydrocarbon group and one or more carboxylate anions, and the number of carbon atoms is preferably 1 to 22. Specific examples thereof include anions obtained as a result of dissociation of protons from formic acid, acetic acid, propionic acid, butyric acid, valeric acid, caproic acid, enanthic acid, caprylic acid, pelargonic acid, capric acid, lauric acid, myristic acid, pentadecanoic acid, palmitic acid, margaric acid, stearic acid, behenic acid, isobutyric acid, 2-methylbutyric acid, isovaleric acid, 2-ethylhexanoic acid, isononanoic acid, isopalmitic acid, isostearic acid, oxalic acid, malonic acid, succinic acid, glutaric acid, adipic acid, pimelic acid, suberic acid, azelaic acid, and sebacic acid.

The unsaturated aliphatic carboxylate anion is formed from a linear or branched, unsaturated aliphatic hydrocarbon group and one or more carboxylate anions, and the number of carbon atoms is preferably 3 to 22. Specific examples thereof include anions obtained as a result of dissociation of protons from acrylic acid, methacrylic acid, crotonic acid, palmitoleic acid, oleic acid, vaccenic acid, linoleic acid, linolenic acid, eleostearic acid, arachidonic acid, maleic acid, and fumaric acid.

The alicyclic carboxylate anion is formed from a saturated or unsaturated carbon ring without aromaticity and one or more carboxylate anions, and the number of carbon atoms is preferably 6 to 20. Above all, an alicyclic carboxylate anion having a cyclohexane ring skeleton is preferred, and specific examples thereof include anions obtained as a result of dissociation of protons from cyclohexanecarboxylic acid and cyclohexanedicarboxylic acid.

The aromatic carboxylate anion is formed from a monocyclic or polycyclic ring having aromaticity and one or more carboxylate anions, and the number of carbon atoms is preferably 6 to 20. Above all, an aromatic carboxylate anion having a benzene ring skeleton is preferred, specific examples thereof include anions obtained as a result of dissociation of protons from benzoic acid, cinnamic acid, phthalic acid, isophthalic acid, and terephthalic acid.

The saturated aliphatic hydroxycarboxylate anion is formed from a linear or branched aliphatic saturated hydrocarbon group, one or more carboxylate anions, and one or more hydroxyl groups, and the number of carbon atoms is preferably 2 to 24. Above all, a saturated aliphatic hydroxycarboxylate anion having 1 to 4 hydroxyl groups and 2 to 7 carbon atoms is preferred. Specific examples thereof include anions obtained as a result of dissociation of protons from glycolic acid, lactic acid, tartronic acid, glyceric acid, hydroxyacetic acid, hydroxybutyric acid, 2-hydroxydecanoic acid, 3-hydroxydecanoic acid, 12-hydroxystearic acid, dihydroxystearic acid, cerebronic acid, malic acid, tartaric acid, citramalic acid, citric acid, isocitric acid, leucine acid, mevalonic acid, and pantoic acid.

The unsaturated aliphatic hydroxycarboxylate anion is formed from a linear or branched aliphatic unsaturated hydrocarbon group, one or more carboxylate anion, and one or more hydroxyl groups, and the number of carbon atoms is preferably 3 to 22. Specific examples thereof include anions obtained as a result of dissociation of protons from ricinolic acid, ricinoleic acid, and ricinelaidic acid.

The alicyclic hydroxycarboxylate anion is formed from a saturated or unsaturated carbon ring without aromaticity, one or more carboxylate anions, and one or more hydroxyl groups, and the number of carbon atoms is preferably 6 to 20. Above all, an alicyclic hydroxycarboxylate anion having a 6-membered ring skeleton with 1 to 4 hydroxyl groups is preferred, and specific examples thereof include anions obtained as a result of dissociation of protons from hydroxycyclohexanecarboxylic acid, dihydroxycyclohexanecarboxylic acid, quinic acid (1,3,4,5-tetrahydroxycyclohexanecarboxylic acid), and shikimic acid.

The aromatic hydroxycarboxylate anion is formed from a single ring or multiple rings having aromaticity, one or more carboxylate anions, and one or more hydroxyl groups, and the number of carbon atoms is preferably 6 to 20. Above all, an aromatic carboxylate anion having a benzene ring skeleton with 1 to 3 hydroxyl groups is preferred, and specific examples thereof include anions obtained as a result of dissociation of protons from salicylic acid, hydroxybenzoic acid, dihydroxybenzoic acid, trihydroxybenzoic acid, hydroxymethylbenzoic acid, vanillic acid, syringic acid, pyrotocatechuic acid, gentisic acid, orsellic acid, mandelic acid, benzilic acid, atrolactic acid, phloretic acid, coumaric acid, umbellic acid, caffeic acid, ferulic acid, and sinapic acid.

The carbonylcarboxylate anion is a carboxylate anion having 3 to 22 carbon atoms and having a carbonyl group in the molecule, and a carbonylcarboxylate anion having 1 to 2 carbonyl groups and 3 to 7 carbon atoms is preferred. Above all, a carbonylcarboxylate anion represented by the formula: $CH_3((CH_2)_pCO(CH_2)_q)COO^-$ (wherein p and q each represent an integer from 0 to 2) is preferred. Specific examples include an anion obtained as a result of dissociation of protons from pyruvic acid.

The alkyl ether carboxylate anion is a carboxylate anion having 2 to 22 carbon atoms and an ether group in the molecule, this carboxylate anion including a polyoxyethylene alkyl ether carboxylate anion. An alkylcarboxylate anion having 1 to 2 ether groups and 2 to 12 carbon atoms is preferred. Above all, an alkyl ether carboxylate anion represented by $CH_3(CH_2)_rO(CH_2)_sCOO^-$ (wherein r and s each represent an integer from 0 to 4) is preferred. Specific examples include anions obtained as a result of dissociation of protons from methoxyacetic acid, ethoxyacetic acid, methoxybutyric acid, and ethoxybutyric acid.

The halogen carboxylate anion is preferably a halogen carboxylate anion having 2 to 22 carbon atoms. Specific examples include anions obtained as a result of dissociation of protons from fluorine-substituted halogen carboxylic acids such as trifluoroacetic acid, pentafluoropropionic acid, and perfluorononanoic acid.

The amino acid anion is not particularly limited, and examples include anions obtained as a result of dissociation of protons from glycine, alanine, glutamic acid, arginine, asparagine, aspartic acid, isoleucine, glutamine, histidine, cysteine, leucine, lysine, proline, phenylalanine, threonine, serine, tryptophan, tyrosin, methionine, valine, sarcosine, aminobutyric acid, methylleucine, aminocaprylic acid, aminohexanoic acid, norvaline, aminovaleric acid, aminoisobutyric acid, thyroxine, creatine, ornithine, opine, theanine, tricholomic acid, kainic acid, domoic acid, ibotenic acid, acromelic acid, cystine, hydroxyproline, phosphoserine, and desmosine.

An ionic liquid has a melting point of 100° C. or lower in a broad sense. The ionic liquid of the present invention is preferably liquid at a lower temperature from the viewpoint of suppressing denaturation of a biocatalyst caused by dissolution when the biocatalyst is stored at low temperature, and from the viewpoint of convenience upon use. Depending on the selection of a functional group or a characteristic group of the quaternary ammonium cation and selection of the anion, the melting point (freezing point) is preferably lower than −5° C., and particularly preferably lower than −10° C. Furthermore, the ionic liquid is non-volatile due to the structural characteristics of organic salts, causes less concentration change in a solution when a biocatalyst is preserved therein, and is highly convenient in view of the accuracy of the set concentration and retention of the storage concentration (activity retention) during a use of the biocatalyst.

The biocatalyst solvent of the present invention increases solubility of a biocatalyst due to the presence of a hydrogen bondable functional group (a hydroxyl group, a carboxyl group, an ether group, or a hydrogen atom) in the cation, and therefore, the biocatalyst solvent of the present invention exhibits higher dissolubility than a tetraalkylammonium cation or an imidazolium-based ionic liquid, which are composed of alkyl groups only instead of hydrogen-bondable functional groups. Furthermore, the solubility of a biocatalyst can be further increased by using a cation composed only of hydrogen-bondable functional groups or imparting a hydrogen-bondable functional group to the anion.

There are no particular limitations on the anion having a hydrogen-bondable functional group; however, a carboxylate anion, a sulfonate anion and a phosphate anion, all of which have hydrogen-bondable oxygen atoms in the anion moiety, are desirable.

The biocatalyst solution of the present invention includes the biocatalyst solvent described above and a biocatalyst. The method for dissolving a biocatalyst in the biocatalyst solvent is not particularly limited, and a biocatalyst can be dissolved in a liquid biocatalyst solvent by adding the biocatalyst to the solvent by an appropriate method.

The ionic liquid of the present invention can be synthesized, for example, in the following manner.

A compound in which $R^a$ in Formula (I) represents a hydroxyalkyl group, a carboxyalkyl group, or a hydroxycarboxyalkyl group, and $R^b$ represents a hydrogen atom, can be synthesized as follows.

An alkanolamine having one or more hydroxyl groups corresponding to $R^a$ or $R^b$ in Formula (I), an amino acid having one or more carboxyl groups, an am inohydroxyalkanoic acid having one or more hydroxyl groups and one or more carboxyl groups, and an organic acid or inorganic acid corresponding to an anion, are allowed to react in a solvent such as water or an organic solvent. Alternatively, an alkanolamine having one or more hydroxyl groups corresponding to $R^a$ or $R^b$ in Formula (I), an amino acid having one or more carboxyl groups, an am inohydroxyalkanoic acid having one or more hydroxyl groups and one or more carboxyl groups, and an organic halogen compound such as an alkylene halohydrin, a monohaloalkylcarboxylic acid, or a monohalohydroxyalkylcarboxylic acid, are allowed to react in a solvent, and a compound thus obtained is reacted with an organic acid or inorganic acid corresponding to the anion of the intended compound in a solvent such as water or an organic solvent.

An alkanolamine configured to include a hydroxyalkyl group having one or more hydroxyl groups corresponding to the quaternary ammonium cation represented by Formula (I) (for example, a mono-, di- or trialkanolamine, 2-amino-1,3-propanediol, 2-amino-2-ethyl-1,3-propanediol, tris(hydroxymethyl)aminomethane, or D-glucamine), an amino acid configured to include a carboxyalkyl group having 1 to 8 carboxyl groups (for example, glycine, aspartic acid, or glutamic acid), or an aminohydroxyalkanoic acid having one or more hydroxyl groups and one or more carboxyl groups (for example, 3-amino-2-hydroxypropionic acid), is reacted with an organic acid or inorganic acid corresponding to an anion in a polar solvent such as water or acetonitrile. The reaction temperature and the reaction time may vary depending on the type of the raw materials and the like; however, for example, the reaction may be carried out at room temperature for about 1 hour to 1 day. Subsequently, the solvent is distilled off under reduced pressure, the residue is purified as necessary, and thereby the intended ionic liquid can be obtained as a liquid substance. Also, in a case in which the reaction has been completed by causing the compounds to react at equimolar proportions, a purification process is not needed, and the production process can be further simplified.

A compound in which $R^a$ in Formula (I) represents a hydroxyalkyl group, a carboxyalkyl group or a hydroxycarboxyalkyl group, and $R^b$ represents an alkyl group, can be synthesized, for example, in the following manner.

As an initial step, an organic halogen compound corresponding to the structure of Formula (I), such as an alkylene halohydrin or a monohaloalkylcarboxylic acid, is reacted with an alkylamine, or an organic halogen compound such as an alkyl halide is reacted with an amine-based compound such as an alkanolamine, an amino acid or an aminohydroxyalkanoic acid, in a solvent such as acetonitrile. The reaction temperature and the reaction time may vary depending on the type of the raw materials and the like; however, for example, the reaction may be carried out at room temperature for about 1 day. After the reaction, a solid thus precipitated is separated by filtration and washed, and then anion exchange is performed as a subsequent process. When anion exchange is performed, for example, the reaction product thus obtained is reacted with an acid corresponding to the anion of Formula (I) in water. The reaction temperature and the reaction time may vary depending on the type of the raw materials and the like; however, for example, the reaction may be carried out at room temperature for about 1 day, or an ion exchange resin or the like can be used. Regarding the ion exchange resin to be used, a strongly basic ion exchange resin that is commercially available for water treatment or catalyst can be used.

Subsequently, water is distilled off under reduced pressure, and the residue is washed. Thus, an intended compound can be obtained.

Furthermore, a compound in which $R^a$ of Formula (I) consists of a monohydroxyalkyl group, a carboxyalkyl group having two or more carboxyl groups, a hydroxyalkyl group having two or more hydroxyl groups, or a monocarboxyalkyl group, and $R^b$ represents a hydrogen atom or does not exist (n is 4), can be synthesized, for example, in the following manner.

In order to obtain a compound corresponding to the structure of the quaternary ammonium cation represented by Formula (I), a mono-, di- or trialkanolamine is reacted with an organic halogen compound such as a haloalkylcarboxylic acid having two or more carboxyl groups, or an amino-(mono-, di- or tri-)alkanoic acid is reacted with an organic halogen compound such as an alkylene halohydrin, in a polar solvent such as water or acetonitrile. The reaction temperature and the reaction time may vary depending on the type of the raw materials and the like; however, for example, the reaction may be carried out at room temperature for about one day. Subsequently, the reaction product is washed, and thus a compound formed from a quaternary ammonium cation represented by Formula (I) and a halide ion can be obtained. Further, in a case in which the halide ion is to be replaced with an intended anion, anion exchange is performed. When anion exchange is performed, for example, the chemical compound thus obtained is reacted with an organic acid or inorganic acid corresponding to the intended anion in water. The reaction temperature and the reaction time may vary depending on the type of the raw materials and the like; however, for example, the reaction may be carried out at room temperature for about 1 day. Alternatively, an intended ionic liquid can be obtained by performing anion exchange with hydroxide anion using a strongly basic ion exchange resin or the like, and then further performing anion exchange using an organic acid or inorganic acid corresponding to the anion of the intended compound.

Furthermore, a compound in which $R^a$ of Formula (I) consists of a hydroxycarboxyalkyl group and a hydroxyalkyl group or a carboxyalkyl group, and $R^b$ represents a hydrogen atom or does not exist (n is 4), can be synthesized, for example, in the following manner.

As an initial step, in order to obtain a compound corresponding to the structure of the quaternary ammonium cation represented by Formula (I), an aminohydroxyalkanoic acid having one or more hydroxyl groups and one or more carboxyl groups (for example, 3-amino-2-hydroxypropionic acid) is reacted with a hydroxyalkyl halide having two or more hydroxyl groups, or a haloalkylcarboxylic acid having two or more carboxyl groups, in a polar solvent such as water or acetonitrile. The reaction temperature and the reaction time may vary depending on the type of the raw materials and the like; however, for example, the reaction may be carried out at room temperature for about 1 day. Subsequently, the reaction product is washed, and thus a compound formed from a quaternary ammonium cation represented by Formula (I) and a halide ion can be obtained. Further, in a case in which the halide ion is to be replaced with an intended anion, anion exchange is performed. When anion exchange is performed, for example, the chemical reaction product thus obtained is reacted with an organic acid or inorganic acid corresponding to the anion of the intended compound in water. The reaction temperature and the reaction time may vary depending on the type of the raw materials and the like; however, for example, the reaction may be carried out at room temperature for about 1 day. Alternatively, an intended ionic liquid can be obtained by performing anion exchange with hydroxide anion using a strongly basic ion exchange resin or the like, and then further performing anion exchange using an organic acid or inorganic acid corresponding to the anion of the intended compound.

The biocatalyst solvent of the present invention consists of an ionic liquid containing the quaternary ammonium cation represented by Formula (I) and the anion described above.

A biocatalyst is a catalyst for a biochemical reaction, and examples of the biocatalyst according to the present invention include a biologically derived microorganism, an animal cell or plant cell, a tissue; an enzyme derived from one of those living organisms; an artificial compound having an enzymatic function; and an artificial enzyme imparted with new performance by subjecting a natural enzyme or a natural biological molecule to artificial modification.

In an enzyme, amino acids are one-dimensionally linked to adopt a primary structure; however, a two-dimensional or higher-dimensional structure is determined by the state of arrangement and the number of the amino acids. These structures determine the properties characteristics to each of various enzymes.

In a primary structure, 20 kinds of amino acids are one-dimensionally arranged by peptide bonds. Many enzymes are configured to include 100 to 300 amino acids, and the order of arrangement of amino acids is one piece of information determining the characteristics of an enzyme. In a secondary structure, a certain portion (multiple portions) in the entire one-dimensional arrangement has a highly-ordered regular structure such as an α-helix, a β-sheet, or a β-turn. In a tertiary structure, primary structures and secondary structures adopt a three-dimensional conformation. This conformation determines the active center, which is a place as a reaction catalyst in an enzyme, or a three-dimensional structure of amino acid residues composed of hydrophilic portions and hydrophobic portions, and expresses chemical reactions exhibiting substrate specificity and reaction specificity characteristic to a biocatalyst such as an enzyme, which is absent in general proteins (a structural protein, a transport protein, a reserve protein, a contractile protein, a defensive protein, and a hormone protein). A quaternary structure is an associate formed from multiple enzyme molecules that have adopted a three-dimensional structure. That is, a biocatalyst such as an enzyme has reaction specificity caused by primary to quaternary structures, in addition to the substrate specificity shown by proteins, and in order to retain activity directed to a catalytic reaction, it is important to retain not only the primary and secondary structures, but also tertiary and quaternary structures.

Examples of an enzyme to which the biocatalyst solvent of the present invention can be applied include an oxidation-reduction enzyme (oxidoreductase), a transfer enzyme (transferase), a hydrolysis enzyme (hydrolase), an elimination enzyme (lyase), an isomerization enzyme (isomerase), and a synthesis enzyme (ligase).

Examples of the oxidoreductase include glucose oxidase, alcohol oxidase, glucose dehydrogenase, alcohol dehydrogenase, fructose dehydrogenase, gluconate dehydrogenase, aldehyde dehydrogenase, amine dehydrogenase, succinic acid dehydrogenase, p-cresol methylhydroxylase, histamine dehydrogenase, fumarate reductase, nitrate reductase, arsenate reductase, sulfite reductase, catalase, peroxidase, and cytochrome P450.

Examples of the transferase include citrate synthase, methyltransferase, phosphotransferase, glycine hydroxymethyltransferase, transketolase, aspartate transaminase, hexokinase, glycerol kinase, creatine kinase, transaminase, and transacylase.

Examples of the hydrolase include carboxyl esterase, acetyl-CoA hydrolase, alkali phosphatase, phospholipase, arylsulfatase, amylase, glucoamylase, cellulase, DNA glycosylase, trypsin, chymotrypsin, pepsin, urease, serine protease, and lipase.

Examples of the lyase include alginate lyase, pyruvate carboxylase, phosphoketoketolase, citrate lyase, phospho- pyruvate hydratase, tryptophan synthase, pectin lyase, aspartate ammonia lyase, cysteine lyase, adenylate cyclase, and ferrochelatase.

Examples of the isomerase include amino acid racemase, tartrate epimerase, glucose-6-phosphate 1-epimerase, maleate isomerase, phenylpyruvate tautom erase, phosphoglucose isom erase, phosphomannomutase, and tyrosine-2,3-aminomutase.

Examples of the ligase include tyrosine tRNA ligase, acetyl-CoA synthetase, asparagine synthetase, GMP synthase, pyruvate carboxylase, and DNA ligase.

Examples of the microorganism to which the biocatalyst solvent of the present invention can be applied include prokaryotes (bacteria, *Actinomyces*, and archaebacteria), and eukaryotes (fungi, yeast, mushrooms, algae, and protozoa). Examples of the animal and plant cells include animal cells, plant cells, cultured animal cells, and cultured plant cells.

Examples of the animal-derived and plant-derived tissues include animal tissues and plant tissues.

Many of biocatalysts such as enzymes and yeasts are prone to have their molecular conformation destroyed by the influence of temperature, pH, solvent, intermolecular electrostatic repulsion or the like, and have their activity, that is, catalytic ability, deteriorated. Therefore, regarding a long-term storage method for a biocatalyst, a freeze drying method in a powdered state, and a freeze preservation method of storing a biocatalyst by dissolving the biocatalyst in a solution under cryogenic conditions at a low concentration are known. However, in the case of a freeze preservation method, special apparatuses are needed, and also, when a frozen solution is used after melting, the structure of the biocatalyst changes and cause deterioration of the activity in many cases. Furthermore, the storage concentration is low, and efficient preservation is difficult.

In order to increase the solubility of an enzyme, it is necessary to consider various factors. For example, an interaction between enzyme molecules caused by a repulsive force produced by the charge carried by the enzyme molecules (Coulomb interaction) is suppressed by addition of a salt or the like into an enzyme solution, and it is important to allow more enzyme molecules to exist in a unit volume and to increase the affinity between the solvent and amino acid residues such as a hydroxyl group, a carbonyl group and an amino group existing in abundance on the enzyme surface.

Since an ionic liquid formed from a salt structure between an anion and a cation can suppress interactions between enzyme molecules, the ionic liquid is expected to increase the solubility of an enzyme. However, conventionally known imidazolium-based and tetraalkylammonium-based ionic liquids have low affinity with enzyme surfaces and low dissolubility with respect to enzymes. On the other hand, polyhydric alcohol-based compounds such as glycerin, propylene glycol, glucose and trehalose, which have hydroxyl groups having affinity to amino acid residues such as a hydroxyl group, a carbonyl group and an amino group on the enzyme surface, have a low effect of suppressing interactions between enzyme molecules and have low dissolubility with respect to enzymes. Furthermore, since imidazolium-based ionic liquids having hydroxyl groups have a rigid cyclic structure, the ionic liquids have low affinity to enzymes, and therefore, their dissolubility with respect to enzymes is low.

In contrast to these, since the biocatalyst solvent of the present invention is an ionic liquid formed from a salt structure of an anion and a cation, the biocatalyst solvent can suppress interactions between enzyme molecules, and high dissolubility is obtained due to a structure which has a hydrogen-bondable functional group in the cation, has high affinity with amino residues such as a hydroxyl group, a carbonyl group and an amino group on the enzyme surface, has a small molecular size, and is soft. Furthermore, dissolubility can be further increased by also having a hydrogen-bondable functional group in the anion.

In regard to the preservability for enzyme activity, it is necessary to retain the conformation of an enzyme. Generally, an enzyme has substrate specificity expressed from amino acid residue, and reaction specificity, and works as a reaction catalyst. Substrate specificity refers to the property of recognizing and selecting the structure of a substrate to be bound, based on the conformation of a reaction site and the amino acid residues, and reacting only with a specific substrate. Reaction specificity means that an enzyme catalyzes only a specific chemical reaction, and this involves the conformation of a reaction site, amino acid residues, and metal ions that some enzymes have. For example, a metal ion existing inside an enzyme such as an oxidoreductase forms a three-dimensional complex with amino acid residues and expresses catalytic action. That is, a primary cause for substrate specificity, reaction specificity, and deactivation of a metal ion or the like is destruction of the conformation of amino acid residues. Therefore, it is important to retain the conformation of an enzyme by protecting the amino residues such as a hydroxyl group, a carbonyl group and an amino group that express hydrophilicity of the enzyme surface, hydrophilic amino acid residues such as a hydroxyl group, a carbonyl group and amino group inside the enzyme at an active site, and amino acid residues having hydrophobic functional groups.

Water and buffers that are conventionally used as solvents for enzymes have high affinity with hydrophilic sites on the enzyme surface; however, they cannot protect the conformation of hydrophobic sites inside an enzyme, which become critical for expressing substrate specificity and reaction specificity, and cannot retain catalytic activity. There are occasions in which an aqueous solution of bovine serum albumin, which is a protein, is used as a stabilizer; however, there is a risk for infection of BSE or the like, and use of bovine serum albumin in the field of medicine is not appropriate. Aqueous solutions using polyhydric alcohol-based stabilizers such as glycerin, propylene glycol, glucose and trehalose exhibit affinity between hydrophilic sites on the enzyme surface and hydroxyl groups of these polyhydric alcohols, and affinity between hydroxyl groups and a hydrophobic alkyl chain of a polyhydric alcohol and the hydrophilic sites and hydrophobic sites inside an enzyme having active spots, respectively, and thus those polyhydric alcohol-based stabilizers can retain the conformation of an enzyme. However, their storage stabilizing effect is low. In aqueous solutions of surfactants (amino acids) such as glycine and lysine, the hydrophobic moiety of a surfactant binds to the hydrophobic amino acid residues in a hydrophobic region inside an enzyme, and the hydrophobic region becomes hydrophilic as electric charges are generated, and moves toward the hydrophilic surface. Therefore, the conformation of the enzyme is destroyed and deactivated. Furthermore, ionic liquids that do not have hydrogen-bondable functional groups, such as an imidazolium-based ionic liquid and a tetraalkylammonium-based ionic liquid, which are conventionally known as ionic liquids, cannot protect hydrophilic amino residues on the surface and inside of an enzyme, and therefore, these ionic liquids have low preservability for the enzyme.

In contrast to this, in the biocatalyst solvent of the present invention, the hydrogen-bondable functional groups present in the cation and anion in the ionic liquid structure form hydrogen bonds with the amino acid residues such as a hydroxyl group, a carbonyl group and an amino group of the amino acid residues on the surface and inside an enzyme, and thereby the biocatalyst solvent protects the amino acid residues. Furthermore, as the biocatalyst solvent simultaneously protects amino acid residues having internal hydrophobic functional groups at hydrophobic sites of the alkyl chain in the ionic liquid, the biocatalyst solvent can retain the conformation of an enzyme even under a high concentration condition for a long time, and can maintain the catalytic activity.

Also, the biocatalyst solvent of the present invention is formed from a combination of a cation having a hydrogen-bondable functional group (a hydroxyl group, a carboxyl group, an ether group, or a hydrogen atom) and an anion, and due to the electrostatic interaction, the biocatalyst solvent has higher retainability for the conformation of an enzyme and has higher retainability for the activity of an enzyme, compared to nonionic compounds having hydrogen-bondable functional groups.

Furthermore, since the biocatalyst solvent of the present invention has a small molecular size and a flexible structure, even if the biocatalyst solvent contains hydroxyl groups, the molecules of the present ionic liquid efficiently infiltrate into the interior of complicated conformations and protect amino acid residues without steric distortion, compared to an imidazolium-based ionic liquid having a cyclic rigid structure. Thus, the biocatalyst solvent has high retainability for the activity of an enzyme.

An oxidoreductase is an enzyme that expresses catalytic action by causing migration of hydrogen atoms from a substrate, migration of electrons, and addition of oxygen atoms. Many of oxidoreductases express catalytic action by changing the valence of a metal ion in an enzyme as a result of electron migration.

A transferase is an enzyme that catalyzes a reaction of moving atomic groups (functional groups) from one substrate to another substrate. Since only those functional groups existing in a reacting substrate undergo a transfer reaction, it is particularly important to maintain the conformation for making the substrate suitable.

A hydrolase is an enzyme that causes a substrate to react with water, a hydroxyl group in an amino acid residue of an enzyme, or the like, and thereby breaks (hydrolyzes) a particular bond in the substrate.

A lyase is an enzyme that breaks a carbon-carbon bond, a carbon-oxygen bond and the like in a substrate from substrate molecules, without depending on oxidation or hydrolysis. Many of lyases break bonds in the substrate molecules by causing a metal ion to react with a substrate and producing an intermediate.

An isomerase is an enzyme that converts a substrate to a stereoisomer having a different spatial disposition. Therefore, the conformation of amino acid residues in the enzyme that binds to a substrate becomes important.

A ligase is an enzyme that binds a substrate and another substrate by utilizing the hydrolysis energy of ATP. Regarding the reaction, two substrate molecules are reacted by means of an intermediate formed by binding between ATP and a particular amino acid residue in the enzyme, and thus an intended substance is produced.

That is, for any enzyme, amino acid residues, conformation of the amino acid residues, or metal ions forming three-dimensional complexes with the amino acid residues are important, and they express the activity of an enzyme. The biocatalyst solvent of the present invention enables, by means of its structural features, protection of amino acid residues or metal ions that form complexes, and retention of the activity of the biocatalyst.

Furthermore, the biocatalyst solvent of the present invention can suppress denaturation caused by heat, among various causes of denaturation such as heat (temperature) and pH. Hydrogen bonds between amino acid residues are broken by heat, the conformation is destroyed, and the enzyme is denatured. However, the biocatalyst solvent of the present invention retains the conformation more strongly by forming a network of hydrogen bonds between the amino acid residues inside the enzyme and the hydrogen-bondable functional groups in the ionic liquid, and thus suppresses thermal denaturation. That is, the biocatalyst solvent of the present invention can retain the activity, dissolve and store an enzyme at a high enzyme concentration for a long time period, even under the conditions at room temperature (25° C.), which is higher than −20° C. to 5° C., which constitutes a general enzyme preservation condition, and under accelerating conditions at 40° C. at which enzymes are deactivated.

The biocatalyst solvent of the present invention can retain high dissolubility for a biocatalyst and the activity of the biocatalyst even under high temperature conditions. Therefore, the biocatalyst solvent is highly useful not only for the preservation of a biocatalyst, but also as an efficient reaction solvent for a biocatalysis reaction.

The biocatalyst solution of the present invention includes the biocatalyst solvent of the present invention, and when used as a biocatalyst solution, the biocatalyst solvent of the present invention is highly hydrophilic due to the structural features and has high affinity for biocatalysts. Therefore, the biocatalyst solvent of the present invention can be used alone, or as a mixture with another solvent component such as water or a polar solvent. Furthermore, the biocatalyst solvent can also be used after adding additives thereto.

Preservation of a biocatalyst according to the present invention is not particularly limited; however, preservation primarily means that the following conditions are satisfied.

The catalytic activity retention ratio for the biocatalyst solution of the present invention may vary depending on the type of the biocatalyst or the like; however, for example, when urease is dissolved at 30.0 to 50.0 mg/mL, in a case in which the solution is stored at a temperature of 25° C., the catalytic activity retention ratio after 30 days can be maintained to be 90% or higher, to be 40% or higher after 90 days, and to be 7% or higher after 180 days. In a case in which the solution is stored at 40° C. in an acceleration test, the catalytic activity retention ratio after 30 days can be maintained to be 60% or higher, and to be 13% or higher after 90 days. When catalase is dissolved at 20.0 to 50.0 mg/mL, in a case in which the solution is stored at a temperature of 25° C., the catalytic activity retention ratio after 30 days can be maintained to be 90% or higher, and to be 68% or higher after 90 days. In a case in which the solution is stored at 40° C. in an acceleration test, the catalytic activity retention ratio after 30 days can be maintained to be 90% or higher, and to be 29% or higher after 90 days. A biocatalyst solution of urease or catalase can dissolve the biocatalyst at a high concentration of 20.0 mg/mL or higher; however, even at such a high concentration, long-term storage at a high catalytic activity retention ratio such as described above is also enabled. When amylase is dissolved at 0.5 to 2.0 mg/mL, in a case in which the solution is stored at a temperature of 25° C., the catalytic activity retention ratio after 7 days can be maintained to be 90% or higher, and to be 45% or higher after 21 days. In a case in which the solution is stored at 40° C. in an acceleration test, the catalytic activity retention ratio after 7 days can be maintained to be 90% or higher, and to be 15% or higher after 21 days. When citrate synthase is dissolved at 5.0 to 10.0 mg/mL, in a case in which the solution is stored at a temperature of 25° C., the catalytic activity retention ratio after 7 days can be maintained to be 80% or higher, and to be 11% or higher after 21 days. In a case in which the solution is stored at 40° C. in an acceleration test, the catalytic activity retention ratio after 7 days can be maintained to be 45% or higher, and to be 15% or higher after 14 days. When hexokinase is dissolved at 10.0 to 65.0 mg/mL, in a case in which the solution is stored at a temperature 25° C., the catalytic activity retention ratio after 21 days can be maintained to be 10% or higher, and in a case in which the solution is stored at 40° C. in an acceleration test, the catalytic activity retention ratio after 14 days can be maintained to be 19% or higher. When alginate lyase is dissolved at 10.0 to 30.0 mg/mL, in a case in which the solution is stored at a temperature 25° C., the catalytic activity retention ratio after 60 days can be maintained to be 20% or higher, and in a case in which the solution is stored at 40° C. in an acceleration test, the catalytic activity retention ratio after 30 days can be maintained to be 13% or higher. When phosphoglucose isomerase is dissolved at 1.5 mg/mL, in a case in which the solution is stored at a temperature of 25° C., the catalytic activity retention ratio after 60 days can be maintained to be 61% or higher, and in a case in which the solution is stored at 40° C. in an acceleration test, the catalytic activity retention ratio after 21 days can be maintained to be 10% or higher. When acetyl-CoA synthetase is dissolved at 1.5 mg/mL, in a case in which the solution is stored at a temperature of 25° C., the catalytic activity retention ratio after 60 days can be maintained to be 10% or higher, and in a case in which the solution is stored at 40° C. in an acceleration test, the catalytic activity retention ratio after 14 days can be maintained to be 21% or higher. When cytochrome P450 is dissolved at 1.0 mg/mL, in a case in which the solution is stored at a temperature of 3° C., the catalytic activity retention ratio after 14 days can be maintained to be 7% or higher. Here, retention of the conformation and catalytic activity of a biocatalyst can be checked by the presence or absence of the catalytic reaction.

The storage concentration of the biocatalyst in the biocatalyst solution of the present invention may vary depending on the type of the biocatalyst or the like; however, for example, the storage concentration can be adjusted to 10 ng/mL or higher for urease, 20 mg/mL or higher for catalase, 0.5 mg/mL or higher for amylase, 5 mg/mL or higher for citrate synthase, 10 mg/mL or higher for alginate lyase, 1.5 mg/mL or higher for phosphoglucose isomerase and acetyl-CoA synthetase, 10 mg/mL or higher for hexokinase, and 1.0 mg/mL or higher for cytochrome P450.

The storage period for a biocatalyst may vary depending on the type of the biocatalyst or the like; however, the storage period can be set to, for example, 30 days or longer, more desirably 60 days or longer, even more desirably 90 days or longer, or still more desirably 180 days or longer.

Regarding the storage temperature for a biocatalyst, the biocatalyst solution of the present invention can preserve a biocatalyst in a liquid form while maintaining the activity for a long time period, for example, at a temperature in the range of 40° C. or lower.

EXAMPLES

Hereinafter, the present invention will be described in more detail by way of Examples; however, the present invention is not intended to be limited to these Examples.

<Example 1> Compound 1

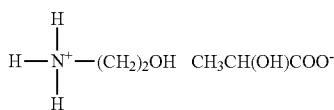

[Chemical Formula 3]

Monoethanolamine (10.00 g, 0.16 mol) was reacted with lactic acid (14.74 g, 0.16 mol) in water (100 mL) at room temperature for 3 hours, subsequently water was distilled off under reduced pressure, and the residue was washed. Thus, compound 1 was obtained.

FT-IR (KBr): 3392 cm$^{-1}$: O—H stretching vibration 2950 cm$^{-1}$: C—H stretching vibration 1579 cm$^{-1}$: COO$^-$ stretching vibration.

$^1$H-NMR (D$_2$O 400 MHz): δ 1.24 (d, 3H, C$\underline{H}_3$CH), δ 3.01 (t, 2H, N$^+$C$\underline{H}_2$CH$_2$OH), δ 3.71 (t, 2H, N$^+$CH$_2$C$\underline{H}_2$OH), δ 4.00 (m, 1H, CH$_3$C$\underline{H}$(OH)COO$^-$).

$^{13}$C-NMR (D$_2$O 100 MHz): δ 20.1 ($\underline{C}$H$_3$), δ 41.4 (N$^+$$\underline{C}$H$_2$CH$_2$OH), δ 58.3 (N$^+$CH$_2$$\underline{C}$H$_2$OH), δ 68.5 (CH$_3$$\underline{C}$H(OH)COO$^-$), δ 182.5 (CH$_3$CH(OH)$\underline{C}$OO$^-$).

<Example 2> Compound 2

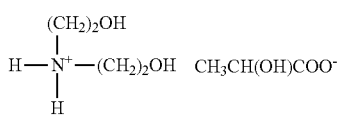

[Chemical Formula 4]

Compound 2 was obtained by the same synthesis method and mixing ratio as those used in Example 1, using diethanolamine and lactic acid.

FT-IR (KBr): 3392 cm$^{-1}$: O—H stretching vibration 2950 cm$^{-1}$: C—H stretching vibration 1584 cm$^{-1}$: COO$^-$ stretching vibration.

$^1$H-NMR (D$_2$O 400 MHz): δ 1.26 (d, 3H, C$\underline{H}_3$CH), δ 3.13 (t, 4H, N$^+$C$\underline{H}_2$CH$_2$OH), δ 3.79 (t, 4H, N$^+$CH$_2$C$\underline{H}_2$OH), 04.02 (m, 1H, CH$_3$C$\underline{H}$(OH)COO$^-$).

$^{13}$C-NMR (D$_2$O 100 MHz): δ 20.1 ($\underline{C}$H$_3$), δ 49.0 (N$^+$$\underline{C}$H$_2$CH$_2$OH), δ 56.9 (N$^+$CH$_2$$\underline{C}$H$_2$OH), δ 68.5 (CH$_3$$\underline{C}$H(OH)COO$^-$), δ 182.5 (CH$_3$CH(OH)$\underline{C}$OO$^-$).

<Example 3> Compound 3

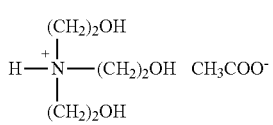

[Chemical Formula 5]

Compound 3 was obtained by the same synthesis method and mixing ratio as those used in Example 1, using triethanolamine and acetic acid.

FT-IR (KBr): 3360 cm$^{-1}$: O—H stretching vibration 2950 cm$^{-1}$: C—H stretching vibration 1558 cm$^{-1}$: COO$^-$ stretching vibration.

$^1$H-NMR (D$_2$O 400 MHz): δ 1.84 (s, 3H, C$\underline{H}_3$COO$^-$), δ 3.31 (t, 6H, N$^+$C$\underline{H}_2$CH$_2$OH), δ 3.85 (t, 6H, N$^+$CH$_2$C$\underline{H}_2$OH).

$^{13}$C-NMR (D$_2$O 100 MHz): δ 23.3 ($\underline{C}$H$_3$COO$^-$), δ 55.4 (N$^+$$\underline{C}$H$_2$CH$_2$OH), δ 55.6 (N$^+$CH$_2$$\underline{C}$H$_2$OH), δ 181.4 (CH$_3$$\underline{C}$OO$^-$).

<Example 4> Compound 4

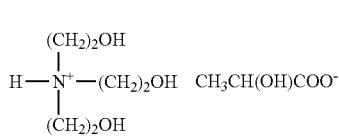

[Chemical Formula 6]

Compound 4 was obtained by the same synthesis method and mixing ratio as those used in Example 1, using triethanolamine and lactic acid.

FT-IR (KBr): 3313 cm$^{-1}$: O—H stretching vibration 2939 cm$^{-1}$: C—H stretching vibration 1591 cm$^{-1}$: COO$^-$ stretching vibration.

$^1$H-NMR (D$_2$O 400 MHz): δ 1.25 (d, 3H, C$\underline{H}_3$CH), δ 3.32 (t, 6H, N$^+$C$\underline{H}_2$CH$_2$OH), δ 3.86 (t, 6H, N$^+$C$\underline{H}_2$CH$_2$OH), δ 4.01 (m, 1H, CH$_3$C$\underline{H}$(OH)COO$^-$).

$^{13}$C-NMR (D$_2$O 100 MHz): δ 20.1 ($\underline{C}$H$_3$CH), δ 55.4 (N$^+$$\underline{C}$H$_2$CH$_2$OH), δ 55.6 (N$^+$CH$_2$$\underline{C}$H$_2$OH), δ 68.5 (CH$_3$$\underline{C}$H(OH)COO$^-$), δ 182.5 (CH$_3$CH(OH)$\underline{C}$OO$^-$).

<Example 5> Compound 5

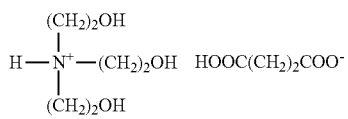

[Chemical Formula 7]

Compound 5 was obtained by the same synthesis method and mixing ratio as those used in Example 1, using triethanolamine and succinic acid.

FT-IR (KBr): 3360 m$^{-1}$: O—H stretching vibration 2939 cm$^{-1}$: C—H stretching vibration 1714 cm$^{-1}$: COOH stretching vibration 1563 cm$^{-1}$: COO$^-$ stretching vibration.

$^1$H-NMR (D$_2$O 400 MHz): δ 2.51 (s, 4H, HOOCC$\underline{H}_2$C$\underline{H}_2$COO$^-$), δ 3.22 (t, 6H, N$^+$C$\underline{H}_2$ CH$_2$OH), δ 3.84 (t, 6H, N$^+$CH$_2$C$\underline{H}_2$ OH).

$^{13}$C-NMR (D$_2$O 100 MHz): δ 31.4 (HOOC$\underline{C}$H$_2$ $\underline{C}$H$_2$COO$^-$), δ 48.9 (N$^+$$\underline{C}$H$_2$CH$_2$OH), δ 56.5 (N$^+$CH$_2$ $\underline{C}$H$_2$OH), δ 179.7 ($\underline{C}$OOH, $\underline{C}$OO$^-$).

<Example 6> Compound 6

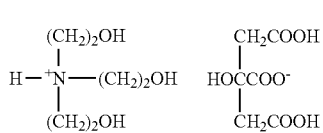

[Chemical Formula 8]

Compound 6 was obtained by the same synthesis method and mixing ratio as those used in Example 1, using triethanolamine and citric acid.

FT-IR (KBr): 3313 cm$^{-1}$: O—H stretching vibration 2939 cm$^{-1}$: C—H stretching vibration 1717 cm$^{-1}$: COOH stretching vibration 1588 cm$^{-1}$: COO$^-$ stretching vibration.

$^1$H-NMR (D$_2$O 400 MHz): δ 2.63 (m, 4H, HOOCCH$_2$C(OH)(COO$^-$)CH$_2$COOH), δ 3.37 (t, 6H, N$^+$CH$_2$CH$_2$OH), δ 3.84 (t, 6H, N$^+$CH$_2$CH$_2$OH).

$^{13}$C-NMR (D$_2$O 100 MHz): δ 43.7 (HOOCCH$_2$C(OH)(COO$^-$)CH$_2$COOH), δ 55.0 (N$^+$CH$_2$CH$_2$OH), δ 55.3 (N$^+$CH$_2$CH$_2$OH), δ 73.8 (HOOCCH$_2$C(OH)(COO$^-$)CH$_2$COOH), δ 174.8 (HOOCCH$_2$C(OH)(COO$^-$)CH$_2$COOH), δ 178.7 (HOOCCH$_2$C(OH)(COO$^-$)CH$_2$COOH).

<Example 7> Compound 7

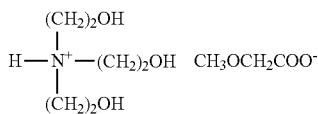

[Chemical Formula 9]

Compound 7 was obtained by the same synthesis method and mixing ratio as those used in Example 1, using triethanolamine and methoxyacetic acid.

FT-IR (KBr): 3312 cm$^{-1}$: O—H stretching vibration 2950 cm$^{-1}$: C—H stretching vibration 1593 cm$^{-1}$: COO$^-$ stretching vibration.

$^1$H-NMR (D$_2$O 400 MHz): δ 3.28 (t, 3H, CH$_3$OCH$_2$COO$^-$), δ 3.39 (t, 6H, N$^+$CH$_2$CH$_2$OH), δ 3.78 (s, 2H, CH$_3$OCH$_2$COO$^-$), δ 3.87 (t, 6H, N$^+$CH$_2$CH$_2$OH).

$^{13}$C-NMR (D$_2$O 100 MHz): δ 55.1 (N$^+$CH$_2$CH$_2$OH), δ 55.3 (N$^+$CH$_2$CH$_2$OH), δ 58.1 (CH$_3$OCH$_2$COO$^-$), δ 71.2 (CH$_3$OCH$_2$COO$^-$), δ 178.0 (CH$_3$OCH$_2$COO$^-$).

<Example 8> Compound 8

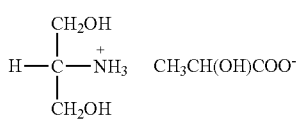

[Chemical Formula 10]

Compound 8 was obtained by the same synthesis method and mixing ratio as those used in Example 1, using 2-amino-1,3-propanediol and lactic acid.

FT-IR (KBr): 3231 cm$^{-1}$: O—H stretching vibration 2972 cm$^{-1}$: C—H stretching vibration 1571 cm$^{-1}$: COO$^-$ stretching vibration.

$^1$H-NMR (D$_2$O 400 MHz): δ 1.17-1.24 (m, 3H, CH$_3$CH(OH)COO$^-$), δ 3.22-3.27 (m, 1H, CH$_3$CH(OH)COO$^-$), δ 3.55-3.71 (m, 1H, HOCH$_2$CH(N$^+$H$_3$)CH$_2$OH), δ 3.97-4.02 (m, 4H, HOCH$_2$CH(N$^+$H$_3$)CH$_2$OH).

$^{13}$C-NMR (D$_2$O 100 MHz): δ 20.0 (CH$_3$CH(OH)COO$^-$), δ 53.9 (HOCH$_2$CH(N$^+$H$_3$)CH$_2$OH), δ 59.3 (HOCH$_2$CH(N$^+$H$_3$)CH$_2$OH), δ 68.4 (CH$_3$CH(OH)COO$^-$), δ 182.4 (CH$_3$CH(OH)COO$^-$).

<Example 9> Compound 9

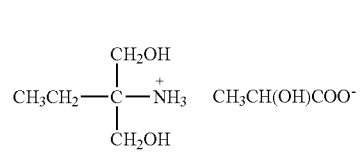

[Chemical Formula 11]

Compound 9 was obtained by the same synthesis method and mixing ratio as those used in Example 1, using 2-amino-2-ethyl-1,3-propanediol and lactic acid.

FT-IR (KBr): 3231 cm$^{-1}$: O—H stretching vibration 2937 cm$^{-1}$: C—H stretching vibration 1571 cm$^{-1}$: COO$^-$ stretching vibration.

$^1$H-NMR (D$_2$O 400 MHz): δ 0.77-0.81 (m, 3H, NH$_3^+$C(CH$_2$OH)$_2$CH$_2$CH$_3$), δ 1.17-1.24 (m, 3H, CH$_3$CH(OH)COO$^-$), δ 1.51-1.57 (m, 2H, NH$_3^+$C(CH$_2$OH)$_2$CH$_2$CH$_3$), δ 3.52 (s, 4H, NH$_3^+$C(CH$_2$OH)$_2$CH$_2$CH$_3$), δ 3.94-3.99 (m, 1H, CH$_3$CH(OH)COO$^-$).

$^{13}$C-NMR (D$_2$O 100 MHz): δ 6.3 (NH$_3^+$C(CH$_2$OH)$_2$CH$_2$CH$_3$), δ 20.0 (CH$_3$CH(OH)COO$^-$), δ 23.5 (NH$_3^+$C(CH$_2$OH)$_2$CH$_2$CH$_3$), δ 60.3 (NH$_3^+$C(CH$_2$OH)$_2$CH$_2$CH$_3$), δ 61.0 (NH$_3^+$C(CH$_2$OH)$_2$CH$_2$CH$_3$), δ 68.5 (CH$_3$CH(OH)COO$^-$), δ 182.4 (CH$_3$CH(OH)COO$^-$).

<Example 10> Compound 10

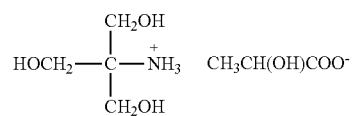

[Chemical Formula 12]

Compound 10 was obtained by the same synthesis method and mixing ratio as those used in Example 1, using tris(hydroxymethyl)aminomethane and lactic acid.

FT-IR (KBr): 3228 cm$^{-1}$: O—H stretching vibration 2935 cm$^{-1}$: C—H stretching vibration 1571 cm$^{-1}$: COO$^-$ stretching vibration.

$^1$H-NMR (D$_2$O 400 MHz): δ 1.15-1.17 (m, 3H, CH$_3$CH(OH)COO$^-$), δ 3.53 (s, 6H, NH$_3^+$C(CH$_2$OH)$_3$), δ 3.91-4.11 (m, 1H, CH$_3$CH(OH)COO$^-$).

$^{13}$C-NMR (D$_2$O 100 MHz): δ 20.0 (CH$_3$CH(OH)COO$^-$), δ 59.8 (NH$_3^+$C(CH$_2$OH)$_3$), δ 60.7 (NH$_3^+$C(CH$_2$OH)$_3$), δ 68.4 (CH$_3$CH(OH)COO$^-$), δ 182.4 (CH$_3$CH(OH)COO$^-$).

<Example 11> Compound 11

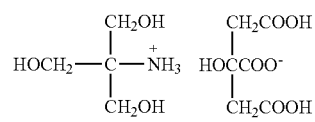

[Chemical Formula 13]

Compound 11 was obtained by the same synthesis method and mixing ratio as those used in Example 1, using tris(hydroxymethyl)aminomethane and citric acid.

FT-IR (KBr): 3145 cm$^{-1}$: O—H stretching vibration 2946 cm$^{-1}$: C—H stretching vibration 1711 cm$^{-1}$: COOH stretching vibration 1572 cm$^{-1}$: COO$^-$ stretching vibration.

$^1$H-NMR (D$_2$O 400 MHz): δ 2.58-2.75 (m, 4H, HOOCC$\underline{H}_2$C(OH)(COO$^-$)C$\underline{H}_2$COOH), δ 3.57 (s, 6H, NH$_3^+$C(C$\underline{H}_2$OH)$_3$).

$^{13}$C-NMR (D$_2$O 100 MHz): δ 43.7 (HOOC$\underline{C}$H$_2$C(OH)(COO$^-$)$\underline{C}$H$_2$COOH), δ 59.2 (NH$_3^+$$\underline{C}$(CH$_2$OH)$_3$), δ 61.4 (NH$_3^+$C($\underline{C}$H$_2$OH)$_3$), δ 73.8 (HOOCCH$_2$$\underline{C}$(OH)(COO$^-$)CH$_2$COOH), δ 174.8 (HOO$\underline{C}$CH$_2$C(OH)(COO$^-$)CH$_2\underline{C}$OOH), δ 178.6 (HOOCCH$_2$C(OH)($\underline{C}$OO$^-$)CH$_2$COOH).

<Example 12> Compound 12

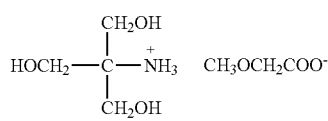

[Chemical Formula 14]

Compound 12 was obtained by the same synthesis method and mixing ratio as those used in Example 1, using tris(hydroxymethyl)aminomethane and methoxyacetic acid.

FT-IR (KBr): 3148 cm$^{-1}$: O—H stretching vibration 2928 cm$^{-1}$: C—H stretching vibration 1574 cm$^{-1}$: COO$^-$ stretching vibration.

$^1$H-NMR (D$_2$O 400 MHz): δ 0.95 (t, 3H, C$\underline{H}_3$OCH$_2$COO$^-$), δ 3.48 (s, 6H, NH$_3^+$C(C$\underline{H}_2$OH)$_3$), δ 3.66 (s, 2H, CH$_3$OC$\underline{H}_2$COO$^-$).

$^{13}$C-NMR (D$_2$O 100 MHz): δ 14.0 ($\underline{C}$H$_3$O), δ 59.2 (NH$_3^+$$\underline{C}$(CH$_2$OH)$_3$), δ 61.3 (NH$_3^+$C($\underline{C}$H$_2$OH)$_3$), δ 69.1 (CH$_3$O$\underline{C}$H$_2$COO$^-$), δ 178.1 (CH$_3$OCH$_2\underline{C}$OO$^-$).

<Example 13> Compound 13

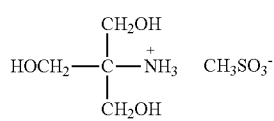

[Chemical Formula 15]

Compound 13 was obtained by the same synthesis method and mixing ratio as those used in Example 1, using tris(hydroxymethyl)aminomethane and methanesulfonic acid.

FT-IR (KBr): 3388 cm$^{-1}$: O—H stretching vibration 2959 cm$^{-1}$: C—H stretching vibration.

$^1$H-NMR (D$_2$O 400 MHz): δ 2.72 (s, 3H, C$\underline{H}_3$SO$_3^-$), δ 3.65 (s, 6H, NH$_3^+$C(C$\underline{H}_2$OH)$_3$).

$^{13}$C-NMR (D$_2$O 100 MHz): δ 38.5 ($\underline{C}$H$_3$SO$_3^-$), δ 59.4 (NH$_3^+$$\underline{C}$(CH$_2$OH)$_3$), δ 61.4 (NH$_3^+$C($\underline{C}$H$_2$OH)$_3$).

<Example 14> Compound 14

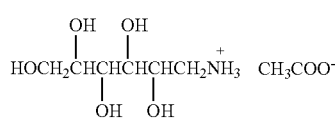

[Chemical Formula 16]

Compound 14 was obtained by the same synthesis method and mixing ratio as those used in Example 1, using D-glucamine and acetic acid.

FT-IR (KBr): 3152 cm$^{-1}$: O—H stretching vibration 2921 cm$^{-1}$: C—H stretching vibration 1549 cm$^{-1}$: COO$^-$ stretching vibration.

$^1$H-NMR (D$_2$O 400 MHz): δ 1.76 (s, 3H, C$\underline{H}_3$COO$^-$), δ 2.89-3.09 (m, 2H, HOCH$_2$(CH(OH))$_3$CH(OH)C$\underline{H}_2$NH$_3^+$), δ 3.47-3.68 (m, 5H, HOC$\underline{H}_2$(C$\underline{H}$(OH))$_3$CH(OH)CH$_2$NH$_3^+$), δ 3.86-3.90 (m, 1H, HOCH$_2$(CH(OH))$_3$C$\underline{H}$(OH)CH$_2$NH$_3^+$).

$^{13}$C-NMR (D$_2$O 100 MHz): δ 23.2 ($\underline{C}$H$_3$COO$^-$), δ 41.6 (HOCH$_2$(CH(OH))$_3$CH(OH)$\underline{C}$H$_2$NH$_3^+$), δ 62.6 (HO$\underline{C}$H$_2$(CH(OH))$_3$CH(OH)CH$_2$NH$_3^+$), δ 68.9-70.8 (HOCH$_2$($\underline{C}$H(OH))$_3$CH(OH)CH$_2$NH$_3^+$), δ 181.4 (CH$_3\underline{C}$OO$^-$).

<Example 15> Compound 15

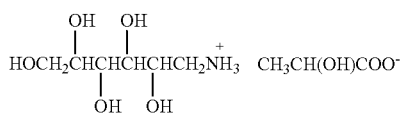

[Chemical Formula 17]

Compound 15 was obtained by the same synthesis method and mixing ratio as those used in Example 1, using D-glucamine and lactic acid.

FT-IR (KBr): 3234 cm$^{-1}$: O—H stretching vibration 2926 cm$^{-1}$: C—H stretching vibration 1572 cm$^{-1}$: COO$^-$ stretching vibration.

$^1$H-NMR (D$_2$O 400 MHz): δ 1.14 (m, 3H, C$\underline{H}_3$CH(OH)COO$^-$), δ 2.83-3.02 (m, 2H, HOCH$_2$(CH(OH))$_3$CH(OH)C$\underline{H}_2$NH$_3^+$), δ 3.45-3.66 (m, 5H, HOC$\underline{H}_2$(C$\underline{H}$(OH))$_3$CH(OH)CH$_2$NH$_3^+$), δ 3.81-3.85 (m, 1H, HOCH$_2$(CH(OH))$_3$C$\underline{H}$(OH)CH$_2$NH$_3^+$), δ 3.90-3.95 (m, 1H, CH$_3$C$\underline{H}$(OH)COO$^-$).

$^{13}$C-NMR (D$_2$O 100 MHz): δ 20.1 ($\underline{C}$H$_3$CH(OH)COO$^-$), δ 41.7 (HOCH$_2$(CH(OH))$_3$CH(OH)$\underline{C}$H$_2$NH$_3^+$), δ 62.6 (HO$\underline{C}$H$_2$(CH(OH))$_3$CH(OH)CH$_2$NH$_3^+$), δ 68.4 (CH$_3$$\underline{C}$H(OH)COO$^-$), δ 68.9-70.9 (HOCH$_2$($\underline{C}$H(OH))$_3$CH(OH)CH$_2$NH$_3^+$), δ 182.5 (CH$_3$CH(OH)$\underline{C}$OO$^-$).

<Example 16> Compound 16

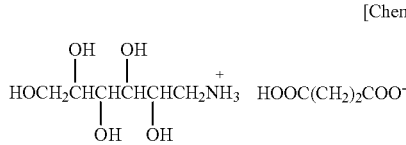

[Chemical Formula 18]

Compound 16 was obtained by the same synthesis method and mixing ratio as those used in Example 1, using D-glucamine and succinic acid.

FT-IR (KBr): 3177 cm$^{-1}$: O—H stretching vibration 2925 cm$^{-1}$: C—H stretching vibration 1709 cm$^{-1}$: COOH stretching vibration 1551 cm$^{-1}$: COO$^-$ stretching vibration.

$^1$H-NMR (D$_2$O 400 MHz): δ 2.42 (s, 4H, HOOCC$\underline{H}_2$C$\underline{H}_2$COO$^-$), δ 2.89-3.08 (m, 2H, HOCH$_2$(CH(OH))$_3$CH(OH)C$\underline{H}_2$NH$_3^+$), δ 3.46-3.67 (m, 5H, HOC$\underline{H}_2$(C$\underline{H}$(OH))$_3$CH(OH)CH$_2$NH$_3^+$), δ 3.85-3.89 (m, 1H, HOCH$_2$(CH(OH))$_3$C$\underline{H}$(OH)CH$_2$NH$_3^+$).

$^{13}$C-NMR (D$_2$O 100 MHz): δ 31.2 (HOOC$\underline{C}$H$_2$$\underline{C}$H$_2$COO$^-$), δ 41.6 (HOCH$_2$(CH(OH))$_3$CH(OH)$\underline{C}$H$_2$NH$_3$$^+$), δ 62.6 (HO$\underline{C}$H$_2$(CH(OH))$_3$CH(OH)CH$_2$NH$_3$$^+$), δ 68.9-70.8 (HOCH$_2$($\underline{C}$H(OH))$_3$$\underline{C}$H(OH)CH$_2$NH$_3$$^+$), δ 179.6 (HOO$\underline{C}$CH$_2$CH$_2$$\underline{C}$OO$^-$).

<Example 17> Compound 17

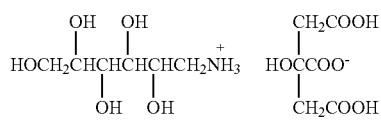
[Chemical Formula 19]

Compound 17 was obtained by the same synthesis method and mixing ratio as those used in Example 1, using D-glucamine and citric acid.

FT-IR (KBr): 3226 cm$^{-1}$: O—H stretching vibration 2931 cm$^{-1}$: C—H stretching vibration 1711 cm$^{-1}$: COOH stretching vibration 1575 cm$^{-1}$: COO$^-$ stretching vibration.

$^1$H-NMR (D$_2$O 400 MHz): δ 2.66-2.83 (m, 4H, HOOCC$\underline{H}_2$C(OH)(COO$^-$)C$\underline{H}_2$COOH), δ 2.90-3.10 (m, 2H, HOCH$_2$(CH(OH))$_3$CH(OH)C$\underline{H}_2$NH$_3$$^+$), δ 3.48-3.68 (m, 5H, HOC$\underline{H}_2$(C$\underline{H}$(OH))$_3$CH(OH)CH$_2$NH$_3$$^+$), δ 3.86-3.90 (m, 1H, HOCH$_2$(CH(OH))$_3$CH(OH)C$\underline{H}_2$NH$_3$$^+$).

$^{13}$C-NMR (D$_2$O 100 MHz): δ 41.7 (HOCH$_2$(CH(OH))$_3$CH(OH)$\underline{C}$H$_2$NH$_3$$^+$), δ 43.6 (HOOC$\underline{C}$H$_2$C(OH)(COO$^-$)$\underline{C}$H$_2$COOH), δ 62.6 (HO$\underline{C}$H$_2$(CH(OH))$_3$CH(OH)CH$_2$NH$_3$$^+$), δ 68.9-70.8 (HOCH$_2$($\underline{C}$H(OH))$_3$$\underline{C}$H(OH)CH$_2$NH$_3$$^+$), δ 73.8 (HOOCCH$_2$$\underline{C}$(OH)(COO$^-$)CH$_2$COOH), δ 174.6 (HOO$\underline{C}$CH$_2$C(OH)(COO$^-$)CH$_2$$\underline{C}$OOH), δ 178.6 (HOOCCH$_2$C(OH)($\underline{C}$OO$^-$)CH$_2$COOH).

<Example 18> Compound 18

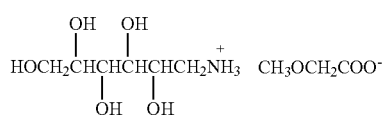
[Chemical Formula 20]

Compound 18 was obtained by the same synthesis method and mixing ratio as those used in Example 1, using D-glucamine and methoxyacetic acid.

FT-IR (KBr): 3174 cm$^{-1}$: O—H stretching vibration 2924 cm$^{-1}$: C—H stretching vibration 1577 cm$^{-1}$: COO$^-$ stretching vibration.

$^1$H-NMR (D$_2$O 400 MHz): δ 2.89-3.09 (m, 2H, HOCH$_2$(CH(OH))$_3$CH(OH)C$\underline{H}_2$NH$_3$$^+$), δ 3.20 (s, 3H, C$\underline{H}_3$OCH$_2$COO$^-$), δ 3.48-3.69 (m, 5H, HOC$\underline{H}_2$(C$\underline{H}$(OH))$_3$CH(OH)CH$_2$NH$_3$$^+$), δ 3.72 (s, 2H, CH$_3$OC$\underline{H}_2$COO$^-$), δ 3.86-3.90 (m, 1H, HOCH$_2$(CH(OH))$_3$C$\underline{H}$(OH)CH$_2$NH$_3$$^+$).

$^{13}$C-NMR (D$_2$O 100 MHz): δ 41.6 (HOCH$_2$(CH(OH))$_3$CH(OH)$\underline{C}$H$_2$NH$_3$$^+$), δ 58.0 ($\underline{C}$H$_3$OCH$_2$COO$^-$), δ 62.6 (HO$\underline{C}$H$_2$(CH(OH))$_3$CH(OH)CH$_2$NH$_3$$^+$), δ 69.0-70.8 (HOCH$_2$($\underline{C}$H(OH))$_3$$\underline{C}$H(OH)CH$_2$NH$_3$$^+$), δ 71.1 (CH$_3$O$\underline{C}$H$_2$COO$^-$), δ 178.0 (CH$_3$OCH$_2$$\underline{C}$OO$^-$).

<Example 19> Compound 19

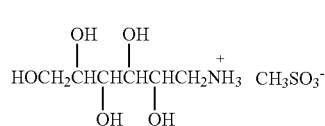
[Chemical Formula 21]

Compound 19 was obtained by the same synthesis method and mixing ratio as those used in Example 1, using D-glucamine and methanesulfonic acid.

FT-IR (KBr): 3388 cm$^{-1}$: O—H stretching vibration 2959 cm$^{-1}$: C—H stretching vibration.

$^1$H-NMR (D$_2$O 400 MHz): δ 2.71 (s, 3H, C$\underline{H}_3$SO$_3$$^-$), δ 2.95-3.15 (m, 2H, HOCH$_2$(CH(OH))$_3$CH(OH)C$\underline{H}_2$NH$_3$$^+$), δ 3.53-3.73 (m, 5H, HOC$\underline{H}_2$(C$\underline{H}$(OH))$_3$CH(OH)CH$_2$NH$_3$$^+$), δ 3.90-3.96 (m, 1H, HOCH$_2$(CH(OH))$_3$C$\underline{H}$(OH)CH$_2$NH$_3$$^+$).

$^{13}$C-NMR (D$_2$O 100 MHz): δ 38.5 ($\underline{C}$H$_3$SO$_3$$^-$), δ 41.7 (HOCH$_2$(CH(OH))$_3$CH(OH)$\underline{C}$H$_2$NH$_3$$^+$), δ 62.7 (HO$\underline{C}$H$_2$(CH(OH))$_3$CH(OH)CH$_2$NH$_3$$^+$), δ 68.9-70.9 (HOCH$_2$($\underline{C}$H(OH))$_3$$\underline{C}$H(OH)CH$_2$NH$_3$$^+$).

<Example 20> Compound 20

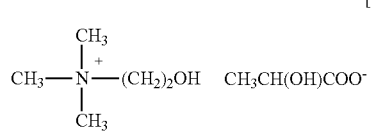
[Chemical Formula 22]

Choline chloride was dissolved in ion-exchanged water, and the solution was passed through a column packed with an OH type ion exchange resin (DIAION SA10A manufactured by Mitsubishi Chemical Corp.). Thus, choline hydroxide was obtained. The choline hydroxide (8.68 g, 0.07 mol) thus obtained was reacted with lactic acid (6.45 g, 0.07 mol) in water (100 mL) for 3 hours at room temperature, subsequently water was distilled off under reduced pressure, and the residue was washed. Thus, compound 20 was obtained.

FT-IR (KBr): 3464 cm$^{-1}$: O—H stretching vibration 2920 cm$^{-1}$: C—H stretching vibration 1570 cm$^{-1}$: COO$^-$ stretching vibration.

$^1$H-NMR (D$_2$O 400 MHz): δ 1.30 (m, 3H, C$\underline{H}_3$CH(OH)COO$^-$), δ 3.07 (s, 9H, C$\underline{H}_3$N$^+$), δ 3.38 (m, 2H, C$\underline{H}_2$N$^+$), δ 3.92 (m, 2H, N$^+$CH$_2$C$\underline{H}_2$OH), δ 3.96 (m, 1H, CH$_3$C$\underline{H}$).

$^{13}$C-NMR (D$_2$O 100 MHz): δ 20.1 ($\underline{C}$H$_3$CH(OH)COO$^-$), δ 53.9 ($\underline{C}$H$_3$N$^+$), δ 55.6 ($\underline{C}$H$_2$N$^+$), δ 68.4 (N$^+$$\underline{C}$H$_2$CH$_2$OH), δ 72.8 (CH$_3$$\underline{C}$H(OH)COO$^-$), δ 182.3 (CH$_3$CH(OH)$\underline{C}$OO$^-$).

<Example 21> Compound 21

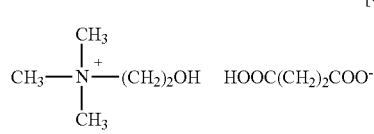
[Chemical Formula 23]

Compound 21 was obtained by the same synthesis method and mixing ratio as those used in Example 20, using choline chloride and succinic acid.

FT-IR (KBr): 3177 $cm^{-1}$: O—H stretching vibration 2925 $cm^{-1}$: C—H stretching vibration 1709 $cm^{-1}$: COOH stretching vibration 1551 $cm^{-1}$: $COO^-$ stretching vibration.

$^1$H-NMR ($D_2O$ 400 MHz): δ 2.43 (s, 4H, $HOOCCH_2CH_2COO^-$), δ 3.07 (s, 9H, $CH_3N^+$), δ 3.39 (m, 2H, $CH_2N^+$), δ 3.93 (m, 2H, $N^+CH_2CH_2OH$).

$^{13}$C-NMR ($D_2O$ 100 MHz): δ 30.8 ($HOOCCH_2CH_2COO^-$), δ 53.9 ($CH_3N^+$), δ 55.5 ($CH_2N^+$), δ 67.4 ($N^+CH_2CH_2OH$), δ 179.1 ($HOOCCH_2CH_2COO^-$).

<Example 22> Compound 22

[Chemical Formula 24]

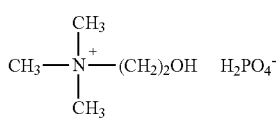

Compound 22 was obtained by the same synthesis method and mixing ratio as those used in Example 20, using choline chloride and phosphoric acid.

FT-IR (KBr): 3464 $cm^{-1}$: O—H stretching vibration 2920 $cm^{-1}$: C—H stretching vibration.

$^1$H-NMR ($D_2O$ 400 MHz): δ 3.08 (s, 9H, $CH_3N^+$), δ 3.39 (m, 2H, $CH_2N^+$), δ 3.93 (m, 2H, $N^+CH_2CH_2OH$).

$^{13}$C-NMR ($D_2O$ 100 MHz): δ 53.9 ($CH_3N^+$), δ 55.6 ($CH_2N^+$), δ 67.4 ($N^+CH_2CH_2OH$).

Examples 23 to 27

Compounds 23 to 27 were synthesized by the method described in JP 2012-31137 A.

<Example 23> Compound 23

[Chemical Formula 25]

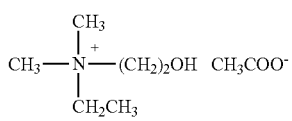

<Example 24> Compound 24

[Chemical Formula 26]

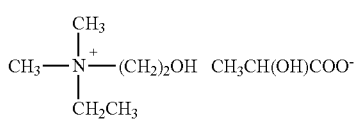

<Example 25> Compound 25

[Chemical Formula 27]

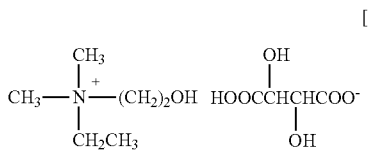

<Example 26> Compound 26

[Chemical Formula 28]

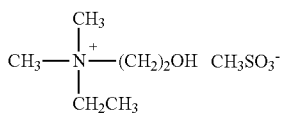

<Example 27> Compound 27

[Chemical Formula 29]

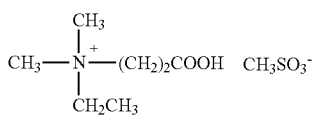

<Comparative Example 1> Compound 28: $Bu_4N^+$ $CH_3CH(OH)COO^-$

[Chemical Formula 30]

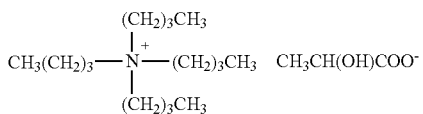

Tetrabutylammonium bromide was dissolved in ion-exchanged water, and the solution was passed through a column packed with an OH type ion exchange resin (DIAION SA10A manufactured by Mitsubishi Chemical Corp.). Thus, tetrabutylammonium hydroxide was obtained. The tetrabutylammonium hydroxide (8.05 g, 0.03 mol) thus obtained was reacted with lactic acid (2.70 g, 0.03 mmol) in water (100 mL) at room temperature for 3 hours, subsequently water was distilled off under reduced pressure, and the residue was washed. Thus, compound 28 was obtained. In regard to the characteristics at room temperature (−5° C., −10° C.), an enzyme dissolution test, and measurement of the enzyme activity retention ratio described below, evaluation was carried out by dissolving each of the compounds in a liquid 14% aqueous solution.

Comparative Examples 2 to 5

As the ionic liquid of compound 29, a reagent of Wako Pure Chemical Industries, Ltd. was used, and as the ionic liquids of compounds 30 to 32, reagents of Kanto Chemical Co., Inc. were used.

<Comparative Example 2> Compound 29: BMI-BF$_4$

[Chemical Formula 31]

CH$_3$–N$^+$(imidazole)N–(CH$_2$)$_2$CH$_3$    BF$_4^-$

<Comparative Example 3> Compound 30: EMI-TFSI

[Chemical Formula 32]

CH$_3$–N$^+$(imidazole)N–CH$_2$CH$_3$    (CF$_3$SO$_2$)$_2$N$^-$

<Comparative Example 4> Compound 31: BTMA-TFSI

[Chemical Formula 33]

CH$_3$–N$^+$(CH$_3$)(CH$_3$)–(CH$_2$)$_3$CH$_3$    (CF$_3$SO$_2$)$_2$N$^-$

<Comparative Example 5> Compound 32: BMI-PF$_6$

[Chemical Formula 34]

CH$_3$–N$^+$(imidazole)N–(CH$_2$)$_3$CH$_3$    PF$_6^-$

Comparative Examples 6 and 7

The ionic liquids of compounds 33 and 34 were synthesized by the method described in JP 2006-514832 W.

<Comparative Example 6> Compound 33: HOPMI-PF$_6$

[Chemical Formula 35]

CH$_3$–N$^+$(imidazole)N–CH$_2$CH$_2$CH$_2$OH    PF$_6^-$

<Comparative Example 7> Compound 34: DHOPMI-PF$_6$

[Chemical Formula 36]

CH$_3$–N$^+$(imidazole)N–CH$_2$CH(OH)CH$_2$OH    PF$_6^-$

<Comparative Example 8> Compound 35: Glycerin (100%)

A reagent of Wako Pure Chemical Industries, Ltd. was used.

<Comparative Example 9> Compound 36: Buffer

Regarding a buffer, in preservation tests for urease and catalase, a 10 mM aqueous solution of potassium dihydrogen phosphate having the pH adjusted using sodium hydroxide (phosphate buffer solution: urease: pH 7.5, catalase: pH 7.0) was used. Furthermore, in preservation tests for hexokinase and alginate lyase, an aqueous solution of trishydroxymethylaminomethane having the pH adjusted using hydrochloric acid (Tris buffer solution: hexokinase: 50 mM (pH 8.5), alginate lyase: 200 mM (pH 7.0)) was used. Furthermore, in a preservation test for cytochrome P450, a 100 mM aqueous solution of potassium dihydrogen phosphate having the pH adjusted to 7.4 using sodium hydroxide was used.

<Comparative Example 10> Compound 37: Aqueous Solution of Glycerin

Glycerin (Wako Pure Chemical Industries, Ltd.) was dissolved in water, and the concentration was adjusted to 10 mg/mL.

<Comparative Example 11> Compound 38: Aqueous Solution of Glucose

D(+)-glucose (Kanto Chemical Co., Inc.) was dissolved in water, and the concentration was adjusted to 10 mg/mL.

<Comparative Example 12> Compound 39: Aqueous Solution of Bovine Serum Albumin Albumin (derived from cow, general grade, pH 5.2: Nacalai Tesque, Inc.) was dissolved in water, and the concentration was adjusted to 10 mg/mL.

<Comparative Example 13> Compound 40: Aqueous Solution of Lysine

L(+)-lysine (Wako Pure Chemical Industries, Ltd.) was dissolved in water, and the concentration was adjusted to 10 mg/mL.

<Comparative Example 14> Compound 41: Aqueous Solution of Lysine and Bovine Serum Albumin A mixture of L(+)-lysine (Wako Pure Chemical Industries, Ltd.) and albumin (derived from cow, general grade, pH 5.2: Nacalai Tesque, Inc.) at a weight ratio of 54:46 was dissolved in water to prepare a 10 mg/mL aqueous solution.

<Comparative Example 15> Compound 42: Aqueous Solution of Arginine

L(+)-arginine (Wako Pure Chemical Industries, Ltd.) was dissolved in water, and the concentration was adjusted to 10 mg/mL.

<Comparative Example 16> Compound 43: 20% Glycerin Solution

Glycerin was dissolved in a 100 mM aqueous solution of potassium dihydrogen phosphate that had been adjusted to pH 7.4, to prepare a 20% solution.

The moisture contents of the ionic liquids of compounds 1 to 35, which were attributable to the moisture in the atmosphere and the process of synthesis, were measured by the Karl-Fischer method or using a differential thermal analyzer/thermogravimetric analyzer (TG/DTA). For compounds 1 to 34, evaluation of the compounds was performed by maintaining the amount of moisture constant (14%±0.5%).

Regarding the enzymes to be used as described below, as representative enzymes for the respective classes of various enzymes, urease (derived from jack bean, Wako Pure Chemical Industries, Ltd.) and α-amylase (derived from *Bacillus subtilis*, Wako Pure Chemical Industries, Ltd.) as hydrolases; catalase (derived from bovine liver, Wako Pure Chemical Industries, Ltd.) and cytochrome P450 (Human CYP3A4LR Easy CYP Bactosomes, Nosan Corp.) as oxidoreductases; citrate synthase (derived from swine heart, Sigma-Aldrich Company) and hexokinase (derived from budding yeast, Sigma-Aldrich Company) as transferases; alginate lyase (derived from Flavobacteria, Sigma-Aldrich Company) as a lyase; phosphoglucose isomerase (derived from rabbit muscles, Sigma-Aldrich Company) as an isomerase; and acetyl-CoA synthetase (derived from bread yeast, Sigma-Aldrich Company) as a ligase, were selected and used.

The following analyses and evaluations were carried out using the compounds of Examples and Comparative Examples described above.

1. Measurement of Freezing Point

Each of compounds 1 to 42 was introduced into screw tubes, and the tubes were left to stand for 24 hours in low temperature thermostats set at −5° C. and −10° C., respectively. The characteristics (liquid and solid) were checked, and the freezing point was measured (Tables 1 to 3).

As a result, compounds 36 to 42 (Comparative Examples 9 to 15) and glycerin (Comparative Example 8), which are general preservative aqueous solutions for enzymes, congealed under the conditions of temperatures higher than −5° C., while compounds 1 to 27 (Examples 1 to 27) were liquid with fluidity even at −10° C. Thus, it was found that the ionic liquids of the present invention had excellent low temperature stability.

2. Enzyme Dissolution Test

The dissolution concentrations of Compounds 1 to 35 (Examples 1 to 27 and Comparative Examples 1 to 8) for urease, α-amylase, catalase, citrate synthase, alginate lyase, phosphoglucose isomerase, acetyl-CoA synthetase, hexokinase, and cytochrome P450 were measured. Each enzyme was added to each of compounds 1 to 35 having the moisture contents indicated in Table 1 to 3, at room temperature (25° C.) and at a predetermined concentration. The enzyme and the compound were mixed, and then dissolution was judged by visual inspection (Tables 1 to 3).

The biocatalyst solvents of the present invention could dissolve urease to a concentration of 15 mg/mL or higher, catalase to a concentration of 20 mg/mL or higher, amylase to a concentration of 0.5 mg/mL or higher, citrate synthase to a concentration of 5 mg/mL or higher, alginate lyase to a concentration of 10 mg/mL or higher, phosphoglucose isomerase and acetyl-CoA synthetase to a concentration of 1.5 mg/mL or higher, hexokinase to a concentration of 10 mg/mL or higher, and cytochrome P450 to a concentration of 1.0 mg/mL or higher.

For all of the enzymes, compounds 1 to 27 (Examples 1 to 27) exhibited higher dissolubility than the dialkylimidazolium-based ionic liquids and hydroxyl group-containing imidazolium-based ionic liquids of compounds 29 to 34, and the tetraalkylammonium-based ionic liquids of compound 28, and it was confirmed that the structures of the present ionic liquids of quaternary ammonium cations having hydrogen-bondable functional groups such as a hydroxyl group, a carboxyl group and a hydrogen atom exhibit high dissolubility for enzymes. Furthermore, it was suggested that even among the ionic liquids of Examples, compounds 1 to 19 in which all of the functional groups of the cation were hydrogen-bondable functional groups, exhibited relatively higher dissolubility, and could increase the solubility of enzymes due to the existence of hydrogen-bondable functional groups (a hydroxyl group, a carboxyl group, and a hydrogen atom) of the cation, compared to compounds 20 to 27 (Examples 20 to 27) in which the cations were formed from hydrogen-bondable functional groups and alkyl groups.

On the other hand, when comparisons were made between the same cations (compound 3⇌compounds 4 to 7, compound 14⇌compounds 15 to 19, and compound 23⇌compounds 24 to 26), it was confirmed that ionic liquids in which the anions contained hydrogen-bondable functional groups (a hydroxyl group, a carboxyl group, an ether group) exhibited higher dissolubility for enzymes, and the dissolubility could be further increased by introducing hydrogen-bondable functional groups into the anions.

It was found that compound 26, rather than compound 27 having the same anion, for example, compounds 10 and 11, rather than compounds 12 and 13 having the same cations, and compound 20, rather than compounds 21 and 22, exhibited higher dissolubility, and among the hydrogen-bondable functional groups, a hydroxyl group exhibited a superior effect of increasing the dissolubility for enzymes.

Furthermore, for all of the enzymes, compounds 1 to 27 of the present invention exhibited relatively higher dissolubility compared to glycerin (100%) of compound 35 having three hydroxyl groups, and it was suggested that the compounds of the present invention having a salt structure formed from an anion and a cation had an effect of suppressing the interaction between enzyme molecules.

Furthermore, the anhydrous ionic liquid dissolution concentration for urease was measured.

First, compounds 1 to 34 shown in Tables 1 to 3 were converted to anhydrides by dehydration under reduced pressure, and the state was checked by visual inspection. The anhydrides of compounds 22 and 28 were solid at 25° C., while the other compounds 1 to 21, 23 to 27, and 29 to 34 were liquids even after being converted to anhydrides. Urease was added to each of compounds 1 to 6, 8 to 11, 13, 15, 18, 20, 23, 24, 27, 29, 33 and 34 (Examples 1 to 6, 8 to 11, 13, 15, 18, 20, 23, 24 and 27, and Comparative Examples 2, 6 and 7), which were liquid after being converted to anhydrides, at room temperature (25° C.) at a predetermined concentration, and urease was mixed with the compound. Subsequently, solubility was judged by visual inspection (Tables 1 to 3).

As a result, it was confirmed that anhydrides in which water did not exist in the system, also exhibited a similar tendency between the structure of cation and anion of the hydrous ionic liquids described above, and the dissolubility for the enzyme. That is, it was suggested that the structures of the ionic liquids of the present invention exhibited high dissolubility for enzymes, irrespective of the existence of water.

TABLE 1

$$R_4 - \overset{\underset{\displaystyle R_1}{|}}{\overset{+}{N}} - R_2$$
$$\underset{\displaystyle R_3}{|}$$

| | Compound | $R_1$ | $R_2$ | $R_3$ | $R_4$ | $X^-$ | Amount of moisture (wt %) | Freezing point (° C.) |
|---|---|---|---|---|---|---|---|---|
| Example 1 | 1 | $(CH_2)_2OH$ | H | H | H | $CH_3CH(OH)COO^-$ | 13.8 | <−10 |
| Example 2 | 2 | $(CH_2)_2OH$ | $(CH_2)_2OH$ | H | H | $CH_3CH(OH)COO^-$ | 13.9 | <−10 |
| Example 3 | 3 | $(CH_2)_2OH$ | $(CH_2)_2OH$ | $(CH_2)_2OH$ | H | $CH_3COO^-$ | 14.2 | <−10 |
| Example 4 | 4 | | | | | $CH_3CH(OH)COO^-$ | 13.9 | <−10 |
| Example 5 | 5 | | | | | $HOOC(CH_2)_2COO^-$ | 14.1 | <−10 |
| Example 6 | 6 | | | | | Citric acid | 13.8 | <−10 |
| Example 7 | 7 | | | | | $CH_3\text{—}O\text{—}CH_2COO^-$ | 14.0 | <−10 |
| Example 8 | 8 | H—C(CH$_2$OH)(CH$_2$OH)— | H | H | H | $CH_3CH(OH)COO^-$ | 14.2 | <−10 |
| Example 9 | 9 | $CH_3CH_2$—C(CH$_2$OH)(CH$_2$OH)— | H | H | H | $CH_3CH(OH)COO^-$ | 14.0 | <−10 |
| Example 10 | 10 | HOCH$_2$—C(CH$_2$OH)(CH$_2$OH)— | H | H | H | $CH_3CH(OH)COO^-$ | 14.0 | <−10 |
| Example 11 | 11 | HOCH$_2$—C(CH$_2$OH)(CH$_2$OH)— | | | | Citric acid | 13.8 | <−10 |
| Example 12 | 12 | HOCH$_2$—C(CH$_2$OH)(CH$_2$OH)— | | | | $CH_3\text{—}O\text{—}CH_2COO^-$ | 13.9 | <−10 |
| Example 13 | 13 | HOCH$_2$—C(CH$_2$OH)(CH$_2$OH)— | | | | $CH_3SO_3^-$ | 14.0 | <−10 |

| | | Solubility (mg/mL) | | | | | | | | |
|---|---|---|---|---|---|---|---|---|---|---|
| | Compound | Urease | Urease (anhydrous IL) | Catalase | Amylase | Citrate synthase | Alginate lyase | Phosphoglucose isomerase | Acetyl-CoA synthetase | Hexokinase | Cytochrome P450 |
| Example 1 | 1 | 47.5 | 35.0 | 45.0 | 1.5 | 8.0 | 30.0 | ≥1.5 | ≥1.5 | 50.0 | ≥1.0 |
| Example 2 | 2 | 47.5 | 35.0 | 45.0 | 1.5 | 8.0 | 30.0 | ≥1.5 | ≥1.5 | 50.0 | ≥1.0 |
| Example 3 | 3 | 45.0 | 20.0 | 40.0 | 1.0 | 6.0 | 20.0 | ≥1.5 | ≥1.5 | 50.0 | ≥1.0 |
| Example 4 | 4 | 50.0 | 40.0 | 50.0 | 2.0 | 10.0 | 30.0 | ≥1.5 | ≥1.5 | 65.0 | ≥1.0 |
| Example 5 | 5 | 50.0 | 30.0 | 50.0 | 1.5 | 10.0 | 25.0 | ≥1.5 | ≥1.5 | 50.0 | ≥1.0 |
| Example 6 | 6 | 50.0 | 30.0 | 45.0 | 1.5 | 10.0 | 20.0 | ≥1.5 | ≥1.5 | 50.0 | ≥1.0 |
| Example 7 | 7 | 47.5 | — | 40.0 | 1.5 | 8.0 | 20.0 | ≥1.5 | ≥1.5 | 50.0 | — |
| Example 8 | 8 | 47.5 | 40.0 | 45.0 | 2.0 | 8.0 | 25.0 | ≥1.5 | ≥1.5 | 50.0 | ≥1.0 |
| Example 9 | 9 | 47.5 | 40.0 | 45.0 | 2.0 | 8.0 | 25.0 | ≥1.5 | ≥1.5 | 50.0 | ≥1.0 |
| Example 10 | 10 | 50.0 | 40.0 | 50.0 | 2.0 | 10.0 | 30.0 | ≥1.5 | ≥1.5 | 65.0 | ≥1.0 |
| Example 11 | 11 | 50.0 | 30.0 | 45.0 | 1.5 | 10.0 | 20.0 | ≥1.5 | ≥1.5 | 50.0 | — |
| Example 12 | 12 | 47.5 | — | 40.0 | 1.5 | 8.0 | 20.0 | ≥1.5 | ≥1.5 | 50.0 | — |
| Example 13 | 13 | 50.0 | 20.0 | 40.0 | 1.0 | 5.0 | 25.0 | ≥1.5 | ≥1.5 | 50.0 | ≥1.0 |

TABLE 2

$$R_4 - \overset{\underset{\displaystyle R_1}{|}}{\underset{\underset{\displaystyle R_3}{|}}{{}^+N}} - R_2$$

| Compound | | $R_1$ | $R_2$ | $R_3$ | $R_4$ | $X^-$ | Amount of moisture (wt %) | Freezing point (° C.) |
|---|---|---|---|---|---|---|---|---|
| Example 14 | 14 | HOCH$_2$CHCHCHCHCH$_2$— with OH OH OH OH | H | H | H | CH$_3$COO$^-$ | 14.3 | <−10 |
| Example 15 | 15 | | | | | CH$_3$CH(OH)COO$^-$ | 14.1 | <−10 |
| Example 16 | 16 | | | | | HOOC(CH$_2$)$_2$COO$^-$ | 14.0 | <−10 |
| Example 17 | 17 | | | | | Citric acid | 14.0 | <−10 |
| Example 18 | 18 | | | | | CH$_3$—O—CH$_2$COO$^-$ | 14.1 | <−10 |
| Example 19 | 19 | | | | | CH$_3$SO$_3^-$ | 14.3 | <−10 |
| Example 20 | 20 | CH$_3$ | CH$_3$ | CH$_3$ | (CH$_2$)$_2$OH | CH$_3$CH(OH)COO$^-$ | 13.7 | <−10 |
| Example 21 | 21 | | | | | HOOC(CH$_2$)$_2$COO$^-$ | 13.8 | <−10 |
| Example 22 | 22 | | | | | H$_2$PO$_4^-$ | 14.0 | <−10 |
| Example 23 | 23 | CH$_3$ | CH$_3$ | CH$_3$CH$_2$ | (CH$_2$)$_2$OH | CH$_3$COO$^-$ | 13.9 | <−10 |
| Example 24 | 24 | | | | | CH$_3$CH(OH)COO$^-$ | 13.7 | <−10 |
| Example 25 | 25 | | | | | Tartaric acid | 13.9 | <−10 |
| Example 26 | 26 | | | | | CH$_3$SO$_3^-$ | 14.3 | <−10 |
| Example 27 | 27 | CH$_3$ | CH$_3$ | CH$_3$CH$_2$ | (CH$_2$)$_2$COOH | CH$_3$SO$_3^-$ | 13.8 | <−10 |

| | | Solubility (mg/mL) | | | | | | | | | |
|---|---|---|---|---|---|---|---|---|---|---|---|
| | Compound | Urease | Urease (anhydrous IL) | Catalase | Amylase | Citrate synthase | Alginate lyase | Phosphoglucose isomerase | Acetyl-CoA synthetase | Hexokinase | Cytochrome P450 |
| Example 14 | 14 | 45.0 | — | 35.0 | 1.0 | 5.0 | 20.0 | ≥1.5 | ≥1.5 | 50.0 | — |
| Example 15 | 15 | 50.0 | 40.0 | 50.0 | 2.0 | 10.0 | 30.0 | ≥1.5 | ≥1.5 | 60.0 | ≥1.0 |
| Example 16 | 16 | 50.0 | — | 45.0 | 1.5 | 10.0 | 25.0 | ≥1.5 | ≥1.5 | 50.0 | — |
| Example 17 | 17 | 50.0 | — | 47.5 | 1.5 | 10.0 | 20.0 | ≥1.5 | ≥1.5 | 50.0 | — |
| Example 18 | 18 | 47.5 | 30.0 | 42.5 | 1.5 | 10.0 | 25.0 | ≥1.5 | ≥1.5 | 50.0 | ≥1.0 |
| Example 19 | 19 | 50.0 | — | 40.0 | 1.0 | 10.0 | 25.0 | ≥1.5 | ≥1.5 | 50.0 | — |
| Example 20 | 20 | 45.0 | 30.0 | 42.5 | 1.0 | 8.0 | 20.0 | ≥1.5 | ≥1.5 | 40.0 | ≥1.0 |
| Example 21 | 21 | 45.0 | — | 40.0 | 1.0 | 8.0 | 20.0 | ≥1.5 | ≥1.5 | 10.0 | |
| Example 22 | 22 | 30.0 | — | 20.0 | 0.5 | 5.0 | 10.0 | ≥1.5 | ≥1.5 | 10.0 | ≥1.0 |
| Example 23 | 23 | 30.0 | 15.0 | 20.0 | 1.0 | 5.0 | 15.0 | ≥1.5 | ≥1.5 | 40.0 | — |
| Example 24 | 24 | 42.5 | 30.0 | 40.0 | 1.0 | 8.0 | 20.0 | ≥1.5 | ≥1.5 | 40.0 | ≥1.0 |
| Example 25 | 25 | 50.0 | — | 45.0 | 1.0 | 8.0 | 20.0 | ≥1.5 | ≥1.5 | 10.0 | — |
| Example 26 | 26 | 45.0 | — | 40.0 | 1.0 | 8.0 | 20.0 | ≥1.5 | ≥1.5 | 10.0 | — |
| Example 27 | 27 | 30.0 | 15.0 | 20.0 | 0.5 | 5.0 | 15.0 | ≥1.5 | ≥1.5 | 10.0 | — |

TABLE 3

$$R_4 - \overset{\underset{\displaystyle R_1}{|}}{\underset{\underset{\displaystyle R_3}{|}}{{}^+N}} - R_2$$

| | Compound | $R_1$ | $R_2$ | $R_3$ | $R_4$ | $X^-$ | Amount of moisture (wt %) | Freezing point (° C.) |
|---|---|---|---|---|---|---|---|---|
| Comparative Example 1 | 28 | | | | | Bu$_4$N$^+$ CH$_3$CH(OH)COO$^-$ | 14.0 | >25 |
| Comparative Example 2 | 29 | | | | | BMI-BF$_4$ | 14.0 | <−10 |
| Comparative Example 3 | 30 | | | | | EMI-TFSI | <0.1 | <−10 |
| Comparative Example 4 | 31 | | | | | BTMA-TFSI | <0.1 | <−10 |
| Comparative Example 5 | 32 | | | | | BMI-PF$_6$ | <0.1 | <−10 |
| Comparative Example 6 | 33 | | | | | HOPMI-PF$_6$ | 13.8 | <−10 |
| Comparative Example 7 | 34 | | | | | DHOPMI-PF$_6$ | 13.7 | <−10 |
| Comparative Example 8 | 35 | | | | | Glycerin (100%) | <0.1 | >−5 |
| Comparative Example 9 | 36 | | | | | Buffer | — | >−5 |
| Comparative Example 10 | 37 | | | | | Aqueous solution of glycerin | — | >−5 |
| Comparative Example 11 | 38 | | | | | Aqueous solution of glucose | — | >−5 |

TABLE 3-continued

| | Compound | | | | | |
|---|---|---|---|---|---|---|
| Comparative Example 12 | 39 | Aqueous solution of bovine serum albumin | | — | | >−5 |
| Comparative Example 13 | 40 | Aqueous solution of lysine | | — | | >−5 |
| Comparative Example 14 | 41 | Aqueous solution of lysine and bovine serum albumin | | — | | >−5 |
| Comparative Example 15 | 42 | Aqueous solution of arginine | | — | | >−5 |

| | | Solubility (mg/mL) | | | | | | | | |
|---|---|---|---|---|---|---|---|---|---|---|
| | Compound | Urease | Urease (anhydrous IL) | Catalase | Amylase | Citrate synthase | Alginate lyase | Phosphoglucose isomerase | Acetyl-CoA synthetase | Hexokinase | Cytochrome P450 |
| Comparative Example 1 | 28 | 1.0 | — | <0.1 | <0.1 | <0.1 | 1.0 | <0.1 | <0.1 | <0.1 | <1.0 |
| Comparative Example 2 | 29 | 1.0 | 1.0 | <0.1 | <0.1 | <0.1 | 1.0 | <0.1 | <0.1 | <0.1 | <1.0 |
| Comparative Example 3 | 30 | 1.0 | — | <0.1 | <0.1 | <0.1 | 1.0 | <0.1 | <0.1 | <0.1 | — |
| Comparative Example 4 | 31 | 1.0 | — | <0.1 | <0.1 | <0.1 | 1.0 | <0.1 | <0.1 | <0.1 | — |
| Comparative Example 5 | 32 | 1.0 | — | <0.1 | <0.1 | <0.1 | 1.0 | <0.1 | <0.1 | <0.1 | — |
| Comparative Example 6 | 33 | 15.0 | 10.0 | 10.0 | 0.1 | 1.0 | 2.5 | 1.0 | 1.0 | 1.0 | <1.0 |
| Comparative Example 7 | 34 | 15.0 | 10.0 | 10.0 | 0.1 | 1.0 | 5.0 | 1.0 | 1.0 | 1.0 | <1.0 |
| Comparative Example 8 | 35 | 10.0 | — | 20.0 | 0.5 | 5.0 | 5.0 | 1.0 | 1.0 | 1.0 | <1.0 |
| Comparative Example 9 | 36 | — | — | — | — | — | — | — | — | — | — |
| Comparative Example 10 | 37 | — | — | — | — | — | — | — | — | — | — |
| Comparative Example 11 | 38 | — | — | — | — | — | — | — | — | — | — |
| Comparative Example 12 | 39 | — | — | — | — | — | — | — | — | — | — |
| Comparative Example 13 | 40 | — | — | — | — | — | — | — | — | — | — |
| Comparative Example 14 | 41 | — | — | — | — | — | — | — | — | — | — |
| Comparative Example 15 | 42 | — | — | — | — | — | — | — | — | — | — |

3. Measurement of Enzyme Activity Retention Ratio

Urease, catalase, α-amylase, citrate synthase, hexokinase, alginate lyase, phosphoglucose isomerase, and acetyl-CoA synthetase were respectively dissolved in each of the compounds in Tables 4 to 32 at the enzyme concentrations described in Tables 4 to 31, and the solutions were left to stand in thermostats set at 25° C., which was higher than the temperatures at which enzymes are generally dissolved and the enzyme activity is retained, and under the conditions of 40° C. as a high temperature condition and as an acceleration test for stability. Furthermore, cytochrome P450 having particularly low stability was dissolved at the enzyme concentration described in Table 32, and the solution was left to stand in a thermostat set under the conditions of 3° C., which was higher than the temperature at which the activity of cytochrome P450 is generally retained.

In regard to the set concentrations, regarding compounds 1 to 34, the concentration was set to the maximum dissolubility concentration of each compound for each enzyme. Regarding compounds 35 to 42 of Comparative Examples, the concentration was set to the lowest value among the maximum dissolubility concentrations of compounds 1 to 27 (Examples 1 to 27) for each enzyme, and relatively mild conditions were employed. After being left to stand for a predetermined time period, samples thereof were collected, and the activity retention ratio for the enzyme dissolved in each of the compounds was measured using the method described below. Thus, the conformation retainability and stabilizing effect of each compound for the enzymes were checked.

<Activity Analysis for Hydrolase: Urease: Tables 4 to 9>

Urease activity was analyzed by quantitatively determining the amount of ammonium ions produced by decomposition of urea as a result of an enzymatic reaction of urease, according to an indophenol method.

First, 100 mL of a 1 mM substrate solution (prepared by dissolving urea that serves as a substrate in a 10 mM phosphate buffer solution at pH 7.5) was introduced into a conical flask, and the substrate solution was preliminarily warmed to 30° C. for about 30 minutes.

Next, the samples that had been left to stand at the set concentrations and temperatures described in Tables 4 to 9 for a predetermined period (Compounds 1 to 6, 8 to 11, 13, 15, 18, 20, 22 to 24, 27 to 29, and 33 to 42) were each added to the substrate solution described above such that the amount of enzyme would be 0.5 mg, and the mixtures were allowed to react for 60 minutes at 30° C.

After the reaction, 0.1 mL of each reaction solution was collected, and 2 mL of a phenol solution (prepared by dissolving 10 g of phenol and 50 mg of sodium pentacyanonitrosyl ferrate(III) in ion-exchanged water, and then diluting the solution in a measuring cylinder up to 1,000 mL with ion-exchanged water) and 2 mL of a sodium hypochlorite solution (prepared by dissolving 5 g of sodium hydroxide and 8.4 mL of a 5% sodium hypochlorite solution in ion-exchanged water, and then diluting the solution in a measuring cylinder up to 1,000 mL with ion-exchanged water) were immediately added to the reaction solution. The mixture was allowed to react for 20 minutes in a thermostatic chamber at 37° C.

The amount of ammonium ions produced was determined from the amount of indophenol obtained by measuring the absorbance of this reaction solution at a wavelength of 635 nm (V-550: JASCO Corp.), and thus the urease activity was calculated. Quantitative determination of ammonium ions was carried out using a calibration curve obtained by preparing ammonium ion solutions in the concentration range of 0.1 to 3.0 mM, and quantitatively determining the amounts of ammonium ions by the indophenol method as described above.

Meanwhile, the value of enzyme activity that served as a reference for the enzyme activity retention ratio was calculated as follows. A urease powder that had been preserved at an appropriate temperature was dissolved in a buffer (10 mM phosphate buffer solution at pH 7.5), and an enzyme solution having an enzyme concentration of 50 mg/mL was prepared. After the preparation, the solution was immediately added to the substrate solution as described above, such that the amount of enzyme would be 0.5 mg, and an enzymatic reaction was induced thereby. Subsequently, the enzyme activity retention ratio was calculated based on the amount of ammonium ions that had been quantitatively determined by the indophenol method, as a reference.

The results are presented in Tables 4 to 9.

TABLE 4

Urease: 25° C.

| | | Biocatalyst solvent $R_4-{}^+N(R_1)(R_2)(R_3)\ X^-$ | | | | | Aqueous solution concentration | Enzyme concentration (mg/mL) |
|---|---|---|---|---|---|---|---|---|
| | Compound | $R_1$ | $R_2$ | $R_3$ | $R_4$ | $X^-$ | | |
| Example 1 | 1 | $(CH_2)_2OH$ | H | H | H | $CH_3CH(OH)COO^-$ | — | 47.5 |
| Example 2 | 2 | $(CH_2)_2OH$ | $(CH_2)_2OH$ | H | H | $CH_3CH(OH)COO^-$ | — | 47.5 |
| Example 3 | 3 | $(CH_2)_2OH$ | $(CH_2)_2OH$ | $(CH_2)_2OH$ | H | $CH_3COO^-$ | — | 45 |
| Example 4 | 4 | | | | | $CH_3CH(OH)COO^-$ | — | 50 |
| Example 5 | 5 | | | | | $HOOC(CH_2)_2COO^-$ | — | 50 |
| Example 6 | 6 | | | | | Citric acid | — | 50 |
| Example 8 | 8 | $H-C(CH_2OH)(CH_2OH)-$ | H | H | H | $CH_3CH(OH)COO^-$ | — | 47.5 |
| Example 9 | 9 | $CH_3CH_2-C(CH_2OH)(CH_2OH)-$ | H | H | H | $CH_3CH(OH)COO^-$ | — | 47.5 |

| | | Enzyme activity retention ratio (%) Storage period | | | | | | | |
|---|---|---|---|---|---|---|---|---|---|
| | Compound | After 1 day | After 7 days | After 14 days | After 21 days | After 30 days | After 60 days | After 90 days | After 180 days |
| Example 1 | 1 | 99 | 98 | 97 | 93 | 93 | 83 | 83 | 25 |
| Example 2 | 2 | 96 | 96 | 96 | 95 | 95 | 82 | 82 | 26 |
| Example 3 | 3 | 97 | 96 | 95 | 95 | 93 | 93 | 93 | 29 |
| Example 4 | 4 | 98 | 99 | 98 | 97 | 95 | 96 | 90 | 25 |
| Example 5 | 5 | 99 | 98 | 98 | 97 | 94 | 84 | 84 | 25 |
| Example 6 | 6 | 99 | 97 | 95 | 97 | 93 | 82 | 82 | 30 |
| Example 8 | 8 | 96 | 96 | 96 | 96 | 95 | 83 | 83 | 27 |
| Example 9 | 9 | 98 | 98 | 98 | 95 | 93 | 82 | 82 | 25 |

TABLE 5

Urease: 25° C.

| | Compound | Biocatalyst solvent $R_4-{}^+N(R_1)(R_3)-R_2$ $X^-$ | | | | | Aqueous solution concentration | Enzyme concentration (mg/mL) |
|---|---|---|---|---|---|---|---|---|
| | | $R_1$ | $R_2$ | $R_3$ | $R_4$ | $X^-$ | | |
| Example 10 | 10 | $CH_2OH$—$C(CH_2OH)$—$CH_2OH$ (HOCH$_2$—C(CH$_2$OH)(CH$_2$OH)—) | H | H | H | $CH_3CH(OH)COO^-$ | — | 50 |
| Example 11 | 11 | | H | H | H | Citric acid | — | 50 |
| Example 13 | 13 | | H | H | H | $CH_3SO_3^-$ | — | 50 |
| Example 15 | 15 | HOCH$_2$CHCHCHCH$_2$— (with OH groups) | H | H | H | $CH_3CH(OH)COO^-$ | — | 50 |
| Example 18 | 18 | | H | H | H | $CH_3$—O—$CH_2COO^-$ | — | 47.5 |
| Example 20 | 20 | $CH_3$ | $CH_3$ | $CH_3$ | $(CH_2)_2OH$ | $CH_3CH(OH)COO^-$ | — | 45 |
| Example 22 | 22 | | | | | $H_2PO_4^-$ | — | 30 |
| Example 23 | 23 | $CH_3$ | $CH_3$ | $CH_3CH_2$ | $(CH_2)_2OH$ | $CH_3COO^-$ | — | 30 |
| Example 24 | 24 | | | | | $CH_3CH(OH)COO^-$ | — | 42.5 |
| Example 27 | 27 | $CH_3$ | $CH_3$ | $CH_3CH_2$ | $(CH_2)_2COOH$ | $CH_3SO_3^-$ | — | 30 |

| | Compound | Enzyme activity retention ratio (%) Storage period | | | | | | | |
|---|---|---|---|---|---|---|---|---|---|
| | | After 1 day | After 7 days | After 14 days | After 21 days | After 30 days | After 60 days | After 90 days | After 180 days |
| Example 10 | 10 | 98 | 100 | 98 | 96 | 94 | 93 | 90 | 27 |
| Example 11 | 11 | 97 | 97 | 96 | 94 | 92 | 86 | 80 | 25 |
| Example 13 | 13 | 98 | 97 | 95 | 95 | 93 | 84 | 84 | 25 |
| Example 15 | 15 | 98 | 100 | 98 | 96 | 97 | 95 | 89 | 53 |
| Example 18 | 18 | 99 | 99 | 96 | 96 | 94 | 88 | 88 | 31 |
| Example 20 | 20 | 99 | 98 | 97 | 95 | 95 | 90 | 80 | 26 |
| Example 22 | 22 | 97 | 98 | 97 | 96 | 93 | 91 | 86 | 25 |
| Example 23 | 23 | 99 | 96 | 95 | 95 | 95 | 90 | 90 | 28 |
| Example 24 | 24 | 97 | 95 | 94 | 94 | 91 | 88 | 88 | 27 |
| Example 27 | 27 | 100 | 98 | 93 | 90 | 90 | 45 | 40 | 7 |

TABLE 6

Urease: 25° C.

| | Compound | Biocatalyst solvent $R_4-{}^+N(R_1)(R_3)-R_2$ $X^-$ | Aqueous solution concentration | Enzyme concentration (mg/mL) |
|---|---|---|---|---|
| Comparative Example 1 | 28 | Bu$_4$N$^+$ CH$_3$CH(OH)COO$^-$ | — | 1 |
| Comparative Example 2 | 29 | BMI-BF$_4$ | — | 1 |
| Comparative Example 6 | 33 | HOPMI-PF$_6$ | — | 15 |
| Comparative Example 7 | 34 | DHOPMI-PF$_6$ | — | 15 |
| Comparative Example 8 | 35 | Glycerin | 100% | 30 |
| Comparative Example 9 | 36 | Buffer | 10 mM | 30 |
| Comparative Example 10 | 37 | Aqueous solution of glycerin | 10 mg/mL | 30 |
| Comparative Example 11 | 38 | Aqueous solution of glucose | 10 mg/mL | 30 |
| Comparative Example 12 | 39 | Aqueous solution of bovine serum albumin | 10 mg/mL | 30 |
| Comparative Example 13 | 40 | Aqueous solution of lysine | 10 mg/mL | 30 |
| Comparative Example 14 | 41 | Aqueous solution of lysine and bovine serum albumin | 10 mg/mL | 30 |
| Comparative Example 15 | 42 | Aqueous solution of arginine | 10 mg/mL | 30 |

TABLE 6-continued

| | | Enzyme activity retention ratio (%) Storage period | | | | | | | |
|---|---|---|---|---|---|---|---|---|---|
| | Compound | After 1 day | After 7 days | After 14 days | After 21 days | After 30 days | After 60 days | After 90 days | After 180 days |
| Comparative Example 1 | 28 | — | — | 11 | 2 | 0 | 0 | 0 | 0 |
| Comparative Example 2 | 29 | — | — | 12 | 5 | 0 | 0 | 0 | 0 |
| Comparative Example 6 | 33 | 80 | 72 | 60 | 8 | 0 | 0 | 0 | 0 |
| Comparative Example 7 | 34 | 85 | 78 | 60 | 22 | 0 | 0 | 0 | 0 |
| Comparative Example 8 | 35 | 100 | 88 | 80 | 19 | 18 | 0 | 0 | 0 |
| Comparative Example 9 | 36 | 100 | 96 | 93 | 91 | 88 | 0 | 0 | 0 |
| Comparative Example 10 | 37 | 100 | 97 | 90 | 87 | 79 | 0 | 0 | 0 |
| Comparative Example 11 | 38 | 100 | 95 | 90 | 86 | 75 | 0 | 0 | 0 |
| Comparative Example 12 | 39 | 100 | 99 | 93 | 89 | 81 | 0 | 0 | 0 |
| Comparative Example 13 | 40 | 100 | 87 | 90 | 60 | 10 | 0 | 0 | 0 |
| Comparative Example 14 | 41 | 100 | 85 | 93 | 89 | 60 | 0 | 0 | 0 |
| Comparative Example 15 | 42 | 99 | 97 | 94 | 85 | 65 | 0 | 0 | 0 |

TABLE 7

Urease: 40° C.

| | | Biocatalyst solvent $R_4 \text{---} {}^+N(R_1)(R_2)(R_3) \; X^-$ | | | | | Aqueous solution concentration | Enzyme concentration (mg/mL) |
|---|---|---|---|---|---|---|---|---|
| | Compound | $R_1$ | $R_2$ | $R_3$ | $R_4$ | $X^-$ | | |
| Example 1 | 1 | $(CH_2)_2OH$ | H | H | H | $CH_3CH(OH)COO^-$ | — | 47.5 |
| Example 2 | 2 | $(CH_2)_2OH$ | $(CH_2)_2OH$ | H | H | $CH_3CH(OH)COO^-$ | — | 47.5 |
| Example 3 | 3 | $(CH_2)_2OH$ | $(CH_2)_2OH$ | $(CH_2)_2OH$ | H | $CH_3COO^-$ | — | 45 |
| Example 4 | 4 | | | | | $CH_3CH(OH)COO^-$ | — | 50 |
| Example 5 | 5 | | | | | $HOOC(CH_2)_2COO^-$ | — | 50 |
| Example 6 | 6 | | | | | Citric acid | — | 50 |
| Example 8 | 8 | 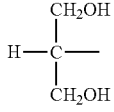 | H | H | H | $CH_3CH(OH)COO^-$ | — | 47.5 |
| Example 9 | 9 | 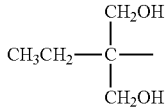 | H | H | H | $CH_3CH(OH)COO^-$ | — | 47.5 |

| | | Enzyme activity retention ratio (%) Storage period | | | | | | |
|---|---|---|---|---|---|---|---|---|
| | Compound | After 1 day | After 7 days | After 14 days | After 21 days | After 30 days | After 60 days | After 90 days |
| Example 1 | 1 | 95 | 92 | 84 | 72 | 67 | 61 | 20 |
| Example 2 | 2 | 92 | 90 | 82 | 73 | 68 | 61 | 16 |
| Example 3 | 3 | 97 | 91 | 81 | 75 | 72 | 65 | 18 |
| Example 4 | 4 | 93 | 91 | 80 | 76 | 75 | 65 | 24 |
| Example 5 | 5 | 97 | 92 | 81 | 75 | 70 | 61 | 20 |
| Example 6 | 6 | 94 | 90 | 78 | 73 | 71 | 61 | 18 |
| Example 8 | 8 | 94 | 93 | 82 | 74 | 71 | 63 | 14 |
| Example 9 | 9 | 96 | 93 | 80 | 76 | 72 | 60 | 17 |

TABLE 8

Urease: 40° C.

| | Compound | Biocatalyst solvent $R_4-^+N(R_1)(R_2)(R_3)$ X$^-$ | | | | | Aqueous solution concentration | Enzyme concentration (mg/mL) |
|---|---|---|---|---|---|---|---|---|
| | | $R_1$ | $R_2$ | $R_3$ | $R_4$ | $X^-$ | | |
| Example 10 | 10 | CH$_2$OH | H | H | H | CH$_3$CH(OH)COO$^-$ | — | 50 |
| Example 11 | 11 | HOCH$_2$—C(CH$_2$OH)— | | | | Citric acid | — | 50 |
| Example 13 | 13 | (same) | | | | CH$_3$SO$_3^-$ | — | 50 |
| Example 15 | 15 | HOCH$_2$CH(OH)CH(OH)CH(OH)CH$_2$— | H | H | H | CH$_3$CH(OH)COO$^-$ | — | 50 |
| Example 18 | 18 | (same) | | | | CH$_3$—O—CH$_2$COO$^-$ | — | 47.5 |
| Example 20 | 20 | CH$_3$ | CH$_3$ | CH$_3$ | (CH$_2$)$_2$OH | CH$_3$CH(OH)COO$^-$ | — | 45 |
| Example 22 | 22 | | | | | H$_2$PO$_4^-$ | — | 30 |
| Example 23 | 23 | CH$_3$ | CH$_3$ | CH$_3$CH$_2$ | (CH$_2$)$_2$OH | CH$_3$COO$^-$ | — | 30 |
| Example 24 | 24 | | | | | CH$_3$CH(OH)COO$^-$ | — | 42.5 |
| Example 27 | 27 | CH$_3$ | CH$_3$ | CH$_3$CH$_2$ | (CH$_2$)$_2$COOH | CH$_3$SO$_3^-$ | — | 30 |

| | Compound | Enzyme activity retention ratio (%) Storage period | | | | | | |
|---|---|---|---|---|---|---|---|---|
| | | After 1 day | After 7 days | After 14 days | After 21 days | After 30 days | After 60 days | After 90 days |
| Example 10 | 10 | 96 | 84 | 80 | 76 | 75 | 68 | 20 |
| Example 11 | 11 | 93 | 91 | 86 | 75 | 68 | 65 | 20 |
| Example 13 | 13 | 93 | 91 | 81 | 76 | 71 | 65 | 16 |
| Example 15 | 15 | 94 | 91 | 79 | 77 | 75 | 68 | 22 |
| Example 18 | 18 | 97 | 91 | 83 | 74 | 71 | 66 | 19 |
| Example 20 | 20 | 95 | 91 | 82 | 75 | 75 | 68 | 22 |
| Example 22 | 22 | 95 | 90 | 74 | 68 | 64 | 62 | 19 |
| Example 23 | 23 | 94 | 90 | 81 | 76 | 70 | 64 | 14 |
| Example 24 | 24 | 93 | 92 | 78 | 70 | 65 | 61 | 13 |
| Example 27 | 27 | 95 | 89 | 77 | 65 | 64 | 40 | 15 |

TABLE 9

Urease: 40° C.

| | Compound | Biocatalyst solvent $R_4-^+N(R_1)(R_2)(R_3)$ X$^-$ | | | | | Aqueous solution concentration | Enzyme concentration (mg/mL) |
|---|---|---|---|---|---|---|---|---|
| | | $R_1$ | $R_2$ | $R_3$ | $R_4$ | $X^-$ | | |
| Comparative Example 1 | 28 | Bu$_4$N$^+$ CH$_3$CH(OH)COO$^-$ | | | | | — | 1 |
| Comparative Example 2 | 29 | BMI-BF$_4$ | | | | | — | 1 |
| Comparative Example 6 | 33 | HOPMI-PF$_6$ | | | | | — | 15 |
| Comparative Example 7 | 34 | DHOPMI-PF$_6$ | | | | | — | 15 |
| Comparative Example 8 | 35 | Glycerin | | | | | 100% | 30 |
| Comparative Example 9 | 36 | Buffer | | | | | 10 mM | 30 |
| Comparative Example 10 | 37 | Aqueous solution of glycerin | | | | | 10 mg/mL | 30 |
| Comparative Example 11 | 38 | Aqueous solution of glucose | | | | | 10 mg/mL | 30 |
| Comparative Example 12 | 39 | Aqueous solution of bovine serum albumin | | | | | 10 mg/mL | 30 |
| Comparative Example 13 | 40 | Aqueous solution of lysine | | | | | 10 mg/mL | 30 |
| Comparative Example 14 | 41 | Aqueous solution of lysine and bovine serum albumin | | | | | 10 mg/mL | 30 |
| Comparative Example 15 | 42 | Aqueous solution of arginine | | | | | 10 mg/mL | 30 |

TABLE 9-continued

| | Compound | Enzyme activity retention ratio (%) Storage period | | | | | | |
|---|---|---|---|---|---|---|---|---|
| | | After 1 day | After 7 days | After 14 days | After 21 days | After 30 days | After 60 days | After 90 days |
| Comparative Example 1 | 28 | — | — | 11 | 0 | 0 | 0 | 0 |
| Comparative Example 2 | 29 | — | — | 12 | 0 | 0 | 0 | 0 |
| Comparative Example 6 | 33 | 55 | 30 | 18 | 5 | 0 | 0 | 0 |
| Comparative Example 7 | 34 | 58 | 31 | 22 | 6 | 0 | 0 | 0 |
| Comparative Example 8 | 35 | 90 | 80 | 16 | 10 | 5 | 0 | 0 |
| Comparative Example 9 | 36 | 90 | 74 | 20 | 0 | 0 | 0 | 0 |
| Comparative Example 10 | 37 | 91 | 87 | 68 | 40 | 0 | 0 | 0 |
| Comparative Example 11 | 38 | 94 | 90 | 68 | 40 | 0 | 0 | 0 |
| Comparative Example 12 | 39 | 90 | 87 | 67 | 50 | 30 | 0 | 0 |
| Comparative Example 13 | 40 | 92 | 92 | 15 | 0 | 0 | 0 | 0 |
| Comparative Example 14 | 41 | 90 | 87 | 40 | 0 | 0 | 0 | 0 |
| Comparative Example 15 | 42 | 96 | 92 | 28 | 19 | 0 | — | — |

According to the results obtained under the conditions of 40° C. (Tables 7 to 9), in the imidazolium-based ionic liquids, tetraalkylammonium-based ionic liquids, and aqueous solutions of general additives (compounds 28, 29, and 33 to 42), despite that the enzyme concentration was low (1 to 30 mg/mL), the activity retention ratio decreased to 0% to 30% after 30 days, and to 0% after 90 days. In contrast, the compounds of the present invention 1 to 6, 8 to 11, 13, 15, 18, 20, 22 to 24, and 27 (Examples 1 to 6, 8 to 11, 13, 15, 18, 20, 22 to 24, and 27) exhibited activity retention ratios of 64% or higher after 30 days, and 13% or higher after 90 days, under high concentration conditions (30 to 50 mg/mL). Furthermore, under the conditions of 25° C. (Tables 4 to 6), the activity retention ratios of compounds 28, 29, and 33 to 42 of Comparative Examples 1, 2, and 6 to 15 under low concentration conditions (1 to 30 mg/mL) after 30 days became 0% to 88%, and 0% after 90 days. In contrast, the compounds of the present invention exhibited activity retention ratios of 90% or higher after 30 days, 40% or higher after 90 days, and 7% or higher after 180 days, under high concentration conditions (30 to 50 mg/mL). That is, it was suggested that under the conditions of high concentration, high temperature and a long time period, the biocatalyst solvents of the present invention retain the activity of enzymes, and have high retainability for enzyme conformations.

Furthermore, the ionic liquids of the present invention retained an activity of 90% or higher at 25° C. and an activity of 64% or higher at 40° C., after 30 days from the initiation of storage, while in the imidazolium-based ionic liquids having hydroxyl groups (compounds 33 and 34), the activity retention ratio after 30 days decreased to 0% at both 25° C. and 40° C. That is, it was suggested that in a case in which the cation is an imidazolium-based cation, even if the ionic liquid has hydroxyl groups, since the molecular structure of the cation is a cyclic structure and is rigid, retainability of the conformation of amino acid residues inside an enzyme is low. In contrast, it was suggested that since the biocatalyst solvents of the present invention are quaternary ammonium-based compounds have cations with a small molecule size and have flexible structures, protection reaches even to the amino acid residues in the interior of an enzyme, and the biocatalyst solvents have high retainability for enzyme conformations.

<Activity Analysis for Oxidoreductase: Catalase: Tables 10 to 15>

Catalase is an enzyme that decomposes hydrogen peroxide into oxygen and hydrogen. Its activity was measured by quantitatively determining the amount of hydrogen peroxide, which is a reaction substrate of catalase.

First, 100 mL of a 16 mM substrate solution (prepared by dissolving hydrogen peroxide that served as a substrate in a 10 mM phosphate buffer solution at pH 7.0) was collected in a conical flask, and the substrate solution was preliminarily warmed to 25° C. for about 30 minutes.

Next, samples (compounds 1 to 6, 8 to 11, 13, 15, 18, 20, 22 to 24, 27, and 33 to 41) that had been left to stand at the set concentrations and temperatures described in Tables 10 to 15 for a predetermined time period were each added to the above-mentioned substrate solution such that the amount of enzyme would be 0.5 mg, and the mixtures were allowed to react for 30 minutes at 25° C.

After the reaction, 2.5 mL of a titanium solution (prepared by dissolving 1 g of titanium oxide and 10 g of potassium sulfate in 150 mL of concentrated sulfuric acid, heating the solution to 180° C. to 220° C. for 2 to 3 hours, and then diluting the solution in a measuring cylinder to 1.5 L using ion-exchanged water) was added to the reaction solution to terminate the reaction. The absorbance at 410 nm of this solution after stopping the reaction was measured, the amount of hydrogen peroxide was quantitatively determined, and the catalase activity was calculated. The amount of hydrogen peroxide was calculated using a calibration curve produced using hydrogen peroxide solutions in the concentration range of 1 to 16 mM (prepared by dissolving hydrogen peroxide in a 10 mM phosphate buffer solution at pH 7.0, and diluting the solution to a predetermined concentration).

Meanwhile, the value of the enzyme activity that served as a reference for the enzyme activity retention ratio was calculated as follows. A catalase powder that had been stored at an appropriate temperature was dissolved in a buffer (10 mM phosphate buffer solution at pH 7.0), and thus an enzyme solution having an enzyme concentration of 50 mg/mL was prepared. After the preparation, the solution was immediately added to the substrate solution as described above, such that the amount of enzyme would be 0.5 mg, and an enzymatic reaction was induced thereby. Subsequently, the enzyme activity retention ratio was calculated based on the amount of hydrogen peroxide that had been calculated by a method similar to that described above, as a reference.

The results are presented in Tables 10 to 15.

TABLE 10

Catalase: 25° C.

Biocatalyst solvent $$R_4 - \overset{R_1}{\underset{R_3}{\overset{|}{N^+}}} - R_2 \quad X^-$$

| | Compound | R₁ | R₂ | R₃ | R₄ | X⁻ | Aqueous solution concentration |
|---|---|---|---|---|---|---|---|
| Example 1 | 1 | (CH₂)₂OH | H | H | H | CH₃CH(OH)COO⁻ | — |
| Example 2 | 2 | (CH₂)₂OH | (CH₂)₂OH | H | H | CH₃CH(OH)COO⁻ | — |
| Example 3 | 3 | (CH₂)₂OH | (CH₂)₂OH | (CH₂)₂OH | H | CH₃COO⁻ | — |
| Example 4 | 4 | | | | | CH₃CH(OH)COO⁻ | — |
| Example 5 | 5 | | | | | HOOC(CH₂)₂COO⁻ | — |
| Example 6 | 6 | | | | | Citric acid | — |
| Example 8 | 8 | $H-\overset{CH_2OH}{\underset{CH_2OH}{\overset{|}{C}}}-$ | H | H | H | CH₃CH(OH)COO⁻ | — |
| Example 9 | 9 | $CH_3CH_2-\overset{CH_2OH}{\underset{CH_2OH}{\overset{|}{C}}}-$ | H | H | H | CH₃CH(OH)COO⁻ | — |

| | Enzyme concentration (mg/mL) | Enzyme activity retention ratio (%) Storage period | | | | | | |
|---|---|---|---|---|---|---|---|---|
| | | After 1 day | After 7 days | After 14 days | After 21 days | After 30 days | After 60 days | After 90 days |
| Example 1 | 45 | 100 | 100 | 100 | 100 | 98 | 98 | 89 |
| Example 2 | 45 | 100 | 100 | 100 | 100 | 98 | 92 | 85 |
| Example 3 | 40 | 100 | 100 | 100 | 100 | 98 | 98 | 94 |
| Example 4 | 50 | 100 | 100 | 100 | 100 | 100 | 92 | 85 |
| Example 5 | 50 | 100 | 100 | 100 | 100 | 91 | 90 | 80 |
| Example 6 | 45 | 100 | 100 | 100 | 100 | 91 | 99 | 90 |
| Example 8 | 45 | 100 | 100 | 100 | 100 | 97 | 99 | 90 |
| Example 9 | 45 | 100 | 100 | 100 | 100 | 99 | 98 | 85 |

TABLE 11

Catalase: 25° C.

Biocatalyst solvent $$R_4 - \overset{R_1}{\underset{R_3}{\overset{|}{N^+}}} - R_2 \quad X^-$$

| | Compound | R₁ | R₂ | R₃ | R₄ | X⁻ | Aqueous solution concentration |
|---|---|---|---|---|---|---|---|
| Example 10 | 10 | $HOCH_2-\overset{CH_2OH}{\underset{CH_2OH}{\overset{|}{C}}}-$ | H | H | H | CH₃CH(OH)COO⁻ | — |
| Example 11 | 11 | | | | | Citric acid | — |
| Example 13 | 13 | | | | | CH₃SO₃⁻ | — |
| Example 15 | 15 | $HOCH_2CH\overset{OH}{\underset{|}{\phantom{C}}}CHCH\overset{OH}{\underset{|}{\phantom{C}}}CHCH_2-$ | H | H | H | CH₃CH(OH)COO⁻ | — |
| Example 18 | 18 | | | | | CH₃—O—CH₂COO⁻ | — |
| Example 20 | 20 | CH₃ | CH₃ | CH₃ | (CH₂)₂OH | CH₃CH(OH)COO⁻ | — |
| Example 22 | 22 | | | | | H₂PO₄⁻ | — |
| Example 23 | 23 | CH₃ | CH₃ | CH₃CH₂ | (CH₂)₂OH | CH₃COO⁻ | — |

TABLE 11-continued

| | | | | | | Catalase: 25° C. | | | |
|---|---|---|---|---|---|---|---|---|---|
| Example 24 | 24 | | | | | | CH$_3$CH(OH)COO$^-$ | | — |
| Example 27 | 27 | | CH$_3$ | | CH$_3$ | CH$_3$CH$_2$ | (CH$_2$)$_2$COOH | CH$_3$SO$_3$- | — |

| | Enzyme concentration | Enzyme activity retention ratio (%) Storage period | | | | | | |
|---|---|---|---|---|---|---|---|---|
| | (mg/mL) | After 1 day | After 7 days | After 14 days | After 21 days | After 30 days | After 60 days | After 90 days |
| Example 10 | 50 | 100 | 100 | 100 | 100 | 100 | 97 | 90 |
| Example 11 | 45 | 100 | 100 | 100 | 100 | 94 | 94 | 80 |
| Example 13 | 40 | 100 | 100 | 100 | 100 | 98 | 93 | 75 |
| Example 15 | 50 | 100 | 100 | 100 | 100 | 100 | 95 | 88 |
| Example 18 | 42.5 | 100 | 100 | 100 | 100 | 98 | 99 | 89 |
| Example 20 | 42.5 | 100 | 100 | 100 | 100 | 100 | 99 | 80 |
| Example 22 | 20 | 100 | 100 | 100 | 100 | 96 | 96 | 90 |
| Example 23 | 20 | 100 | 100 | 100 | 100 | 98 | 92 | 82 |
| Example 24 | 40 | 100 | 100 | 100 | 100 | 98 | 91 | 82 |
| Example 27 | 30 | 100 | 100 | 100 | 98 | 91 | 90 | 78 |

TABLE 12

Catalase: 25° C.

| | Biocatalyst solvent | | | | | | | Aqueous solution concentration | Enzyme concentration (mg/mL) |
|---|---|---|---|---|---|---|---|---|---|
| | Compound | R$_1$ | R$_2$ | R$_3$ | R$_4$ | X$^-$ | | | |
| Comparative Example 6 | 33 | | | HOPMI-PF$_6$ | | | | — | 10 |
| Comparative Example 7 | 34 | | | DHOPMI-PF$_6$ | | | | — | 10 |
| Comparative Example 8 | 35 | | | Glycerin | | | | 100% | 20 |
| Comparative Example 9 | 36 | | | Buffer | | | | 10 mM | 20 |
| Comparative Example 10 | 37 | | | Aqueous solution of glycerin | | | | 10 mg/mL | 20 |
| Comparative Example 11 | 38 | | | Aqueous solution of glucose | | | | 10 mg/mL | 20 |
| Comparative Example 12 | 39 | | | Aqueous solution of bovine serum albumin | | | | 10 mg/mL | 20 |
| Comparative Example 13 | 40 | | | Aqueous solution of lysine | | | | 10 mg/mL | 20 |
| Comparative Example 14 | 41 | | | Aqueous solution of lysine and bovine serum albumin | | | | 10 mg/mL | 20 |

| | Enzyme activity retention ratio (%) Storage period | | | | | | |
|---|---|---|---|---|---|---|---|
| | After 1 day | After 7 days | After 14 days | After 21 days | After 30 days | After 60 days | After 90 days |
| Comparative Example 6 | 100 | 100 | 93 | 92 | 88 | 78 | 66 |
| Comparative Example 7 | 100 | 100 | 95 | 95 | 88 | 79 | 67 |
| Comparative Example 8 | 89 | 71 | 5 | 0 | 0 | 0 | 0 |
| Comparative Example 9 | 100 | 94 | 94 | 94 | 87 | 90 | 0 |
| Comparative Example 10 | 100 | 100 | 95 | 95 | 79 | 79 | 0 |
| Comparative Example 11 | 100 | 100 | 94 | 92 | 88 | 90 | 0 |
| Comparative Example 12 | 100 | 100 | 97 | 95 | 89 | 88 | 0 |
| Comparative Example 13 | 100 | 100 | 97 | 90 | 87 | 87 | 0 |
| Comparative Example 14 | 100 | 100 | 95 | 90 | 87 | 89 | 0 |

TABLE 13

Catalase: 40° C.

Biocatalyst solvent $$R_4 - \overset{R_1}{\underset{R_3}{\overset{|}{N^+}}} - R_2 \quad X^-$$

| | Compound | $R_1$ | $R_2$ | $R_3$ | $R_4$ | $X^-$ | Aqueous solution concentration |
|---|---|---|---|---|---|---|---|
| Example 1 | 1 | $(CH_2)_2OH$ | H | H | H | $CH_3CH(OH)COO^-$ | — |
| Example 2 | 2 | $(CH_2)_2OH$ | $(CH_2)_2OH$ | H | H | $CH_3CH(OH)COO^-$ | — |
| Example 3 | 3 | $(CH_2)_2OH$ | $(CH_2)_2OH$ | $(CH_2)_2OH$ | H | $CH_3COO^-$ | — |
| Example 4 | 4 | | | | | $CH_3CH(OH)COO^-$ | — |
| Example 5 | 5 | | | | | $HOOC(CH_2)_2COO^-$ | — |
| Example 6 | 6 | | | | | Citric acid | — |
| Example 8 | 8 | $H-\overset{CH_2OH}{\underset{CH_2OH}{\overset{|}{C}}}-$ | H | H | H | $CH_3CH(OH)COO^-$ | — |
| Example 9 | 9 | $CH_3CH_2-\overset{CH_2OH}{\underset{CH_2OH}{\overset{|}{C}}}-$ | H | H | H | $CH_3CH(OH)COO^-$ | — |

| | Enzyme concentration (mg/mL) | Enzyme activity retention ratio (%) Storage period | | | | | | |
|---|---|---|---|---|---|---|---|---|
| | | After 1 day | After 7 days | After 14 days | After 21 days | After 30 days | After 60 days | After 90 days |
| Example 1 | 45 | 100 | 100 | 95 | 95 | 95 | 93 | 50 |
| Example 2 | 45 | 100 | 100 | 99 | 96 | 96 | 96 | 57 |
| Example 3 | 40 | 100 | 100 | 97 | 97 | 97 | 90 | 38 |
| Example 4 | 50 | 100 | 100 | 100 | 95 | 93 | 88 | 40 |
| Example 5 | 50 | 100 | 100 | 97 | 95 | 90 | 80 | 59 |
| Example 6 | 45 | 100 | 100 | 99 | 96 | 96 | 94 | 55 |
| Example 8 | 45 | 100 | 100 | 99 | 96 | 95 | 85 | 52 |
| Example 9 | 45 | 100 | 100 | 99 | 96 | 95 | 90 | 55 |

TABLE 14

Catalase: 40° C.

Biocatalyst solvent $$R_4 - \overset{R_1}{\underset{R_3}{\overset{|}{N^+}}} - R_2 \quad X^-$$

| | Compound | $R_1$ | $R_2$ | $R_3$ | $R_4$ | $X^-$ | Aqueous solution concentration |
|---|---|---|---|---|---|---|---|
| Example 10 | 10 | $HOCH_2-\overset{CH_2OH}{\underset{CH_2OH}{\overset{|}{C}}}-$ | H | H | H | $CH_3CH(OH)COO^-$ | — |
| Example 11 | 11 | | | | | Citric acid | — |
| Example 13 | 13 | | | | | $CH_3SO_3^-$ | — |
| Example 15 | 15 | $HOCH_2\overset{OH}{\underset{}{\overset{|}{C}H}}\overset{}{CH}\overset{OH}{\underset{}{\overset{|}{C}H}}\overset{}{CH}CH_2-$ | H | H | H | $CH_3CH(OH)COO^-$ | — |
| Example 18 | 18 | | | | | $CH_3-O-CH_2COO^-$ | — |
| Example 20 | 20 | $CH_3$ | $CH_3$ | $CH_3$ | $(CH_2)_2OH$ | $CH_3CH(OH)COO^-$ | — |
| Example 22 | 22 | | | | | $H_2PO_4^-$ | — |

TABLE 14-continued

Catalase: 40° C.

| | | R₁ | R₂ | R₃ | R₄ | X⁻ | |
|---|---|---|---|---|---|---|---|
| Example 23 | 23 | CH₃ | CH₃ | CH₃CH₂ | (CH₂)₂OH | CH₃COO⁻ | — |
| Example 24 | 24 | | | | | CH₃CH(OH)COO⁻ | |
| Example 27 | 27 | CH₃ | CH₃ | CH₃CH₂ | (CH₂)₂COOH | CH₃SO₃- | — |

| | Enzyme concentration | Enzyme activity retention ratio (%) Storage period | | | | | | |
|---|---|---|---|---|---|---|---|---|
| | (mg/mL) | After 1 day | After 7 days | After 14 days | After 21 days | After 30 days | After 60 days | After 90 days |
| Example 10 | 50 | 100 | 100 | 100 | 96 | 95 | 95 | 48 |
| Example 11 | 45 | 100 | 100 | 99 | 95 | 94 | 90 | 34 |
| Example 13 | 40 | 100 | 100 | 99 | 96 | 96 | 91 | 40 |
| Example 15 | 50 | 100 | 100 | 100 | 97 | 96 | 96 | 48 |
| Example 18 | 42.5 | 100 | 100 | 99 | 99 | 99 | 98 | 49 |
| Example 20 | 42.5 | 100 | 100 | 100 | 98 | 96 | 86 | 40 |
| Example 22 | 20 | 100 | 100 | 96 | 96 | 93 | 88 | 30 |
| Example 23 | 20 | 100 | 100 | 95 | 95 | 94 | 90 | 35 |
| Example 24 | 40 | 100 | 100 | 99 | 98 | 95 | 90 | 40 |
| Example 27 | 30 | 100 | 100 | 99 | 95 | 90 | 80 | 30 |

TABLE 15

Catalase: 40° C.

Biocatalyst solvent $$R_4 - \overset{R_1}{\underset{R_3}{\overset{|}{N^+}}} - R_2 \quad X^-$$

| | Compound | R₁ | R₂ | R₃ | R₄ | X⁻ | Aqueous solution concentration |
|---|---|---|---|---|---|---|---|
| Comparative Example 6 | 33 | HOPMI-PF₆ | | | | | — |
| Comparative Example 7 | 34 | DHOPMI-PF₆ | | | | | — |
| Comparative Example 8 | 35 | Glycerin | | | | | 100% |
| Comparative Example 9 | 36 | Buffer | | | | | 10 mM |
| Comparative Example 10 | 37 | Aqueous solution of glycerin | | | | | 10 mg/mL |
| Comparative Example 11 | 38 | Aqueous solution of glucose | | | | | 10 mg/mL |
| Comparative Example 12 | 39 | Aqueous solution of bovine serum albumin | | | | | 10 mg/mL |
| Comparative Example 13 | 40 | Aqueous solution of lysine | | | | | 10 mg/mL |
| Comparative Example 14 | 41 | Aqueous solution of lysine and bovine serum albumin | | | | | 10 mg/mL |

| | Enzyme concentration | Enzyme activity retention ratio (%) Storage period | | | | | | |
|---|---|---|---|---|---|---|---|---|
| | (mg/mL) | After 1 day | After 7 days | After 14 days | After 21 days | After 30 days | After 60 days | After 90 days |
| Comparative Example 6 | 10 | 100 | 100 | 92 | 90 | 80 | 60 | 24 |
| Comparative Example 7 | 10 | 100 | 100 | 92 | 90 | 81 | 69 | 28 |
| Comparative Example 8 | 20 | 74 | 60 | 8 | 0 | 0 | 0 | 0 |
| Comparative Example 9 | 20 | 100 | 94 | 92 | 92 | 88 | 90 | 0 |
| Comparative Example 10 | 20 | 100 | 100 | 95 | 94 | 53 | 0 | 0 |
| Comparative Example 11 | 20 | 100 | 100 | 95 | 10 | 0 | 0 | 0 |
| Comparative Example 12 | 20 | 100 | 100 | 94 | 93 | 87 | 84 | 0 |
| Comparative Example 13 | 20 | 100 | 60 | 6 | 6 | 5 | 0 | 0 |
| Comparative Example 14 | 20 | 100 | 93 | 24 | 9 | 3 | 0 | 0 |

After 30 days, the ionic liquids of the present invention (compounds 1 to 6, 8 to 11, 13, 15, 18, 20, 22 to 24, and 27) retained a catalytic activity of 91% or higher under the conditions of 25° C. (Tables 10 to 12) and a catalytic activity of 90% or higher under the conditions of 40° C. (Tables 13 to 15). In contrast, in Comparative Examples 6 to 14 (compounds 33 to 41), the catalytic activity became 0% to 89% at 25° C. and 0% to 88% under the conditions of 40° C. Furthermore, after 90 days, the ionic liquids of the present invention retained a catalytic activity of 75% or higher under the conditions of 25° C., and a catalytic activity of 30% or higher under the conditions of 40° C., while in Comparative Examples, the catalytic activity became 0% to 67% at 25° C., and 0% to 28% under the conditions of 40° C. Therefore, the ionic liquids of the present invention showed superiority.

In regard to urease (Tables 4 to 9) and catalase (Tables 10 to 15), for example, compared to the ionic liquids of the present invention having two hydroxyl groups in the molecule (compounds 20 and 24), the sample of 100% glycerin having three hydroxyl groups in the molecule (compound 35) tended to show a low enzyme activity retention ratio. That is, it was suggested that in order to retain the enzyme conformation and to maintain the activity, hydroxyl groups as well as a salt structure composed of a cation and an anion contribute to the retention.

<Activity Analysis for Hydrolase: Amylase: Tables 16 and 17>

Amylase is an enzyme that converts amylose or amylopectin in starch to glucose, which is a monosaccharide; maltose, which is a disaccharide; and oligosaccharides. Its activity was measured by quantitatively determining the amount of starch, which is a reaction substrate of amylase.

First, a substrate solution was prepared by introducing 25 mL of a 0.3% starch solution, 10 mL of a 0.5 M sodium acetate buffer solution, and 12.5 mL of ion-exchanged water into a conical flask. This substrate solution was preliminarily warmed to 37° C. for about 30 minutes.

Next, samples (compounds 3 to 6, 10, 11, 13, 18, 22, 23 and 27) that had been left to stand at the set concentrations and temperatures described in Tables 16 and 17 for a predetermined time period, were each added to the above-mentioned substrate solution such that the amount of enzyme would be 0.5 mg, and the mixtures were allowed to react for 30 minutes at 37° C.

After the reaction, 6 mL of 1 N hydrochloric acid was added to the flask to terminate the reaction. 0.5 mL of an iodine solution (prepared by dissolving 120 mg of potassium iodide and 12 mg of iodine in 10 mL of ion-exchanged water), the absorbance at 700 nm of this solution was measured, and the amount of starch was quantitatively determined. Thus, the amylase activity was calculated. The amount of starch was calculated using a calibration curve produced from starch solutions in the concentration range of 0.1% to 0.3%.

Meanwhile, the value of the enzyme activity that served as a reference for the enzyme activity retention ratio was calculated as follows. An amylase powder that had been stored at an appropriate temperature was dissolved in a buffer (10 mM phosphate buffer solution at pH 6.5), and thus an enzyme solution having an enzyme concentration of 0.5 mg/mL was prepared. After the preparation, the solution was immediately added to the substrate solution as described above such that the amount of enzyme would be 0.5 mg, and an enzymatic reaction was induced thereby. Subsequently, the enzyme activity retention ratio was calculated based on the amount of starch calculated by a method similar to that described above, as a reference.

The results are presented in Tables 16 and 17.

TABLE 16

Amylase: 25° C.

Biocatalyst solvent $$R_4 - {}^+N(R_1)(R_3) - R_2 \quad X^-$$

| | Compound | $R_1$ | $R_2$ | $R_3$ | $R_4$ | $X^-$ | Aqueous solution concentration |
|---|---|---|---|---|---|---|---|
| Example 3 | 3 | $(CH_2)_2OH$ | $(CH_2)_2OH$ | $(CH_2)_2OH$ | H | $CH_3COO^-$ | — |
| Example 4 | 4 | | | | | $CH_3CH(OH)COO^-$ | — |
| Example 5 | 5 | | | | | $HOOC(CH_2)_2COO^-$ | — |
| Example 6 | 6 | | | | | Citric acid | — |
| Example 10 | 10 | $HOCH_2-C(CH_2OH)(CH_2OH)-$ | H | H | H | $CH_3CH(OH)COO^-$ | — |
| Example 11 | 11 | | | | | Citric acid | — |
| Example 13 | 13 | | | | | $CH_3SO_3^-$ | — |
| Example 18 | 18 | $HOCH_2CH(OH)CH(OH)CH(OH)CH(OH)CH_2-$ | H | H | H | $CH_3-O-CH_2COO^-$ | — |
| Example 22 | 22 | $CH_3$ | $CH_3$ | $CH_3$ | $(CH_2)_2OH$ | $H_2PO_4^-$ | — |
| Example 23 | 23 | $CH_3$ | $CH_3$ | $CH_3CH_2$ | $(CH_2)_2OH$ | $CH_3COO^-$ | — |
| Example 27 | 27 | $CH_3$ | $CH_3$ | $CH_3CH_2$ | $(CH_2)_2COOH$ | $CH_3SO_3^-$ | — |

| | Enzyme concentration (mg/mL) | Enzyme activity retention ratio (%) Storage period | | | |
|---|---|---|---|---|---|
| | | After 1 day | After 7 days | After 14 days | After 21 days |
| Example 3 | 1.0 | 99 | 99 | 99 | 98 |
| Example 4 | 2.0 | 99 | 99 | 99 | 98 |
| Example 5 | 1.5 | 98 | 90 | 60 | 50 |
| Example 6 | 1.5 | 99 | 95 | 65 | 54 |
| Example 10 | 2.0 | 95 | 93 | 90 | 58 |
| Example 11 | 1.5 | 98 | 91 | 62 | 50 |
| Example 13 | 1.0 | 99 | 92 | 61 | 57 |
| Example 18 | 1.5 | 99 | 95 | 68 | 60 |
| Example 22 | 0.5 | 95 | 98 | 59 | 50 |
| Example 23 | 1.0 | 98 | 99 | 99 | 98 |
| Example 27 | 0.5 | 95 | 98 | 56 | 45 |

TABLE 17

Amylase: 40° C.

Biocatalyst solvent $$R_4-{}^+N(R_1)(R_2)(R_3)\ X^-$$

| Compound | | $R_1$ | $R_2$ | $R_3$ | $R_4$ | $X^-$ |
|---|---|---|---|---|---|---|
| Example 3 | 3 | $(CH_2)_2OH$ | $(CH_2)_2OH$ | $(CH_2)_2OH$ | H | $CH_3COO^-$ |
| Example 4 | 4 | | | | | $CH_3CH(OH)COO^-$ |
| Example 5 | 5 | | | | | $HOOC(CH_2)_2COO^-$ |
| Example 6 | 6 | | | | | Citric acid |
| Example 10 | 10 | $HOCH_2-C(CH_2OH)(CH_2OH)-$ | H | H | H | $CH_3CH(OH)COO^-$ |
| Example 11 | 11 | | | | | Citric acid |
| Example 13 | 13 | | | | | $CH_3SO_3^-$ |
| Example 18 | 18 | $HOCH_2CH(OH)CH(OH)CH(OH)CH_2-$ | H | H | H | $CH_3-O-CH_2COO^-$ |
| Example 22 | 22 | $CH_3$ | $CH_3$ | $CH_3$ | $(CH_2)_2OH$ | $H_2PO_4^-$ |
| Example 23 | 23 | $CH_3$ | $CH_3$ | $CH_3CH_2$ | $(CH_2)_2OH$ | $CH_3COO^-$ |
| Example 27 | 27 | $CH_3$ | $CH_3$ | $CH_3CH_2$ | $(CH_2)_2COOH$ | $CH_3SO_3^-$ |

| | Aqueous solution concentration | Enzyme concentration (mg/mL) | Enzyme activity retention ratio (%) Storage period | | | |
|---|---|---|---|---|---|---|
| | | | After 1 day | After 7 days | After 14 days | After 21 days |
| Example 3 | — | 1.0 | 98 | 95 | 69 | 41 |
| Example 4 | — | 2.0 | 99 | 97 | 69 | 35 |
| Example 5 | — | 1.5 | 98 | 90 | 40 | 21 |
| Example 6 | — | 1.5 | 98 | 91 | 47 | 18 |
| Example 10 | — | 2.0 | 95 | 96 | 70 | 38 |
| Example 11 | — | 1.5 | 97 | 89 | 42 | 16 |
| Example 13 | — | 1.0 | 97 | 90 | 41 | 18 |
| Example 18 | — | 1.5 | 98 | 92 | 48 | 21 |
| Example 22 | — | 0.5 | 95 | 90 | 35 | 15 |
| Example 23 | — | 1.0 | 96 | 95 | 65 | 33 |
| Example 27 | — | 0.5 | 96 | 95 | 49 | 18 |

After 21 days, the ionic liquids of the present invention (compounds 3 to 6, 10, 11, 13, 18, 22, 23, and 27) retained a catalytic activity of 45% or higher under the conditions of 25° C. (Table 16), and 15% or higher under the conditions of 40° C. (Table 17).

<Activity Analysis for Transferase: Citrate Synthase: Tables 18 and 19>

Citrate synthase is an enzyme that contributes to a reaction between oxaloacetic acid+acetyl-coenzyme A+H₂O→citric acid+coenzyme A+H⁺. The activity of the enzyme was measured by quantitatively determining the amount of a product obtainable by reacting coenzyme A produced by the reaction, with DTNB (5,5'-dithiobis-2-nitrobenzoic acid).

First, 50 µL of a 0.2 mM oxaloacetic acid solution (prepared by dissolving oxaloacetic acid in a 50 mM aqueous solution of trishydroxymethylaminomethane (Tris buffer solution) that had been adjusted to pH 8.0 with hydrochloric acid), 30 µL of a 0.2 mM acetyl-coenzyme A solution (prepared by dissolving acetyl-coenzyme A in ion-exchanged water), 100 µL of a 0.1 mM DTND solution (prepared by diluting DTND with a 1 M Tris buffer solution adjusted to pH 8.0, to a concentration of 0.1 mM), and 770 µL of ion-exchanged water were introduced into a 10-mL screw tube, and thereby a substrate solution was prepared. This substrate solution was preliminarily warmed to 25° C. for about 30 minutes.

Next, samples (compounds 3 to 6, 10, 11, 13, 18, 22, 23, and 27) that had been left to stand at the set concentrations and temperatures described in Tables 18 and 19 for a predetermined time period, were each added to the above-mentioned substrate solution such that the amount of enzyme would be 0.1 mg, and the mixtures were allowed to react for 3 minutes at 25° C.

After the reaction, the absorbances at 412 nm of the substrate solution as a blank and the reaction solution were measured, and thereby the product produced from coenzyme A and DTNB was quantitatively determined by the following expression.

Concentration (M)=(Absorbance of reaction solution−absorbance of blank)/13600×·X·Molar extinction coefficient 13600 L/(M·cm)

The value of the enzyme activity that served as a reference for the enzyme activity retention ratio was calculated as follows. Citrate synthase that had been stored at an appropriate temperature was dissolved in a buffer (1 M Tris buffer solution adjusted to pH 8.0), and thus an enzyme solution having an enzyme concentration of 0.1 mg/mL was prepared. After the preparation, the solution was immediately added to the substrate solution as described above, such that the amount of enzyme would be 0.1 mg, and an enzymatic reaction was induced thereby. Subsequently, the enzyme activity retention ratio was calculated based on the amount of the product calculated by a method similar to that described above, as a reference.

The results are presented in Tables 18 and 19.

TABLE 18

Citrate synthase: 25° C.

Biocatalyst solvent $$R_4 - \overset{R_1}{\underset{R_3}{\overset{|}{N^+}}} - R_2 \quad X^-$$

| | Compound | $R_1$ | $R_2$ | $R_3$ | $R_4$ | $X^-$ |
|---|---|---|---|---|---|---|
| Example 3 | 3 | $(CH_2)_2OH$ | $(CH_2)_2OH$ | $(CH_2)_2OH$ | H | $CH_3COO^-$ |
| Example 4 | 4 | | | | | $CH_3CH(OH)COO^-$ |
| Example 5 | 5 | | | | | $HOOC(CH_2)_2COO^-$ |
| Example 6 | 6 | | | | | Citric acid |
| Example 10 | 10 | $HOCH_2-\underset{\underset{CH_2OH}{\mid}}{\overset{\overset{CH_2OH}{\mid}}{C}}-$ | H | H | H | $CH_3CH(OH)COO^-$ |
| Example 11 | 11 | | | | | Citric acid |
| Example 13 | 13 | | | | | $CH_3SO_3^-$ |
| Example 18 | 18 | $HOCH_2\underset{\underset{OH}{\mid}}{CH}\underset{}{CH}\underset{\underset{OH}{\mid}}{CH}\underset{}{CH}CH_2-$ (with OH OH on other carbons) | H | H | H | $CH_3-O-CH_2COO^-$ |
| Example 22 | 22 | $CH_3$ | $CH_3$ | $CH_3$ | $(CH_2)_2OH$ | $H_2PO_4^-$ |
| Example 23 | 23 | $CH_3$ | $CH_3$ | $CH_3CH_2$ | $(CH_2)_2OH$ | $CH_3COO^-$ |
| Example 27 | 27 | $CH_3$ | $CH_3$ | $CH_3CH_2$ | $(CH_2)_2COOH$ | $CH_3SO_3^-$ |

| | Aqueous solution concentration | Enzyme concentration (mg/mL) | Enzyme activity retention ratio (%) Storage period | | | |
|---|---|---|---|---|---|---|
| | | | After 1 day | After 7 days | After 14 days | After 21 days |
| Example 3 | — | 6.0 | 95 | 90 | 35 | 13 |
| Example 4 | — | 10.0 | 96 | 90 | 42 | 15 |
| Example 5 | — | 10.0 | 94 | 88 | 30 | 12 |
| Example 6 | — | 10.0 | 96 | 85 | 41 | 13 |
| Example 10 | — | 10.0 | 95 | 88 | 38 | 12 |
| Example 11 | — | 10.0 | 95 | 85 | 32 | 13 |
| Example 13 | — | 5.0 | 96 | 85 | 38 | 14 |
| Example 18 | — | 10.0 | 95 | 86 | 40 | 15 |
| Example 22 | — | 5.0 | 94 | 84 | 35 | 11 |
| Example 23 | — | 5.0 | 96 | 89 | 40 | 16 |
| Example 27 | — | 5.0 | 93 | 80 | 30 | 18 |

TABLE 19

Citrate synthase: 40° C.

Biocatalyst solvent $$R_4 - \overset{R_1}{\underset{R_3}{\overset{|}{N^+}}} - R_2 \quad X^-$$

| | Compound | $R_1$ | $R_2$ | $R_3$ | $R_4$ | $X^-$ |
|---|---|---|---|---|---|---|
| Example 3 | 3 | $(CH_2)_2OH$ | $(CH_2)_2OH$ | $(CH_2)_2OH$ | H | $CH_3COO^-$ |
| Example 4 | 4 | | | | | $CH_3CH(OH)COO^-$ |
| Example 5 | 5 | | | | | $HOOC(CH_2)_2COO^-$ |
| Example 6 | 6 | | | | | Citric acid |

TABLE 19-continued

| | | Citrate synthase: 40° C. | | | | |
|---|---|---|---|---|---|---|
| Example 10 | 10 | CH₂OH<br>\|<br>HOCH₂—C—<br>\|<br>CH₂OH | H | H | H | $CH_3CH(OH)COO^-$ |
| Example 11 | 11 | | | | | Citric acid |
| Example 13 | 13 | | | | | $CH_3SO_3^-$ |
| Example 18 | 18 | OH  OH<br>\|   \|<br>HOCH₂CHCHCHCH₂—<br>\|   \|<br>OH  OH | H | H | H | $CH_3—O—CH_2COO^-$ |
| Example 22 | 22 | $CH_3$ | $CH_3$ | $CH_3$ | $(CH_2)_2OH$ | $H_2PO_4^-$ |
| Example 23 | 23 | $CH_3$ | $CH_3$ | $CH_3CH_2$ | $(CH_2)_2OH$ | $CH_3COO^-$ |
| Example 27 | 27 | $CH_3$ | $CH_3$ | $CH_3CH_2$ | $(CH_2)_2COOH$ | $CH_3SO_3^-$ |

| | Aqueous solution concentration | Enzyme concentration (mg/mL) | Enzyme activity retention ratio (%) Storage period | | |
|---|---|---|---|---|---|
| | | | After 1 day | After 7 days | After 14 days |
| Example 3 | — | 6.0 | 72 | 56 | 18 |
| Example 4 | — | 10.0 | 72 | 52 | 20 |
| Example 5 | — | 10.0 | 68 | 50 | 19 |
| Example 6 | — | 10.0 | 70 | 50 | 18 |
| Example 10 | — | 10.0 | 71 | 51 | 21 |
| Example 11 | — | 10.0 | 69 | 49 | 23 |
| Example 13 | — | 5.0 | 72 | 49 | 18 |
| Example 18 | — | 10.0 | 69 | 48 | 15 |
| Example 22 | — | 5.0 | 65 | 46 | 16 |
| Example 23 | — | 5.0 | 66 | 52 | 20 |
| Example 27 | — | 5.0 | 64 | 45 | 20 |

The ionic liquids of the present invention (compounds 3 to 6, 10, 11, 13, 18, 22, 23, and 27) retained, under the conditions of 25° C. (Table 18), a catalytic activity of 11% or higher after 21 days, and under the conditions of 40° C. (Table 19), a catalytic activity of 15% or higher after 14 days.

<Activity analysis for transferase: hexokinase: Tables 20 to 23>

Hexokinase is an enzyme that contributes to a reaction of phosphorylating a hexose such as glucose in the presence of ATP and thereby producing a hexose-6-phosphoric acid. Its activity was measured by quantitatively determining the amount of NADPH (reduced form of nicotinamide adenine dinucleotide phosphate) that had been produced as a result of a reaction between glucose decomposed by hexokinase, and ATP.

First, 0.6 mL of a 50 mM Tris buffer solution at pH 8.5, 0.3 mL of a 10 mM glucose solution, a 4 mM ATP solution at pH 7.0, 0.3 mL of a 10 U/mL G6PDH (glucose-6-phosphate dehydrogenase) solution, 0.3 mL of a 1 mM NADP (oxidized form of nicotinamide adenine dinucleotide phosphate) solution, 0.3 mL of a 10 mM magnesium chloride solution, and 0.9 mL of ion-exchanged water were introduced into a 10-mL screw tube, and thus a substrate solution was prepared. Then, this substrate solution was preliminarily warmed to 37° C. for about 30 minutes. For the 10 U/mL G6PDH, a product produced by dissolving 1000 units (U) of G6PDH (derived from bread yeast, Sigma-Aldrich Company) in 100 mL of a 10 mM Tris buffer solution at pH 8.0 was used.

Next, samples (compounds 3 to 6, 10, 11, 13, 18, 22, 23, 27, and 35 to 41) that had been left to stand at the set concentrations and temperatures described in Tables 20 to 23 for a predetermined time period were each added to the above-mentioned substrate solution such that the amount of enzyme would be 0.05 mg, and the mixtures were allowed to react for 1 minute at 25° C.

After the reaction, the absorbances at 340 nm of the substrate solution as a blank and the reaction solution were measured, and the amount of NADPH was quantitatively determined by the following expression.

Concentration (mM)=(Absorbance of reaction solution–absorbance of blank)/6.22×·×·Millimolar molecular extinction coefficient (L/(mM·cm)) at 340 nm of NADPH Meanwhile, the value of the enzyme activity that served as a reference for the enzyme activity retention ratio was calculated as follows. Hexokinase that had been stored at an appropriate temperature was dissolved in a buffer (50 mM Tris buffer solution adjusted to pH 8.5), and thus an enzyme solution having an enzyme concentration of 10.0 mg/mL was prepared. After the preparation, the solution was immediately added to the substrate solution as described above such that the amount of enzyme would be 0.05 mg, and an enzymatic reaction was induced thereby. Subsequently, the enzyme activity retention ratio was calculated based on the amount of NADPH calculated by a method similar to that described above, as a reference.

The results are presented in Tables 20 to 23.

TABLE 20

Hexokinase: 25° C.

Biocatalyst solvent $$R_4\text{—}^+\!N(R_1)(R_3)\text{—}R_2 \quad X^-$$

| | Compound | $R_1$ | $R_2$ | $R_3$ | $R_4$ | $X^-$ |
|---|---|---|---|---|---|---|
| Example 3 | 3 | $(CH_2)_2OH$ | $(CH_2)_2OH$ | $(CH_2)_2OH$ | H | $CH_3COO^-$ |
| Example 4 | 4 | | | | | $CH_3CH(OH)COO^-$ |
| Example 5 | 5 | | | | | $HOOC(CH_2)_2COO^-$ |
| Example 6 | 6 | | | | | Citric acid |
| Example 10 | 10 | $HOCH_2\text{—}C(CH_2OH)(CH_2OH)\text{—}$ | H | H | H | $CH_3CH(OH)COO^-$ |
| Example 11 | 11 | | | | | Citric acid |
| Example 13 | 13 | | | | | $CH_3SO_3^-$ |
| Example 18 | 18 | $HOCH_2CH(OH)CH(OH)CH(OH)CH_2\text{—}$ | H | H | H | $CH_3\text{—}O\text{—}CH_2COO^-$ |
| Example 22 | 22 | $CH_3$ | $CH_3$ | $CH_3$ | $(CH_2)_2OH$ | $H_2PO_4^-$ |
| Example 23 | 23 | $CH_3$ | $CH_3$ | $CH_3CH_2$ | $(CH_2)_2OH$ | $CH_3COO^-$ |
| Example 27 | 27 | $CH_3$ | $CH_3$ | $CH_3CH_2$ | $(CH_2)_2COOH$ | $CH_3SO_3^-$ |

| | Aqueous solution concentration | Enzyme concentration (mg/mL) | Enzyme activity retention ratio (%) Storage period | | | |
|---|---|---|---|---|---|---|
| | | | After 1 day | After 7 days | After 14 days | After 21 days |
| Example 3 | — | 50.0 | 100 | 64 | 57 | 10 |
| Example 4 | — | 65.0 | 94 | 62 | 57 | 16 |
| Example 5 | — | 50.0 | 95 | 64 | 53 | 10 |
| Example 6 | — | 50.0 | 95 | 69 | 59 | 10 |
| Example 10 | — | 65.0 | 94 | 66 | 59 | 13 |
| Example 11 | — | 50.0 | 93 | 62 | 56 | 10 |
| Example 13 | — | 50.0 | 100 | 62 | 56 | 11 |
| Example 18 | — | 50.0 | 98 | 65 | 56 | 11 |
| Example 22 | — | 10.0 | 83 | 76 | 55 | 11 |
| Example 23 | — | 40.0 | 94 | 70 | 55 | 10 |
| Example 27 | — | 10.0 | 85 | 69 | 56 | 10 |

TABLE 21

Hexokinase: 25° C.

Biocatalyst solvent $$R_4\text{—}^+\!N(R_1)(R_3)\text{—}R_2 \quad X^-$$

| | Compound | $R_1$ | $R_2$ | $R_3$ | $R_4$ | $X^-$ | Aqueous solution concentration |
|---|---|---|---|---|---|---|---|
| Comparative Example 8 | 35 | Glycerin | | | | | 100% |
| Comparative Example 9 | 36 | Buffer | | | | | 10 mM |
| Comparative Example 10 | 37 | Aqueous solution of glycerin | | | | | 10 mg/mL |
| Comparative Example 11 | 38 | Aqueous solution of glucose | | | | | 10 mg/mL |
| Comparative Example 12 | 39 | Aqueous solution of bovine serum albumin | | | | | 10 mg/mL |
| Comparative Example 13 | 40 | Aqueous solution of lysine | | | | | 10 mg/mL |
| Comparative Example 14 | 41 | Aqueous solution of lysine and bovine serum albumin | | | | | 10 mg/mL |

TABLE 21-continued

Hexokinase: 25° C.

| | Enzyme concentration (mg/mL) | Enzyme activity retention ratio (%) Storage period | | | |
|---|---|---|---|---|---|
| | | After 1 day | After 7 days | After 14 days | After 21 days |
| Comparative Example 8 | 1.0 | 10 | 0 | 0 | 0 |
| Comparative Example 9 | 10.0 | 48 | 36 | 6 | 0 |
| Comparative Example 10 | 10.0 | 58 | 0 | 0 | 0 |
| Comparative Example 11 | 10.0 | 39 | 35 | 5 | 0 |
| Comparative Example 12 | 10.0 | 58 | 31 | 1 | 0 |
| Comparative Example 13 | 10.0 | 4 | 0 | 0 | 0 |
| Comparative Example 14 | 10.0 | 1 | 0 | 0 | 0 |

TABLE 22

Hexokinase: 40° C.

Biocatalyst solvent $$R_4 - \overset{R_1}{\underset{R_3}{\overset{|}{\underset{|}{N^+}}}} - R_2 \quad X^-$$

| | Compound | $R_1$ | $R_2$ | $R_3$ | $R_4$ | $X^-$ |
|---|---|---|---|---|---|---|
| Example 3 | 3 | $(CH_2)_2OH$ | $(CH_2)_2OH$ | $(CH_2)_2OH$ | H | $CH_3COO^-$ |
| Example 4 | 4 | | | | | $CH_3CH(OH)COO^-$ |
| Example 5 | 5 | | | | | $HOOC(CH_2)_2COO^-$ |
| Example 6 | 6 | | | | | Citric acid |
| Example 10 | 10 | $HOCH_2-\underset{\underset{CH_2OH}{|}}{\overset{\overset{CH_2OH}{|}}{C}}-$ | H | H | H | $CH_3CH(OH)COO^-$ |
| Example 11 | 11 | | | | | Citric acid |
| Example 13 | 13 | | | | | $CH_3SO_3^-$ |
| Example 18 | 18 | $HOCH_2\underset{\underset{OH}{|}}{C}H\underset{\underset{OH}{|}}{C}HCH CHCH_2-$ (with OH OH above) | H | H | H | $CH_3-O-CH_2COO^-$ |
| Example 22 | 22 | $CH_3$ | $CH_3$ | $CH_3$ | $(CH_2)_2OH$ | $H_2PO_4^-$ |
| Example 23 | 23 | $CH_3$ | $CH_3$ | $CH_3CH_2$ | $(CH_2)_2OH$ | $CH_3COO^-$ |
| Example 27 | 27 | $CH_3$ | $CH_3$ | $CH_3CH_2$ | $(CH_2)_2COOH$ | $CH_3SO_3^-$ |

| | Biocatalyst solvent Aqueous solution concentration | Enzyme concentration (mg/mL) | Enzyme activity retention ratio (%) Storage period | | |
|---|---|---|---|---|---|
| | | | After 1 day | After 7 days | After 14 days |
| Example 3 | — | 50.0 | 50 | 41 | 23 |
| Example 4 | — | 65.0 | 54 | 45 | 28 |
| Example 5 | — | 50.0 | 49 | 40 | 27 |
| Example 6 | — | 50.0 | 49 | 38 | 24 |
| Example 10 | — | 65.0 | 53 | 43 | 20 |
| Example 11 | — | 50.0 | 53 | 49 | 29 |
| Example 13 | — | 50.0 | 50 | 40 | 20 |
| Example 18 | — | 50.0 | 57 | 45 | 20 |
| Example 22 | — | 10.0 | 53 | 45 | 22 |
| Example 23 | — | 40.0 | 51 | 39 | 19 |
| Example 27 | — | 10.0 | 45 | 43 | 20 |

TABLE 23

Hexokinase: 40° C.

| | Compound | Biocatalyst solvent $R_4\text{—}^+N(R_1)(R_3)\text{—}R_2\ X^-$ | Aqueous solution concentration | Enzyme concentration (mg/mL) | Enzyme activity retention ratio (%) Storage period After 1 day | After 7 days | After 14 days |
|---|---|---|---|---|---|---|---|
| Comparative Example 8 | 35 | Glycerin | 100% | 1.0 | 10 | 2 | 0 |
| Comparative Example 9 | 36 | Buffer | 10 mM | 10.0 | 8 | 0 | 0 |
| Comparative Example 10 | 37 | Aqueous solution of glycerin | 10 mg/mL | 10.0 | 6 | 0 | 0 |
| Comparative Example 11 | 38 | Aqueous solution of glucose | 10 mg/mL | 10.0 | 2 | 0 | 0 |
| Comparative Example 12 | 39 | Aqueous solution of bovine serum albumin | 10 mg/mL | 10.0 | 9 | 0 | 0 |
| Comparative Example 13 | 40 | Aqueous solution of lysine | 10 mg/mL | 10.0 | 16 | 7 | 0 |
| Comparative Example 14 | 41 | Aqueous solution of lysine and bovine serum albumin | 10 mg/mL | 10.0 | 12 | 5 | 0 |

The ionic liquids of the present invention (compounds 3 to 6, 10, 11, 13, 18, 22, 23, and 27) retained, under the conditions of 25° C. (Tables 20 and 21), a catalytic activity of 10% or higher after 21 days, while in Comparative Examples 8 to 14 (compounds 35 to 41), the catalytic activity was 0%. Furthermore, under the conditions of 40° C. (Tables 22 and 23), the ionic liquids of the present invention retained a catalytic activity of 19% or higher after 14 days, while in the Comparative Examples, the catalytic activity became 0%. Thus, the ionic liquids of the present invention showed superiority.

<Activity Analysis for Lyase: Alginate Lyase: Tables 24 to 27>

Alginate lyase is an enzyme that contributes to a decomposition reaction for alginic acid. Since a sugar having double bonds that are produced as alginate lyase decomposes alginic acid, exhibits a specific change in the absorbance at 235 nm, the activity was measured by quantitatively determining the amount of this product.

First, 1.0 mL of a 0.2% aqueous solution of alginic acid, 0.5 mL of a 200 mM Tris buffer solution at pH 7.0, and 0.5 mL of ion-exchanged water were introduced into a 10-mL screw tube, and thus a substrate solution was prepared. This substrate solution was preliminarily warmed to 25° C. for about 30 minutes.

Next, samples (compounds 3 to 6, 10, 11, 13, 18, 22, 23, 27, and 35 to 41) that had been left to stand at the set concentrations and temperatures described in Tables 24 to 27 for a predetermined time period were each added to the above-mentioned substrate solution such that the amount of enzyme would be 0.03 mg, and the mixtures were allowed to react for 5 minutes at 25° C.

After the reaction, the absorbances at 235 nm of the substrate solution as a blank and the reaction solution were measured, the amount of the product was quantitatively determined, and thereby the alginate lyase activity was calculated. The amount of the product was calculated using a calibration curve produced using solutions in the concentration range of 0.01% to 0.2%.

Meanwhile, the value of the enzyme activity that served as a reference for the enzyme activity retention ratio was calculated as follows. An alginate lyase powder that had been stored at an appropriate temperature was dissolved in a buffer (200 mM Tris buffer solution at pH 7.0), and an enzyme solution having an enzyme concentration of 10.0 mg/mL was prepared. After the preparation, the solution was immediately added to the substrate solution as described above such that the amount of enzyme would be 0.03 mg, and an enzyme reaction was induced thereby. Subsequently, the enzyme activity was calculated based on the absorbance calculated by a method similar to that described above, as a reference.

The results are presented in Tables 24 to 27.

TABLE 24

Alginate lyase: 25° C.

| | Compound | Biocatalyst solvent $R_4\text{—}^+N(R_1)(R_3)\text{—}R_2\ X^-$ $R_1$ | $R_2$ | $R_3$ | $R_4$ | $X^-$ | Aqueous solution concentration |
|---|---|---|---|---|---|---|---|
| Example 3 | 3 | $(CH_2)_2OH$ | $(CH_2)_2OH$ | $(CH_2)_2OH$ | H | $CH_3COO^-$ | — |
| Example 4 | 4 | | | | | $CH_3CH(OH)COO^-$ | — |

TABLE 24-continued

Alginate lyase: 25° C.

| | | | | | | | |
|---|---|---|---|---|---|---|---|
| Example 5 | 5 | | | | | HOOC(CH$_2$)$_2$COO$^-$ | — |
| Example 6 | 6 | | | | | Citric acid | — |
| Example 10 | 10 | CH$_2$OH \| HOCH$_2$—C— \| CH$_2$OH | H | H | H | CH$_3$CH(OH)COO$^-$ | — |
| Example 11 | 11 | | | | | Citric acid | — |
| Example 13 | 13 | | | | | CH$_3$SO$_3^-$ | — |
| Example 18 | 18 | OH OH \| \| HOCH$_2$CHCHCHCHCH$_2$— \| \| OH OH | H | H | H | CH$_3$—O—CH$_2$COO$^-$ | — |
| Example 22 | 22 | CH$_3$ | CH$_3$ | CH$_3$ | (CH$_2$)$_2$OH | H$_2$PO$_4^-$ | — |
| Example 23 | 23 | CH$_3$ | CH$_3$ | CH$_3$CH$_2$ | (CH$_2$)$_2$OH | CH$_3$COO$^-$ | — |
| Example 27 | 27 | CH$_3$ | CH$_3$ | CH$_3$CH$_2$ | (CH$_2$)$_2$COOH | CH$_3$SO$_3^-$ | — |

| | Enzyme concentration | Enzyme activity retention ratio (%) Storage period | | | | | |
|---|---|---|---|---|---|---|---|
| | (mg/mL) | After 1 day | After 7 days | After 14 days | After 21 days | After 30 days | After 60 days |
| Example 3 | 20.0 | 100 | 100 | 100 | 100 | 100 | 44 |
| Example 4 | 30.0 | 100 | 100 | 100 | 100 | 100 | 100 |
| Example 5 | 25.0 | 100 | 100 | 100 | 100 | 100 | 24 |
| Example 6 | 20.0 | 100 | 100 | 100 | 100 | 99 | 26 |
| Example 10 | 30.0 | 100 | 100 | 100 | 100 | 100 | 100 |
| Example 11 | 20.0 | 100 | 100 | 100 | 100 | 94 | 35 |
| Example 13 | 25.0 | 100 | 100 | 100 | 100 | 100 | 34 |
| Example 18 | 25.0 | 100 | 100 | 100 | 100 | 100 | 100 |
| Example 22 | 10.0 | 100 | 100 | 100 | 100 | 100 | 24 |
| Example 23 | 15.0 | 100 | 100 | 100 | 100 | 98 | 20 |
| Example 27 | 15.0 | 100 | 100 | 100 | 100 | 83 | 20 |

TABLE 25

Alginate lyase: 25° C.

| | | Biocatalyst solvent | | | | | | | | Enzyme activity retention ratio (%) Storage period | | | | | |
|---|---|---|---|---|---|---|---|---|---|---|---|---|---|---|---|
| | | $R_4$—$^+$N—$R_2$  X$^-$ (with $R_1$, $R_3$) | | | | | | Aqueous solution | Enzyme concentration | After 1 day | After 7 days | After 14 days | After 21 days | After 30 days | After 60 days |
| | Compound | $R_1$ | $R_2$ | $R_3$ | $R_4$ | X$^-$ | concentration | | (mg/mL) | | | | | | |
| Comparative Example 8 | 35 | | | | | | | Glycerin | 100% | 5.0 | 84 | 56 | 55 | 8 | 0 | 0 |
| Comparative Example 9 | 36 | | | | | | | Buffer | 10 mM | 10.0 | 98 | 89 | 85 | 58 | 0 | 0 |
| Comparative Example 10 | 37 | | | | | | | Aqueous solution of glycerin | 10 mg/mL | 10.0 | 97 | 51 | 0 | 0 | 0 | 0 |
| Comparative Example 11 | 38 | | | | | | | Aqueous solution of glucose | 10 mg/mL | 10.0 | 97 | 85 | 0 | 0 | 0 | 0 |
| Comparative Example 12 | 39 | | | | | | | Aqueous solution of bovine serum albumin | 10 mg/mL | 10.0 | 84 | 68 | 0 | 0 | 0 | 0 |
| Comparative Example 13 | 40 | | | | | | | Aqueous solution of lysine | 10 mg/mL | 10.0 | 85 | 70 | 0 | 0 | 0 | 0 |
| Comparative Example 14 | 41 | | | | | | | Aqueous solution of lysine and bovine serum albumin | 10 mg/mL | 10.0 | 84 | 61 | 53 | 0 | 0 | 0 |

TABLE 26

Alginate lyase: 40° C.

Biocatalyst solvent $$R_4 - \overset{R_1}{\underset{R_3}{\overset{|}{N^+}}} - R_2 \quad X^-$$

| Compound | | $R_1$ | $R_2$ | $R_3$ | $R_4$ | $X^-$ | Aqueous solution concentration |
|---|---|---|---|---|---|---|---|
| Example 3 | 3 | $(CH_2)_2OH$ | $(CH_2)_2OH$ | $(CH_2)_2OH$ | H | $CH_3COO^-$ | — |
| Example 4 | 4 | | | | | $CH_3CH(OH)COO^-$ | — |
| Example 5 | 5 | | | | | $HOOC(CH_2)_2COO^-$ | — |
| Example 6 | 6 | | | | | Citric acid | — |
| Example 10 | 10 | $HOCH_2-\underset{\underset{CH_2OH}{\|}}{\overset{\overset{CH_2OH}{\|}}{C}}-$ | H | H | H | $CH_3CH(OH)COO^-$ | — |
| Example 11 | 11 | | | | | Citric acid | — |
| Example 13 | 13 | | | | | $CH_3SO_3^-$ | — |
| Example 18 | 18 | $HOCH_2\underset{\underset{OH}{\|}}{CH}\underset{}{CH}\underset{\underset{OH}{\|}}{CH}CH_2-$ OH OH | H | H | H | $CH_3-O-CH_2COO^-$ | — |
| Example 22 | 22 | $CH_3$ | $CH_3$ | $CH_3$ | $(CH_2)_2OH$ | $H_2PO_4^-$ | — |
| Example 23 | 23 | $CH_3$ | $CH_3$ | $CH_3CH_2$ | $(CH_2)_2OH$ | $CH_3COO^-$ | — |
| Example 27 | 27 | $CH_3$ | $CH_3$ | $CH_3CH_2$ | $(CH_2)_2COOH$ | $CH_3SO_3^-$ | — |

| | Enzyme concentration (mg/mL) | Enzyme activity retention ratio (%) Storage period | | | | |
|---|---|---|---|---|---|---|
| | | After 1 day | After 7 days | After 14 days | After 21 days | After 30 days |
| Example 3 | 20.0 | 72 | 53 | 34 | 34 | 23 |
| Example 4 | 30.0 | 95 | 64 | 35 | 35 | 14 |
| Example 5 | 25.0 | 72 | 54 | 35 | 34 | 18 |
| Example 6 | 20.0 | 72 | 54 | 34 | 27 | 20 |
| Example 10 | 30.0 | 94 | 78 | 55 | 51 | 15 |
| Example 11 | 20.0 | 71 | 71 | 36 | 34 | 20 |
| Example 13 | 25.0 | 70 | 70 | 35 | 35 | 14 |
| Example 18 | 25.0 | 62 | 52 | 41 | 37 | 19 |
| Example 22 | 10.0 | 72 | 54 | 38 | 35 | 15 |
| Example 23 | 15.0 | 74 | 56 | 35 | 30 | 13 |
| Example 27 | 15.0 | 74 | 55 | 33 | 34 | 15 |

TABLE 27

Alginate lyase: 40° C.

| | | Biocatalyst solvent | | | | | | | Enzyme activity retention ratio (%) Storage period | | | | |
|---|---|---|---|---|---|---|---|---|---|---|---|---|---|
| | | $R_4-\overset{R_1}{\underset{R_3}{\overset{\|}{N^+}}}-R_2 \quad X^-$ | | | | | | | | | | | |
| | Compound | $R_1$ | $R_2$ | $R_3$ | $R_4$ | $X^-$ | Aqueous solution concentration | Enzyme concentration (mg/mL) | After 1 day | After 7 days | After 14 days | After 21 days | After 30 days |
| Comparative Example 8 | 35 | Glycerin | | | | | 100% | 5.0 | 2 | 0 | 0 | 0 | 0 |
| Comparative Example 9 | 36 | Buffer | | | | | 10 mM | 10.0 | 3 | 0 | 0 | 0 | 0 |
| Comparative Example 10 | 37 | Aqueous solution of glycerin | | | | | 10 mg/mL | 10.0 | 58 | 0 | 0 | 0 | 0 |
| Comparative Example 11 | 38 | Aqueous solution of glucose | | | | | 10 mg/mL | 10.0 | 63 | 1 | 0 | 0 | 0 |
| Comparative Example 12 | 39 | Aqueous solution of bovine serum albumin | | | | | 10 mg/mL | 10.0 | 60 | 0 | 0 | 0 | 0 |

TABLE 27-continued

Alginate lyase: 40° C.

| | | Biocatalyst solvent | | | | | | Enzyme activity retention ratio (%) Storage period | | | | |
|---|---|---|---|---|---|---|---|---|---|---|---|---|
| | | $R_4 - \overset{\overset{R_1}{\mid}}{\underset{\underset{R_3}{\mid}}{N^+}} - R_2 \quad X^-$ | | | | | | | | | | |
| | | | | | | | Aqueous solution | Enzyme concentration | After 1 | After 7 | After 14 | After 21 | After 30 |
| Compound | $R_1$ | $R_2$ | $R_3$ | $R_4$ | $X^-$ | concentration | (mg/mL) | day | days | days | days | days |
| Comparative Example 13 | 40 | Aqueous solution of lysine | | | | | 10 mg/mL | 10.0 | 1 | 0 | 0 | 0 | 0 |
| Comparative Example 14 | 41 | Aqueous solution of lysine and bovine serum albumin | | | | | 10 mg/mL | 10.0 | 1 | 0 | 0 | 0 | 0 |

The ionic liquids of the present invention (compounds 3 to 6, 10, 11, 13, 18, 22, 23, and 27) retained, under the conditions of 25° C. (Tables 24 and 25), a catalytic activity of 20% or higher after 60 days. Particularly, compounds 4, 10 and 18 retained a high activity of 100%. In contrast, in Comparative Examples 8 to 14 (compounds 35 to 41), the catalytic activity was 0%. Furthermore, under the conditions at 40° C. (Tables 26 and 27), the ionic liquids of the present invention retained a catalytic activity of 13% or higher after 30 days, while in Comparative Examples, the catalytic activity became 0%. Thus, the ionic liquids of the present invention showed superiority.

<Activity Analysis for Isomerase: Phosphoglucose Isomerase: Tables 28 and 29>

Phosphoglucose isomerase is an enzyme that converts glucose into fructose. Its activity was measured by quantitatively determining the amount of fructose produced by phosphoglucose isomerase.

First, the following solutions were prepared.

A: 200 mM glucose solution (produced by dissolving glucose in 90 mL of a 200 mM phosphate buffer solution at pH 7.2 and 10 mL of a 100 mM magnesium sulfate solution)

B: 200 mM phosphate buffer solution (pH 7.2)

C: 500 mM aqueous solution of perchloric acid

D: 1.5% aqueous solution of cysteine

E: 70% aqueous solution of sulfuric acid

F: 0.12% ethanol solution of carbazole

Subsequently 1.0 mL of A was collected in a 10-mL screw tube as a substrate solution, and this was preliminarily warmed to 60° C. for about 30 minutes. Next, samples (compounds 3 to 6, 10, 11, 13, 18, 22, 23, and 27) that had been left to stand at the set concentrations and temperatures described in Tables 28 and 29 for a predetermined time period were added to the above-mentioned substrate solution such that the amount of enzyme would be 0.03 mg. 1.0 mL of B was added thereto, and the mixture was allowed to react for 60 minutes at 60° C. After the reaction, 2.0 mL of C was added thereto, and the mixture was cooled and diluted to 50 mL in a measuring cylinder. 1.0 mL of this solution was collected, and 0.2 mL of D and 6.0 mL of E were added thereto. The mixture was mixed by shaking, and the solution was cooled. Subsequently, 0.2 mL of F was added thereto, and the mixture was allowed to react for 10 minutes at 60° C.

After the reaction, the absorbance at 560 nm of a blank solution that had been subjected to the operation described about without adding an enzyme solution, and the absorbance of the reaction solution were measured, the amount of fructose was quantitatively determined, and thus the phosphoglucose isomerase activity was calculated. The amount of fructose was calculated using a calibration curve produced based on the absorbances measured by performing the above-described operation using fructose solutions (prepared by dissolving fructose in a 200 mM phosphate buffer solution at pH 7.2, and adjusting the solution to predetermined concentrations) in the concentration range of 1 to 200 mM, without adding an enzyme solution.

The value of the enzyme activity that served as a reference for the enzyme activity retention ratio was calculated as follows. Phosphoglucose isomerase that had been stored at an appropriate temperature was dissolved in a buffer (200 mM phosphate buffer solution at pH 7.2), and an enzyme solution having an enzyme concentration of 1.5 mg/mL was prepared. After the preparation, the solution was immediately added to the substrate solution as described above such that the amount of enzyme would be 0.03 mg, and an enzyme reaction was induced thereby. Subsequently, the enzyme activity retention ratio was calculated based on the amount of fructose calculated by a method similar to that described above, as a reference.

The results are presented in Tables 28 and 29.

TABLE 28

Phosphoglucose isomerase: 25° C.

| | | Biocatalyst solvent $R_4-\overset{R_1}{\underset{R_3}{\overset{|}{N^+}}}-R_2\ X^-$ | | | | | Aqueous solution concentration |
|---|---|---|---|---|---|---|---|
| Compound | | $R_1$ | $R_2$ | $R_3$ | $R_4$ | $X^-$ | |
| Example 3 | 3 | (CH$_2$)$_2$OH | (CH$_2$)$_2$OH | (CH$_2$)$_2$OH | H | CH$_3$COO$^-$ | — |
| Example 4 | 4 | | | | | CH$_3$CH(OH)COO$^-$ | — |
| Example 5 | 5 | | | | | HOOC(CH$_2$)$_2$COO$^-$ | — |
| Example 6 | 6 | | | | | Citric acid | — |
| Example 10 | 10 | HOCH$_2$-C(CH$_2$OH)(CH$_2$OH)- | H | H | H | CH$_3$CH(OH)COO$^-$ | — |
| Example 11 | 11 | | | | | Citric acid | — |
| Example 13 | 13 | | | | | CH$_3$SO$_3^-$ | — |
| Example 18 | 18 | HOCH$_2$CH(OH)CH(OH)CH(OH)CH$_2$- | H | H | H | CH$_3$-O-CH$_2$COO$^-$ | — |
| Example 22 | 22 | CH$_3$ | CH$_3$ | CH$_3$ | (CH$_2$)$_2$OH | H$_2$PO$_4^-$ | — |
| Example 23 | 23 | CH$_3$ | CH$_3$ | CH$_3$CH$_2$ | (CH$_2$)$_2$OH | CH$_3$COO$^-$ | — |
| Example 27 | 27 | CH$_3$ | CH$_3$ | CH$_3$CH$_2$ | (CH$_2$)$_2$COOH | CH$_3$SO$_3^-$ | — |

| | Enzyme concentration (mg/mL) | Enzyme activity retention ratio (%) Storage period | | | | | |
|---|---|---|---|---|---|---|---|
| | | After 1 days | After 7 days | After 14 days | After 21 days | After 60 days | After 60 days |
| Example 3 | 1.5 | 100 | 100 | 100 | 100 | 85 | 68 |
| Example 4 | 1.5 | 100 | 100 | 100 | 100 | 88 | 68 |
| Example 5 | 1.5 | 100 | 100 | 100 | 100 | 88 | 64 |
| Example 6 | 1.5 | 100 | 100 | 100 | 100 | 90 | 69 |
| Example 10 | 1.5 | 100 | 100 | 100 | 100 | 90 | 70 |
| Example 11 | 1.5 | 100 | 100 | 100 | 100 | 86 | 66 |
| Example 13 | 1.5 | 100 | 100 | 100 | 100 | 88 | 70 |
| Example 18 | 1.5 | 100 | 100 | 100 | 100 | 85 | 67 |
| Example 22 | 1.5 | 100 | 100 | 100 | 100 | 86 | 63 |
| Example 23 | 1.5 | 100 | 100 | 100 | 100 | 91 | 75 |
| Example 27 | 1.5 | 100 | 100 | 100 | 100 | 80 | 61 |

TABLE 29

Phosphoglucose isomerase: 40° C.

| | | Biocatalyst solvent $R_4-\overset{R_1}{\underset{R_3}{\overset{|}{N^+}}}-R_2\ X^-$ | | | | | Aqueous solution concentration |
|---|---|---|---|---|---|---|---|
| | Compound | $R_1$ | $R_2$ | $R_3$ | $R_4$ | $X^-$ | |
| Example 3 | 3 | (CH$_2$)$_2$OH | (CH$_2$)$_2$OH | (CH$_2$)$_2$OH | H | CH$_3$COO$^-$ | — |
| Example 4 | 4 | | | | | CH$_3$CH(OH)COO$^-$ | — |
| Example 5 | 5 | | | | | HOOC(CH$_2$)$_2$COO$^-$ | — |
| Example 6 | 6 | | | | | Citric acid | — |

TABLE 29-continued

Phosphoglucose isomerase: 40° C.

| | | | | | | | |
|---|---|---|---|---|---|---|---|
| Example 10 | 10 | CH₂OH<br>\|<br>HOCH₂—C—<br>\|<br>CH₂OH | H | H | H | CH₃CH(OH)COO⁻ | — |
| Example 11 | 11 | | | | | Citric acid | — |
| Example 13 | 13 | | | | | CH₃SO₃⁻ | — |
| Example 18 | 18 | OH  OH<br>\|   \|<br>HOCH₂CHCHCHCHCH₂—<br>\|   \|<br>OH  OH | H | H | H | CH₃—O—CH₂COO⁻ | — |
| Example 22 | 22 | CH₃ | CH₃ | CH₃ | (CH₂)₂OH | H₂PO₄⁻ | — |
| Example 23 | 23 | CH₃ | CH₃ | CH₃CH₂ | (CH₂)₂OH | CH₃COO⁻ | — |
| Example 27 | 27 | CH₃ | CH₃ | CH₃CH₂ | (CH₂)₂COOH | CH₃SO₃⁻ | — |

| | Enzyme concentration (mg/mL) | Enzyme activity retention ratio (%)<br>Storage period | | | |
|---|---|---|---|---|---|
| | | After 1 day | After 7 days | After 14 days | After 21 days |
| Example 3 | 1.5 | 100 | 70 | 40 | 11 |
| Example 4 | 1.5 | 100 | 73 | 48 | 10 |
| Example 5 | 1.5 | 100 | 74 | 48 | 12 |
| Example 6 | 1.5 | 100 | 71 | 48 | 11 |
| Example 10 | 1.5 | 100 | 72 | 47 | 13 |
| Example 11 | 1.5 | 100 | 66 | 39 | 10 |
| Example 13 | 1.5 | 100 | 63 | 45 | 15 |
| Example 18 | 1.5 | 100 | 69 | 42 | 12 |
| Example 22 | 1.5 | 100 | 70 | 43 | 10 |
| Example 23 | 1.5 | 100 | 72 | 45 | 11 |
| Example 27 | 1.5 | 100 | 60 | 38 | 10 |

The ionic liquids of the present invention (compounds 3 to 6, 10, 11, 13, 18, 22, 23, and 27) retained, under the conditions of 25° C. (Table 28), a catalytic activity of 61% or higher after 60 days, and under the conditions of 40° C. (Table 29), a catalytic activity of 10% or higher after 21 days.

<Activity Analysis for Ligase: Acetyl-CoA Synthetase: Tables 30 and 31>

Acetyl-CoA synthetase is an enzyme that catalyzes a reaction of synthesizing acetyl-CoA from coenzyme A (CoA) and acetic acid using the energy of ATP. Its activity was measured by quantitatively determining the amount of acetic acid, which is a reaction substrate of acetyl-CoA synthetase.

For the measurement of the acetyl-CoA synthetase activity, F-Kit Acetic Acid (Roche) was used. 300 μL of Solution I (triethanolamine buffer solution (pH 8.4), L-malic acid, and magnesium chloride solution), 60 μL of Solution II (ATP, CoA, and NAD solution), 3 μL of Solution III (malate dehydrogenase and citrate synthase solution), ion-exchanged water, and each of samples (compounds 3 to 6, 10, 11, 13, 18, 22, 23, and 27) that had been left to stand at the set concentrations and temperatures described in Tables 30 and 31 for a predetermined time period, were added to the above-mentioned substrate solution such that the amount of enzyme would be 0.03 mg. The total amount was adjusted to 900 μL, and the mixture was preliminarily warmed to 30° C. for about 30 minutes.

Next, 100 μL of a 1 mM potassium acetate solution was added thereto, and the mixture was allowed to react for 30 minutes at 30° C.

After the reaction, the absorbance at 340 nm of a blank solution that had been subjected to the above-described operation without adding an enzyme solution, and the absorbance of the reaction solution were measured, the amount of acetic acid was quantitatively determined, and thus the acetyl-CoA synthetase activity was calculated. The amount of acetic acid was calculated using a calibration curve produced using acetic acid solutions in the concentration range of 0.1 to 1 mM.

Meanwhile, the value of the enzyme activity that served as a reference for the enzyme activity retention ratio was calculated as follows. Acetyl-CoA synthetase that had been stored at an appropriate temperature was dissolved in a buffer (100 mM potassium phosphate buffer solution at pH 7.4), and an enzyme solution having an enzyme concentration of 1.5 mg/mL was prepared. After the preparation, the solution was immediately added to the substrate solution as described above such that the amount of enzyme would be 0.03 mg, and an enzymatic reaction was induced thereby. Subsequently, the enzyme activity retention ratio was calculated based on the amount of acetic acid calculated by a method similar to that described above, as a reference.

The results are presented in Tables 30 and 31.

TABLE 30

Acetyl-CoA synthetase: 25° C.

Biocatalyst solvent $$R_4 - \overset{R_1}{\underset{R_3}{\overset{|}{\underset{|}{N^+}}}} - R_2 \quad X^-$$

| | Compound | $R_1$ | $R_2$ | $R_3$ | $R_4$ | $X^-$ | Aqueous solution concentration |
|---|---|---|---|---|---|---|---|
| Example 3 | 3 | $(CH_2)_2OH$ | $(CH_2)_2OH$ | $(CH_2)_2OH$ | H | $CH_3COO^-$ | — |
| Example 4 | 4 | | | | | $CH_3CH(OH)COO^-$ | — |
| Example 5 | 5 | | | | | $HOOC(CH_2)_2COO^-$ | — |
| Example 6 | 6 | | | | | Citric acid | — |
| Example 10 | 10 | $HOCH_2-\underset{CH_2OH}{\overset{CH_2OH}{\overset{|}{C}}}-$ | H | H | H | $CH_3CH(OH)COO^-$ | — |
| Example 11 | 11 | | | | | Citric acid | — |
| Example 13 | 13 | | | | | $CH_3SO_3^-$ | — |
| Example 18 | 18 | $HOCH_2\underset{OH}{\overset{OH}{\overset{|}{C}H}}\overset{OH}{\overset{|}{C}H}\underset{OH}{\overset{|}{C}H}CH_2-$ | H | H | H | $CH_3-O-CH_2COO^-$ | — |
| Example 22 | 22 | $CH_3$ | $CH_3$ | $CH_3$ | $(CH_2)_2OH$ | $H_2PO_4^-$ | — |
| Example 23 | 23 | $CH_3$ | $CH_3$ | $CH_3CH_2$ | $(CH_2)_2OH$ | $CH_3CO^-$ | — |
| Example 27 | 27 | $CH_3$ | $CH_3$ | $CH_3CH_2$ | $(CH_2)_2COOH$ | $CH_3SO_3^-$ | — |

| | Enzyme concentration (mg/mL) | Enzyme activity retention ratio (%) Storage period | | | | | |
|---|---|---|---|---|---|---|---|
| | | After 1 day | After 7 days | After 14 days | After 21 days | After 30 days | After 60 days |
| Example 3 | 1.5 | 100 | 100 | 100 | 47 | 22 | 12 |
| Example 4 | 1.5 | 100 | 100 | 100 | 58 | 25 | 15 |
| Example 5 | 1.5 | 100 | 100 | 100 | 49 | 20 | 11 |
| Example 6 | 1.5 | 100 | 100 | 100 | 50 | 25 | 13 |
| Example 10 | 1.5 | 100 | 100 | 100 | 59 | 28 | 15 |
| Example 11 | 1.5 | 100 | 100 | 100 | 49 | 21 | 11 |
| Example 13 | 1.5 | 100 | 100 | 100 | 51 | 25 | 10 |
| Example 18 | 1.5 | 100 | 100 | 100 | 54 | 27 | 12 |
| Example 22 | 1.5 | 100 | 100 | 100 | 48 | 18 | 10 |
| Example 23 | 1.5 | 100 | 100 | 100 | 55 | 25 | 16 |
| Example 27 | 1.5 | 100 | 100 | 100 | 45 | 20 | 10 |

TABLE 31

Acetyl-CoA synthetase: 40° C.

Biocatalyst solvent $$R_4 - \overset{R_1}{\underset{R_3}{\overset{|}{\underset{|}{N^+}}}} - R_2 \quad X^-$$

| Compound | $R_1$ | $R_2$ | $R_3$ | $R_4$ | $X^-$ | Aqueous solution concentration |
|---|---|---|---|---|---|---|
| Example 3 | 3 | $(CH_2)_2OH$ | $(CH_2)_2OH$ | $(CH_2)_2OH$ | H | $CH_3COO^-$ | — |
| Example 4 | 4 | | | | | $CH_3CH(OH)COO^-$ | — |
| Example 5 | 5 | | | | | $HOOC(CH_2)_2COO^-$ | — |
| Example 6 | 6 | | | | | Citric acid | — |

TABLE 31-continued

Acetyl-CoA synthetase: 40° C.

| Example | # | | | | | | |
|---|---|---|---|---|---|---|---|
| Example 10 | 10 | CH₂OH<br>\|<br>HOCH₂—C—<br>\|<br>CH₂OH | H | H | H | CH₃CH(OH)COO⁻ | — |
| Example 11 | 11 | | | | | Citric acid | — |
| Example 13 | 13 | | | | | CH₃SO₃⁻ | — |
| Example 18 | 18 | OH  OH<br>\|    \|<br>HOCH₂CHCHCHCHCH₂—<br>\|    \|<br>OH  OH | H | H | H | CH₃—O—CH₂COO⁻ | — |
| Example 22 | 22 | CH₃ | CH₃ | CH₃ | (CH₂)₂OH | H₂PO₄⁻ | — |
| Example 23 | 23 | CH₃ | CH₃ | CH₃CH₂ | (CH₂)₂OH | CH₃COO⁻ | — |
| Example 27 | 27 | CH₃ | CH₃ | CH₃CH₂ | (CH₂)₂COOH | CH₃SO₃⁻ | — |

| | Enzyme concentration (mg/mL) | Enzyme activity retention ratio (%) Storage period | | |
|---|---|---|---|---|
| | | After 1 day | After 7 days | After 14 days |
| Example 3 | 1.5 | 100 | 60 | 34 |
| Example 4 | 1.5 | 100 | 60 | 30 |
| Example 5 | 1.5 | 100 | 60 | 32 |
| Example 6 | 1.5 | 100 | 60 | 31 |
| Example 10 | 1.5 | 100 | 62 | 31 |
| Example 11 | 1.5 | 100 | 59 | 24 |
| Example 13 | 1.5 | 100 | 56 | 25 |
| Example 18 | 1.5 | 100 | 64 | 28 |
| Example 22 | 1.5 | 100 | 55 | 24 |
| Example 23 | 1.5 | 100 | 65 | 30 |
| Example 27 | 1.5 | 100 | 55 | 21 |

The ionic liquids of the present invention (compounds 3 to 6, 10, 11, 13, 18, 22, 23, and 27) retained, under the conditions of 25° C. (Table 30), a catalytic activity of 10% or higher after 60 days, and under the conditions of 40° C. (Table 31), a catalytic activity of 21% or higher after 14 days.

<Activity Analysis for Oxidoreductase: Cytochrome P450: Table 32>

The activity of cytochrome P450 was measured by quantitatively determining, by HPLC, the amount of 6β-hydroxytestosterone, which is produced by an enzymatic reaction of cytochrome P450 from its substrate testosterone.

890 μL of a 0.1 M potassium phosphate buffer at pH 7.4, 10 μL of a methanol solution of testosterone at 3200 nmol/L, and 100 μL of an aqueous solution of NADPH (reduced form of nicotinamide adenine dinucleotide phosphate) at 3200 nmol/L were introduced into a conical flask, and the mixture was placed in a thermostatic chamber at 37° C. and preliminarily warmed for 3 minutes.

Next, samples (compounds 3 to 6, 10, 13, 15, 18, 20, 22, 29, 36, and 43) that had been stored at the set concentrations and temperatures described in Table 32 for a predetermined time period, were each added to the above-described substrate solution such that the amount of enzyme would be 1.0 μg, and the mixtures were allowed to react for 30 minutes at 37° C.

After the reaction, 100 μL of an internal standard solution (aqueous solution of cortisone acetate at 32 nmol/L) was immediately added thereto, subsequently the mixture was stirred with a vortex mixer, and the reaction was terminated. Then, 2 mL of ethyl acetate was added thereto, the mixture was stirred with a vortex mixer for 30 seconds, and the reaction product was extracted with ethyl acetate. After the extract was left to stand, the extract was separated into an aqueous layer and an ethyl acetate layer, and the ethyl acetate layer was collected. 750 μL of ethyl acetate was added to the aqueous layer, and the mixture was stirred and left to stand. Subsequently, an ethyl acetate layer was collected using a micropipette. This operation was performed two times, ethyl acetate thus collected was distilled off under reduced pressure, and the compound obtained after distillation was dissolved in MeOH. Thus, the amount of 6β-hydroxytestosterone was quantitatively determined by HPLC.

Meanwhile, the value of the enzyme activity that served as a reference for the enzyme activity retention ratio was calculated as follows. Cytochrome P450 that had been stored in a frozen state was thawed, and then was rapidly dissolved in a buffer for cytochrome P450 to prepare an enzyme solution having an enzyme concentration of 1.0 mg/mL. After the preparation, the solution was immediately added to the substrate solution as described above such that the amount of enzyme would be 1.0 μg, and an enzymatic reaction was induced thereby. Subsequently, the enzyme activity retention ratio was calculated based on the amount of 6β-hydroxytestosterone that had been quantitatively determined by HPLC, as a reference.

The results are presented in Table 32.

TABLE 32

Cytochrome P450: 3° C.

Biocatalyst solvent $$R_4-\overset{R_1}{\underset{R_3}{\overset{|}{N}}}-R_2\ X^-$$

| | Compound | $R_1$ | $R_2$ | $R_3$ | $R_4$ | $X^-$ | Enzyme concentration (mg/ml) | After 1 day | After 7 days | After 14 days |
|---|---|---|---|---|---|---|---|---|---|---|
| Example 3 | 3 | $(CH_2)_2OH$ | $(CH_2)_2OH$ | $(CH_2)_2OH$ | H | $CH_3COO^-$ | 1.0 | 43 | 10 | 7 |
| Example 4 | 4 | | | | | $CH_3CH(OH)COO^-$ | 1.0 | 50 | 25 | 20 |
| Example 5 | 5 | | | | | $HOOC(CH_2)_2COO^-$ | 1.0 | 53 | 36 | 20 |
| Example 6 | 6 | | | | | Citric acid | 1.0 | 41 | 24 | 13 |
| Example 10 | 10 | $HOCH_2-\underset{CH_2OH}{\overset{CH_2OH}{\overset{|}{C}}}-$ | H | H | H | $CH_3CH(OH)COO^-$ | 1.0 | 34 | 18 | 12 |
| Example 13 | 13 | | | | | $CH_3SO_3^-$ | 1.0 | 31 | 14 | 9 |
| Example 15 | 15 | $HOCH_2\underset{OH}{\overset{OH}{\overset{|}{C}H}}CH\underset{}{\overset{}{C}H}\underset{OH}{\overset{OH}{\overset{|}{C}H}}CH_2-$ | H | H | H | $CH_3CH(OH)COO^-$ | 1.0 | 28 | 20 | 15 |
| Example 18 | 18 | | | | | $CH_3-O-CH_2COO^-$ | 1.0 | 29 | 18 | 12 |
| Example 20 | 20 | $CH_3$ | $CH_3$ | $CH_3$ | $(CH_2)_2OH$ | $CH_3CH(OH)COO^-$ | 1.0 | 38 | 24 | 15 |
| Example 22 | 22 | $CH_3$ | $CH_3$ | $CH_3$ | $(CH_2)_2OH$ | $H_2PO_4^-$ | 1.0 | 48 | 36 | 20 |
| Comparative Example 2 | 29 | | BMI-BF$_4$ | | | | 1.0 | 45 | 12 | 6 |
| Comparative Example 9 | 36 | | Buffer | | | | 1.0 | 40 | 18 | 6 |
| Comparative Example 16 | 43 | | 20% glycerin solution | | | | 1.0 | 45 | 20 | 6 |

According to the results of storage at 3° C. (Table 32), in Comparative Examples (compounds 29, 36, and 43), the activity retention ratio decreased to 6% or lower after 14 days, while the compounds of the present invention (Examples 3 to 6, 10, 13, 15, 18, 20, and 22) exhibited activity retention ratios of 7% or higher after 14 days.

That is, it was suggested that even for cytochrome P450 that has particularly low stability compared to general enzymes and requires storage in a frozen state, the biocatalyst solvent of the present invention exhibits high retainability for the enzyme conformation.

4. −10° C. Preservation Test

Catalase was dissolved in the ionic liquids of the present invention (compounds 4, 10 and 15: Examples 28, 29, and 30) at a concentration of 50 mg/mL, and in aqueous solutions in which conventional stabilizers were dissolved (compounds 36 to 41: Comparative Examples 17 to 22) at a concentration of 20 mg/mL, and the solutions were left to stand for 24 hours in a low temperature thermostat set at −10° C. The ionic liquid solutions of the present invention retained liquidity, while the aqueous solutions of compounds 36 to 41 had frozen. Subsequently, the solutions were left to stand in a thermostat at 25° C. to raise the temperature (to melt the aqueous solutions of compounds 36 to 41), and the activity of catalase was measured as described above.

The results are presented in Table 33.

TABLE 33

Catalase: −10° C.

Biocatalyst solvent $$R_4-\overset{R_1}{\underset{R_3}{\overset{|}{N}}}-R_2\ X^-$$

| | Compound | $R_1$ | $R_2$ | $R_3$ | $R_4$ | $X^-$ | Aqueous solution concentration | Enzyme concentration (mg/mL) | Enzyme activity retention ratio (%) After 1 day Storage temperature | | |
|---|---|---|---|---|---|---|---|---|---|---|---|
| | | | | | | | | | −10° C. | 25° C. | 40° C. |
| Example 28 | 4 | $(CH_2)_2OH$ | $(CH_2)_2OH$ | $(CH_2)_2OH$ | H | $CH_3CH(OH)COO^-$ | — | 50 | 100 | 100 | 100 |

TABLE 33-continued

Catalase: −10° C.

| | Compound | Biocatalyst solvent $R_4-{}^+N(R_1)(R_2)(R_3)$ $X^-$ | | | | | Aqueous solution concentration | Enzyme concentration (mg/mL) | Enzyme activity retention ratio (%) After 1 day Storage temperature | | |
|---|---|---|---|---|---|---|---|---|---|---|---|
| | | $R_1$ | $R_2$ | $R_3$ | $R_4$ | $X^-$ | | | −10° C. | 25° C. | 40° C. |
| Example 29 | 10 | HOCH$_2$–C(CH$_2$OH)(CH$_2$OH)– | H | H | H | CH3CH(OH)COO$^-$ | — | 50 | 100 | 100 | 100 |
| Example 30 | 15 | HOCH$_2$CH(OH)CH(OH)CH(OH)CH(OH)CH$_2$– | H | H | H | CH$_3$CH(OH)COO$^-$ | — | 50 | 100 | 100 | 100 |
| Comparative Example 17 | 36 | Buffer | | | | | 10 mM | 20 | 87 | 100 | 100 |
| Comparative Example 18 | 37 | Aqueous solution of glycerin | | | | | 10 mg/mL | 20 | 68 | 100 | 100 |
| Comparative Example 19 | 38 | Aqueous solution of glucose | | | | | 10 mg/mL | 20 | 88 | 100 | 100 |
| Comparative Example 20 | 39 | Aqueous solution of bovine serum albumin | | | | | 10 mg/mL | 20 | 87 | 100 | 100 |
| Comparative Example 21 | 40 | Aqueous solution of lysine | | | | | 10 mg/mL | 20 | 13 | 100 | 100 |
| Comparative Example 22 | 41 | Aqueous solution of lysine and bovine serum albumin | | | | | 10 mg/mL | 20 | 0 | 100 | 100 |

When the catalase in the aqueous solutions of compounds 36 to 41, in which the activity was retained at 100% after one day at 25° C. and 40° C., was subjected to phase changes such as freezing at −10° C. and melting, the conformation of the enzyme changed, and the enzyme was deactivated. On the other hand, the compounds of the present invention 4, 10, and 15 were liquid at −10° C., and retained the activity at 100%. Thus, preservation was enabled. That is, regarding the preservation temperature, a lower temperature is generally preferred; however, as shown in Table 1, it was confirmed that the ionic liquids of the present invention have freezing points that are lower than −10° C., are liquid even at low temperature, have high preservability, and are highly convenient for use.

5. Low Concentration Preservation Test

Urease was dissolved in samples (compounds 4 to 6, 10, 18, 22, 23, 27, 29, 35 to 40, and 42) such that the concentrations would be 10 μg/mL or 10 ng/mL, and the solutions were left to stand in thermostats set at 25° C. and 40° C. After 180 days, the activity of urease was measured as described above.

The results are presented in Tables 34 to 37.

TABLE 34

10 μg urease: 25° C.

| | Compound | Biocatalyst solvent $R_4-{}^+N(R_1)(R_2)(R_3)$ $X^-$ | | | | | Aqueous solution concentration |
|---|---|---|---|---|---|---|---|
| | | $R_1$ | $R_2$ | $R_3$ | $R_4$ | $X^-$ | |
| Example 4 | 4 | (CH$_2$)$_2$OH | (CH$_2$)$_2$OH | (CH$_2$)$_2$OH | H | CH$_3$CH(OH)COO$^-$ | — |
| Example 5 | 5 | | | | | HOOC(CH$_2$)$_2$COO$^-$ | — |
| Example 6 | 6 | | | | | Citric acid | — |
| Example 10 | 10 | HOCH$_2$–C(CH$_2$OH)(CH$_2$OH)– | H | H | H | CH$_3$CH(OH)COO$^-$ | — |

TABLE 34-continued

10 μg urease: 25° C.

| | | $R_1$ | $R_2$ | $R_3$ | $R_4$ | $X^-$ | Aqueous solution concentration |
|---|---|---|---|---|---|---|---|
| Example 18 | 18 | HOCH$_2$CHCHCHCHCH$_2$— with OH, OH, OH, OH substituents | H | H | H | CH$_3$—O—CH$_2$COO$^-$ | — |
| Example 22 | 22 | CH$_3$ | CH$_3$ | CH$_3$ | (CH$_2$)$_2$OH | H$_2$PO$_4^-$ | — |
| Example 23 | 23 | CH$_3$ | CH$_3$ | C$_2$H$_5$ | (CH$_2$)$_2$OH | CH$_3$COO$^-$ | — |
| Example 27 | 27 | CH$_3$ | CH$_3$ | C$_2$H$_5$ | (CH$_2$)$_2$COOH | CH$_3$SO$_3^-$ | — |
| Comparative Example 2 | 29 | | | BMI-BF$_4$ | | | — |
| Comparative Example 8 | 35 | | | Glycerin | | | 100% |
| Comparative Example 9 | 36 | | | Buffer | | | 10 mM |
| Comparative Example 10 | 37 | | | Aqueous solution of glycerin | | | 10 mg/ml |
| Comparative Example 11 | 38 | | | Aqueous solution of glucose | | | 10 mg/ml |
| Comparative Example 12 | 39 | | | Aqueous solution of bovine serum albumin | | | 10 mg/ml |
| Comparative Example 13 | 40 | | | Aqueous solution of lysine | | | 10 mg/ml |
| Comparative Example 15 | 42 | | | Aqueous solution of arginine | | | 10 mg/ml |

| Enzyme | Enzyme concentration (μg/ml) | Enzyme activity retention ratio (%) Storage period | | | | | | | |
|---|---|---|---|---|---|---|---|---|---|
| | | After 1 day | After 7 days | After 14 days | After 21 days | After 30 days | After 60 days | After 90 days | After 180 days |
| Example 4 | 10 | 100 | 100 | 100 | 100 | 96 | 74 | 69 | 35 |
| Example 5 | 10 | 100 | 100 | 100 | 100 | 96 | 71 | 66 | 40 |
| Example 6 | 10 | 100 | 100 | 100 | 100 | 96 | 74 | 65 | 31 |
| Example 10 | 10 | 100 | 100 | 100 | 100 | 95 | 73 | 72 | 32 |
| Example 18 | 10 | 100 | 100 | 100 | 100 | 98 | 75 | 72 | 39 |
| Example 22 | 10 | 100 | 100 | 100 | 100 | 95 | 79 | 79 | 41 |
| Example 23 | 10 | 100 | 100 | 100 | 100 | 95 | 73 | 66 | 38 |
| Example 27 | 10 | 100 | 100 | 100 | 100 | 96 | 74 | 66 | 40 |
| Comparative Example 2 | 10 | 100 | 100 | 100 | 100 | 95 | 71 | 45 | 0 |
| Comparative Example 8 | 10 | 100 | 100 | 100 | 100 | 95 | 72 | 46 | 8 |
| Comparative Example 9 | 10 | 100 | 100 | 100 | 100 | 97 | 73 | 59 | 20 |
| Comparative Example 10 | 10 | 100 | 100 | 100 | 100 | 96 | 73 | 46 | 9 |
| Comparative Example 11 | 10 | 100 | 100 | 100 | 100 | 96 | 74 | 48 | 10 |
| Comparative Example 12 | 10 | 100 | 100 | 100 | 100 | 95 | 77 | 46 | 5 |
| Comparative Example 13 | 10 | 100 | 100 | 100 | 100 | 96 | 67 | 51 | 10 |
| Comparative Example 15 | 10 | 100 | 100 | 100 | 100 | 95 | 72 | 57 | 11 |

TABLE 35

10 μg urease: 40° C.

Biocatalyst solvent $$R_4 - \overset{R_1}{\underset{R_3}{\overset{|}{N^+}}} - R_2 \quad X^-$$

| | Compound | $R_1$ | $R_2$ | $R_3$ | $R_4$ | $X^-$ | Aqueous solution concentration |
|---|---|---|---|---|---|---|---|
| Example 4 | 4 | (CH$_2$)$_2$OH | (CH$_2$)$_2$OH | (CH$_2$)$_2$OH | H | CH$_3$CH(OH)COO$^-$ | — |
| Example 5 | 5 | | | | | HOOC(CH$_2$)$_2$COO$^-$ | — |
| Example 6 | 6 | | | | | Citric acid | — |

TABLE 35-continued

| | | | | | | | |
|---|---|---|---|---|---|---|---|
| | | 10 μg urease: 40° C. | | | | | |
| Example 10 | 10 | HOCH₂—C(CH₂OH)(CH₂OH)— | H | H | H | CH₃CH(OH)COO⁻ | — |
| Example 18 | 18 | HOCH₂CHCHCHCHCH₂— (with OH, OH, OH, OH) | H | H | H | CH₃—O—CH₂COO⁻ | — |
| Example 22 | 22 | CH₃ | CH₃ | CH₃ | (CH₂)₂OH | H₂PO₄⁻ | — |
| Example 23 | 23 | CH₃ | CH₃ | C₂H₅ | (CH₂)₂OH | CH₃COO⁻ | — |
| Example 27 | 27 | CH₃ | CH₃ | C₂H₅ | (CH₂)₂COOH | CH₃SO₃⁻ | — |
| Comparative Example 2 | 29 | | | BMI-BF₄ | | | — |
| Comparative Example 8 | 35 | | | Glycerin | | | 100% |
| Comparative Example 9 | 36 | | | Buffer | | | 10 mM |
| Comparative Example 10 | 37 | | | Aqueous solution of glycerin | | | 10 mg/ml |
| Comparative Example 11 | 38 | | | Aqueous solution of glucose | | | 10 mg/ml |
| Comparative Example 12 | 39 | | | Aqueous solution of bovine serum albumin | | | 10 mg/ml |
| Comparative Example 13 | 40 | | | Aqueous solution of lysine | | | 10 mg/ml |
| Comparative Example 15 | 42 | | | Aqueous solution of arginine | | | 10 mg/ml |

| | Enzyme concentration (μg/ml) | Enzyme activity retention ratio (%) Storage period | | | | | | | |
|---|---|---|---|---|---|---|---|---|---|
| | | After 1 day | After 7 days | After 14 days | After 21 days | After 30 days | After 60 days | After 90 days | After 180 days |
| Example 4 | 10 | 100 | 100 | 100 | 100 | 78 | 53 | 44 | 7 |
| Example 5 | 10 | 100 | 100 | 100 | 100 | 73 | 49 | 40 | 5 |
| Example 6 | 10 | 100 | 100 | 100 | 100 | 70 | 46 | 45 | 9 |
| Example 10 | 10 | 100 | 100 | 100 | 100 | 77 | 51 | 39 | 9 |
| Example 18 | 10 | 100 | 100 | 100 | 100 | 71 | 53 | 41 | 10 |
| Example 22 | 10 | 100 | 100 | 100 | 100 | 72 | 54 | 46 | 10 |
| Example 23 | 10 | 100 | 100 | 100 | 100 | 78 | 49 | 41 | 5 |
| Example 27 | 10 | 100 | 100 | 100 | 100 | 68 | 51 | 42 | 5 |
| Comparative Example 2 | 10 | 100 | 100 | 100 | 100 | 74 | 27 | 11 | 0 |
| Comparative Example 8 | 10 | 100 | 100 | 100 | 100 | 69 | 30 | 21 | 0 |
| Comparative Example 9 | 10 | 100 | 100 | 100 | 100 | 68 | 35 | 13 | 0 |
| Comparative Example 10 | 10 | 100 | 100 | 100 | 100 | 71 | 23 | 21 | 0 |
| Comparative Example 11 | 10 | 100 | 100 | 100 | 100 | 72 | 32 | 20 | 0 |
| Comparative Example 12 | 10 | 100 | 100 | 100 | 100 | 69 | 23 | 13 | 0 |
| Comparative Example 13 | 10 | 100 | 100 | 100 | 100 | 73 | 29 | 29 | 0 |
| Comparative Example 15 | 10 | 100 | 100 | 100 | 100 | 72 | 24 | 30 | 0 |

TABLE 36

10 ng urease: 25° C.

| | Compound | Biocatalyst solvent $R_4-{}^+N(R_1)(R_2)(R_3)\ X^-$ | | | | | Aqueous solution concentration |
|---|---|---|---|---|---|---|---|
| | | $R_1$ | $R_2$ | $R_3$ | $R_4$ | $X^-$ | |
| Example 4 | 4 | $(CH_2)_2OH$ | $(CH_2)_2OH$ | $(CH_2)_2OH$ | H | $CH_3CH(OH)COO^-$ | — |
| Example 5 | 5 | $(CH_2)_2OH$ | $(CH_2)_2OH$ | $(CH_2)_2OH$ | H | $HOOC(CH_2)_2COO^-$ | — |
| Example 6 | 6 | $(CH_2)_2OH$ | $(CH_2)_2OH$ | $(CH_2)_2OH$ | H | Citric acid | — |
| Example 10 | 10 | $HOCH_2-C(CH_2OH)(CH_2OH)-$ | H | H | H | $CH_3CH(OH)COO^-$ | — |
| Example 18 | 18 | $HOCH_2CH(OH)CH(OH)CH(OH)CH_2-$ | H | H | H | $CH_3-O-CH_2COO^-$ | — |
| Example 22 | 22 | $CH_3$ | $CH_3$ | $CH_3$ | $(CH_2)_2OH$ | $H_2PO_4^-$ | — |
| Example 23 | 23 | $CH_3$ | $CH_3$ | $C_2H_5$ | $(CH_2)_2OH$ | $CH_3COO^-$ | — |
| Example 27 | 27 | $CH_3$ | $CH_3$ | $C_2H_5$ | $(CH_2)_2COOH$ | $CH_3SO_3^-$ | — |
| Comparative Example 2 | 29 | BMI-$BF_4$ | | | | | — |
| Comparative Example 8 | 35 | Glycerin | | | | | 100% |
| Comparative Example 9 | 36 | Buffer | | | | | 10 mM |
| Comparative Example 10 | 37 | Aqueous solution of glycerin | | | | | 10 mg/ml |
| Comparative Example 11 | 38 | Aqueous solution of glucose | | | | | 10 mg/ml |
| Comparative Example 12 | 39 | Aqueous solution of bovine serum albumin | | | | | 10 mg/ml |
| Comparative Example 13 | 40 | Aqueous solution of lysine | | | | | 10 mg/ml |
| Comparative Example 15 | 42 | Aqueous solution of arginine | | | | | 10 mg/ml |

| | Enzyme concentration (ng/ml) | Enzyme activity retention ratio (%) Storage period | | | | | | | |
|---|---|---|---|---|---|---|---|---|---|
| | | After 1 day | After 7 days | After 14 days | After 21 days | After 30 days | After 60 days | After 90 days | After 180 days |
| Example 4 | 10 | 100 | 100 | 100 | 100 | 96 | 72 | 69 | 39 |
| Example 5 | 10 | 100 | 100 | 100 | 100 | 96 | 80 | 64 | 43 |
| Example 6 | 10 | 100 | 100 | 100 | 100 | 96 | 79 | 65 | 40 |
| Example 10 | 10 | 100 | 100 | 100 | 100 | 95 | 73 | 71 | 40 |
| Example 18 | 10 | 100 | 100 | 100 | 100 | 98 | 83 | 68 | 45 |
| Example 22 | 10 | 100 | 100 | 100 | 100 | 95 | 77 | 69 | 40 |
| Example 23 | 10 | 100 | 100 | 100 | 100 | 95 | 78 | 65 | 44 |
| Example 27 | 10 | 100 | 100 | 100 | 100 | 96 | 76 | 68 | 41 |
| Comparative Example 2 | 10 | 100 | 100 | 100 | 100 | 95 | 62 | 50 | 0 |
| Comparative Example 8 | 10 | 100 | 100 | 100 | 100 | 95 | 72 | 72 | 12 |
| Comparative Example 9 | 10 | 100 | 100 | 100 | 100 | 97 | 66 | 68 | 25 |
| Comparative Example 10 | 10 | 100 | 100 | 100 | 100 | 96 | 74 | 72 | 13 |
| Comparative Example 11 | 10 | 100 | 100 | 100 | 100 | 96 | 67 | 65 | 11 |
| Comparative Example 12 | 10 | 100 | 100 | 100 | 100 | 95 | 73 | 68 | 11 |
| Comparative Example 13 | 10 | 100 | 100 | 100 | 100 | 96 | 57 | 58 | 10 |

TABLE 36-continued

| | | 10 ng urease: 25° C. | | | | | | | |
|---|---|---|---|---|---|---|---|---|---|
| Comparative Example 15 | 10 | 100 | 100 | 100 | 100 | 95 | 65 | 59 | 10 |

TABLE 37

10 ng urease: 40° C.

| | Compound | Biocatalyst solvent $R_4-\overset{R_1}{\underset{R_3}{\overset{|}{N^+}}}-R_2 \; X^-$ | | | | | Aqueous solution concentration |
|---|---|---|---|---|---|---|---|
| | | $R_1$ | $R_2$ | $R_3$ | $R_4$ | $X^-$ | |
| Example 4 | 4 | $(CH_2)_2OH$ | $(CH_2)_2OH$ | $(CH_2)_2OH$ | H | $CH_3CH(OH)CO^-$ | — |
| Example 5 | 5 | | | | | $HOOC(CH_2)_2CO^-$ | — |
| Example 6 | 6 | | | | | Citric acid | — |
| Example 10 | 10 | $HOCH_2-\overset{CH_2OH}{\underset{CH_2OH}{\overset{|}{C}}}-$ | H | H | H | $CH_3CH(OH)COO^-$ | — |
| Example 18 | 18 | $HOCH_2CHCHCHCH_2-$ with OH OH OH OH | H | H | H | $CH_3-O-CH_2COO^-$ | — |
| Example 22 | 22 | $CH_3$ | $CH_3$ | $CH_3$ | $(CH_2)_2OH$ | $H_2PO_4^-$ | — |
| Example 23 | 23 | $CH_3$ | $CH_3$ | $C_2H_5$ | $(CH_2)_2OH$ | $CH_3COO^-$ | — |
| Example 27 | 27 | $CH_3$ | $CH_3$ | $C_2H_5$ | $(CH_2)_2COOH$ | $CH_3SO_3^-$ | — |
| Comparative Example 2 | 29 | BMI-BF$_4$ | | | | | — |
| Comparative Example 8 | 35 | Glycerin | | | | | 100% |
| Comparative Example 9 | 36 | Buffer | | | | | 10 mM |
| Comparative Example 10 | 37 | Aqueous solution of glycerin | | | | | 10 mg/ml |
| Comparative Example 11 | 38 | Aqueous solution of glucose | | | | | 10 mg/ml |
| Comparative Example 12 | 39 | Aqueous solution of bovine serum albumin | | | | | 10 mg/ml |
| Comparative Example 13 | 40 | Aqueous solution of lysine | | | | | 10 mg/ml |
| Comparative Example 15 | 42 | Aqueous solution of arginine | | | | | 10 mg/ml |

| Enzyme | Enzyme concentration (ng/ml) | Enzyme activity retention ratio (%) Storage period | | | | | | | |
|---|---|---|---|---|---|---|---|---|---|
| | | After 1 day | After 7 days | After 14 days | After 21 days | After 30 days | After 60 days | After 90 days | After 180 days |
| Example 4 | 10 | 100 | 100 | 100 | 100 | 78 | 63 | 50 | 10 |
| Example 5 | 10 | 100 | 100 | 100 | 100 | 73 | 61 | 49 | 10 |
| Example 6 | 10 | 100 | 100 | 100 | 100 | 70 | 69 | 50 | 9 |
| Example 10 | 10 | 100 | 100 | 100 | 100 | 77 | 65 | 49 | 11 |
| Example 18 | 10 | 100 | 100 | 100 | 100 | 71 | 64 | 52 | 10 |
| Example 22 | 10 | 100 | 100 | 100 | 100 | 72 | 67 | 52 | 12 |
| Example 23 | 10 | 100 | 100 | 100 | 100 | 78 | 65 | 52 | 11 |
| Example 27 | 10 | 100 | 100 | 100 | 100 | 68 | 68 | 52 | 8 |
| Comparative Example 2 | 10 | 100 | 100 | 100 | 100 | 74 | 45 | 14 | 0 |
| Comparative Example 8 | 10 | 100 | 100 | 100 | 100 | 69 | 43 | 27 | 0 |
| Comparative Example 9 | 10 | 100 | 100 | 100 | 100 | 68 | 47 | 22 | 0 |

TABLE 37-continued

| | | 10 ng urease: 40° C. | | | | | | | |
|---|---|---|---|---|---|---|---|---|---|
| | Comparative Example 10 | 10 | 100 | 100 | 100 | 100 | 71 | 42 | 20 | 0 |
| | Comparative Example 11 | 10 | 100 | 100 | 100 | 100 | 72 | 45 | 26 | 0 |
| | Comparative Example 12 | 10 | 100 | 100 | 100 | 100 | 69 | 49 | 21 | 0 |
| | Comparative Example 13 | 10 | 100 | 100 | 100 | 100 | 73 | 42 | 25 | 0 |
| | Comparative Example 15 | 10 | 100 | 100 | 100 | 100 | 72 | 44 | 30 | 0 |

According to the results of 10 μg/mL (Tables 34 and 35), in Comparative Examples (compounds 29, 35 to 40, and 42), the activity retention ratio decreased to 20% or lower at 25° C., and to 0% at 40° C., after 180 days. In contrast, the compounds of the present invention (Examples 4 to 6, 10, 18, 22, 23, and 27) exhibited activity retention ratios of 31% or higher at 25° C. and 5% or higher at 40° C. after 180 days. Furthermore, according to the results of 10 ng/mL (Tables 36 and 37), in Comparative Examples (compounds 29, 35 to 40, and 42), the activity retention ratios decreased to 25% or lower at 25° C. and to 0% at 40° C. after 180 days. In contrast, the compounds of the present invention (Examples 4 to 6, 10, 18, 22, 23, and 27) exhibited activity retention ratios of 39% or higher at 25° C. and 8% or higher at 40° C. after 180 days. That is, it was suggested that even if the preservation concentration of a biocatalyst is a very low concentration, the biocatalyst solvents of the present invention retain the enzyme activity, and have high retainability for enzyme conformations.

6. Anhydrous Ionic Liquid Preservability Test

A preservability test for urease in anhydrous ionic liquids was performed as follows. First, samples (compounds 1 to 6, 8 to 11, 13, 15, 18, 20, 23, 24, 27, 29, and 33 to 35) were each introduced into a screw tube and dehydrated under reduced pressure. Thus, anhydrous ionic liquids were produced. Urease was added thereto and dissolved therein to obtain the set concentrations described in Tables 38 and 39. Subsequently, the interior of each of the screw tubes was purged with nitrogen so as to prevent moisture from entering into the screw tubes, and the screw tubes were tightly sealed. Then, the screw tubes were left to stand in thermostats set at 25° C. and 40° C., and the activity of urease was measured by a method similar to that described above.

The results are presented in Tables 38 and 39.

TABLE 38

Anhydrous ionic liquid urease: 25° C.

| | | Biocatalyst solvent $R_4 - {}^+N(R_1)(R_2)(R_3)\ X^-$ | | | | | Aqueous solution |
|---|---|---|---|---|---|---|---|
| | Compound | $R_1$ | $R_2$ | $R_3$ | $R_4$ | $X^-$ | concentration |
| Example 1 | 1 | (CH2)$_2$OH | H | H | H | CH$_3$CH(OH)COO$^-$ | — |
| Example 2 | 2 | (CH2)$_2$OH | (CH$_2$)$_2$OH | H | H | CH$_3$CH(OH)COO$^-$ | — |
| Example 3 | 3 | (CH2)$_2$OH | (CH$_2$)$_2$OH | (CH$_2$)$_2$OH | H | CH$_3$COO$^-$ | — |
| Example 4 | 4 | | | | | CH$_3$CH(OH)COO$^-$ | — |
| Example 5 | 5 | | | | | HOOC(CH$_2$)$_2$COO$^-$ | — |
| Example 6 | 6 | | | | | Citric acid | — |
| Example 8 | 8 | 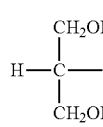 | H | H | H | CH$_3$CH(OH)COO$^-$ | — |
| Example 9 | 9 | 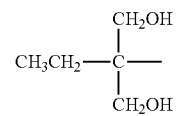 | H | H | H | CH$_3$CH(OH)COO$^-$ | — |
| Example 10 | 10 | 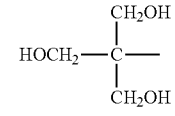 | H | H | H | CH$_3$CH(OH)COO$^-$ | — |
| Example 11 | 11 | | | | | Citric acid | — |
| Example 13 | 13 | | | | | CH$_3$SO$_3^-$ | — |

TABLE 38-continued

Anhydrous ionic liquid urease: 25° C.

| | Compound | R₁ | R₂ | R₃ | R₄ | X⁻ | Aqueous solution concentration |
|---|---|---|---|---|---|---|---|
| Example 15 | 15 | OH  OH<br>HOCH₂CHCHCHCHCH₂—<br>OH  OH | H | H | H | CH₃CH(OH)COO⁻ | — |
| Example 18 | 18 | | | | | CH₃—O—CH₂COO⁻ | — |
| Example 20 | 20 | CH₃ | CH₃ | CH₃ | (CH₂)₂OH | CH₃CH(OH)COO⁻ | — |
| Example 23 | 23 | CH₃ | CH₃ | C₂H₅ | (CH₂)₂OH | CH₃COO⁻ | — |
| Example 24 | 24 | | | | | CH3CH(OH)COO⁻ | — |
| Example 27 | 27 | CH₃ | CH₃ | C₂H₅ | (CH₂)₂COOH | CH₃SO₃⁻ | — |
| Comparative Example 2 | 29 | | | BMI-BF₄ | | | — |
| Comparative Example 6 | 33 | | | HOPMI-PF₆ | | | — |
| Comparative Example 7 | 34 | | | DHOPMI-PF₆ | | | — |
| Comparative Example 8 | 35 | | | Glycerin | | | 100% |

| | Enzyme concentration (mg/ml) | Enzyme activity retention ratio (%) Storage period | | | | |
|---|---|---|---|---|---|---|
| | | After 1 day | After 7 days | After 14 days | After 21 days | After 30 days |
| Example 1 | 35.0 | 98 | 98 | 96 | 95 | 95 |
| Example 2 | 35.0 | 99 | 98 | 95 | 94 | 94 |
| Example 3 | 20.0 | 98 | 97 | 95 | 93 | 93 |
| Example 4 | 40.0 | 99 | 98 | 97 | 96 | 95 |
| Example 5 | 30.0 | 98 | 97 | 95 | 93 | 93 |
| Example 6 | 30.0 | 98 | 97 | 95 | 93 | 92 |
| Example 8 | 40.0 | 99 | 96 | 96 | 96 | 95 |
| Example 9 | 40.0 | 99 | 96 | 96 | 96 | 96 |
| Example 10 | 40.0 | 98 | 98 | 95 | 95 | 95 |
| Example 11 | 30.0 | 98 | 98 | 96 | 95 | 94 |
| Example 13 | 20.0 | 97 | 95 | 93 | 93 | 90 |
| Example 15 | 40.0 | 97 | 95 | 95 | 93 | 90 |
| Example 18 | 30.0 | 98 | 96 | 95 | 93 | 89 |
| Example 20 | 30.0 | 99 | 96 | 94 | 94 | 94 |
| Example 23 | 10.0 | 99 | 97 | 96 | 93 | 92 |
| Example 24 | 30.0 | 99 | 96 | 96 | 93 | 92 |
| Example 27 | 10.0 | 97 | 93 | 90 | 90 | 90 |
| Comparative Example 2 | 1.0 | 65 | 45 | 18 | 8 | 0 |
| Comparative Example 6 | 10.0 | 81 | 70 | 58 | 21 | 0 |
| Comparative Example 7 | 10.0 | 85 | 73 | 62 | 25 | 0 |
| Comparative Example 8 | 10.0 | 98 | 90 | 81 | 49 | 20 |

TABLE 39

Anhydrous ionic liquid urease: 40° C.

Biocatalyst solvent $$R_4\text{—}{}^+\!N\text{—}R_2 \ X^-$$
with $R_1$ above and $R_3$ below N

| | Compound | R₁ | R₂ | R₃ | R₄ | X⁻ | Aqueous solution concentration |
|---|---|---|---|---|---|---|---|
| Example 1 | 1 | (CH₂)₂OH | H | H | H | CH₃CH(OH)COO⁻ | — |
| Example 2 | 2 | (CH₂)₂OH | (CH₂)₂OH | H | H | CH₃CH(OH)COO⁻ | — |
| Example 3 | 3 | (CH₂)₂OH | (CH₂)₂OH | (CH₂)₂OH | H | CH₃COO⁻ | — |
| Example 4 | 4 | | | | | CH₃CH(OH)COO⁻ | — |
| Example 5 | 5 | | | | | HOOC(CH₂)₂COO⁻ | — |
| Example 6 | 6 | | | | | Citric acid | — |

TABLE 39-continued

Anhydrous ionic liquid urease: 40° C.

| | | | | | | | |
|---|---|---|---|---|---|---|---|
| Example 8 | 8 | H—C(CH₂OH)(CH₂OH)—CH₂OH | H | H | H | CH₃CH(OH)COO⁻ | — |
| Example 9 | 9 | CH₃CH₂—C(CH₂OH)(CH₂OH)— | H | H | H | CH₃CH(OH)COO⁻ | — |
| Example 10 | 10 | HOCH₂—C(CH₂OH)(CH₂OH)— | H | H | H | CH₃CH(OH)COO⁻ | — |
| Example 11 | 11 | | | | | Citric acid | — |
| Example 13 | 13 | | | | | CH₃SO₃⁻ | — |
| Example 15 | 15 | HOCH₂CHCHCHCHCH₂— (OH OH OH OH) | H | H | H | CH₃CH(OH)COO⁻ | — |
| Example 18 | 18 | | | | | CH₃—O—CH₂COO⁻ | — |
| Example 20 | 20 | CH₃ | CH₃ | CH₃ | (CH₂)₂OH | CH₃CH(OH)COO⁻ | — |
| Example 23 | 23 | CH₃ | CH₃ | C₂H₅ | (CH₂)₂OH | CH₃COO⁻ | — |
| Example 24 | 24 | | | | | CH₃CH(OH)COO⁻ | — |
| Example 27 | 27 | CH₃ | CH₃ | C₂H₅ | (CH₂)₂COOH | CH₃SO₃⁻ | — |
| Comparative Example 2 | 29 | | | BMI-BF₄ | | | — |
| Comparative Example 6 | 33 | | | HOPMI-PF₆ | | | — |
| Comparative Example 7 | 34 | | | DHOPMI-PF₆ | | | — |
| Comparative Example 8 | 35 | | | Glycerin | | | 100% |

| | Enzyme concentration (mg/ml) | Enzyme activity retention ratio (%) Storage period | | | | |
|---|---|---|---|---|---|---|
| | | After 1 day | After 7 days | After 14 days | After 21 days | After 30 days |
| Example 1 | 35.0 | 94 | 91 | 85 | 75 | 70 |
| Example 2 | 35.0 | 94 | 90 | 80 | 75 | 69 |
| Example 3 | 20.0 | 92 | 89 | 75 | 73 | 68 |
| Example 4 | 40.0 | 95 | 93 | 80 | 78 | 70 |
| Example 5 | 30.0 | 95 | 92 | 80 | 80 | 73 |
| Example 6 | 30.0 | 94 | 92 | 81 | 80 | 72 |
| Example 8 | 40.0 | 95 | 91 | 78 | 75 | 75 |
| Example 9 | 40.0 | 95 | 91 | 77 | 75 | 75 |
| Example 10 | 40.0 | 95 | 80 | 78 | 75 | 74 |
| Example 11 | 30.0 | 94 | 92 | 84 | 80 | 69 |
| Example 13 | 20.0 | 92 | 88 | 77 | 70 | 70 |
| Example 15 | 40.0 | 94 | 90 | 82 | 80 | 73 |
| Example 18 | 30.0 | 93 | 90 | 82 | 80 | 70 |
| Example 20 | 30.0 | 94 | 89 | 83 | 83 | 75 |
| Example 23 | 10.0 | 92 | 88 | 79 | 70 | 68 |
| Example 24 | 30.0 | 91 | 90 | 75 | 71 | 65 |
| Example 27 | 10.0 | 93 | 88 | 74 | 70 | 63 |
| Comparative Example 2 | 1.0 | 58 | 30 | 15 | 0 | 0 |
| Comparative Example 6 | 10.0 | 51 | 35 | 20 | 10 | 0 |
| Comparative Example 7 | 10.0 | 55 | 42 | 25 | 15 | 0 |
| Comparative Example 8 | 10.0 | 89 | 77 | 20 | 15 | 10 |

According to the results obtained at 25° C. (Table 38), in Comparative Examples (compounds 29 and 33 to 35), the activity retention ratios decreased to 20% or lower after 30 days, while the compounds of the present invention (Examples 1 to 6, 8 to 11, 13, 15, 18, 20, 23, 24, and 27) exhibited activity retention ratios of 89% or higher after 30 days. Furthermore, according to the results obtained at 40° C. (Table 39), in Comparative Examples (compounds 29 and 33 to 35), the activity retention ratios decreased to 10% or lower after 30 days, while the compounds of the present invention (Examples 1 to 6, 8 to 11, 13, 15, 18, 20, 23, 24, and 27) exhibited activity retention ratios of 63% or higher after 30 days. That is, it was suggested that even as anhydrous ionic liquids that do not contain water, the biocatalyst solvents of the present invention retain the activity of enzymes, and have high retainability for enzyme conformations.

Furthermore, when a comparison was made between the results obtained with urease that had been Fed in hydrous ionic liquids in Tables 4 to 9, and the results obtained with anhydrous ionic liquids in Tables 38 and 39, it was suggested that since the activity retention ratios were relatively equal, the effect of retaining enzyme activity is not related to the presence of water, and is attributable to the structure of the ionic liquids.

On the other hand, it was confirmed from the results of 4. −10° C. preservation test that phase change of ionic liquids (from solid to liquid) deactivates enzyme activity. However, depending on the applications of the ionic liquids as biocatalyst solvents, utilization thereof not only in the form of a hydrous substance but also in the form of an anhydride can be conceived, and in that case, it is contemplated that an ionic liquid that does not undergo phase changes and is liquid as an anhydride, is desirable.

The invention claimed is:

1. A method for stabilizing enzyme activity during storage in a solvent comprising:
preparing an enzyme solution in which an activity of the enzyme is retained, said solution comprising the solvent and the enzyme, wherein the solvent consists of an ionic liquid including a quaternary ammonium cation represented by the following Formula (I) and an anion:

[Chemical Formula 1]

$$N^+[R^a]_n[R^b]_{4-n} \qquad (I)$$

wherein $R^a$'s each independently represent a hydroxyalkyl group having one or more hydroxyl groups and a linear or branched alkyl moiety having 1 to 10 carbon atoms, the alkyl moiety optionally containing an oxygen atom; a carboxyalkyl group having one or more carboxyl groups and a linear or branched alkyl moiety having 1 to 10 carbon atoms, the alkyl moiety optionally containing an oxygen atom; or a hydroxycarboxyalkyl group having one or more hydroxyl groups, one or more carboxyl groups and a linear or branched alkyl moiety having 1 to 10 carbon atoms, the alkyl moiety optionally containing an oxygen atom; $R^b$'s each independently represent a hydrogen atom, or a linear or branched alkyl group having 1 to 5 carbon atoms; and n represents an integer from 1 to 4;
storing the enzyme solution for a period of time after preparing; and
subjecting the stored enzyme solution to a biochemical reaction to which the enzyme has substrate specificity, wherein the solvent enhances the retention of the enzyme activity during said storage.

2. The method according to claim 1, wherein each $R^b$ independently represents a hydrogen atom, a methyl group or an ethyl group.

3. The method according to claim 2, wherein each $R^b$ represents a hydrogen atom.

4. The method according to claim 2, wherein the quaternary ammonium cation represented by Formula (I) in the ionic liquid has a structure wherein n is 1 to 3.

5. The method according to claim 3, wherein the quaternary ammonium cation represented by Formula (I) in the ionic liquid has a structure wherein n is 1 to 3.

6. The method according to claim 1, wherein the anion of the ionic liquid is at least one selected from the group consisting of a halogen-based anion, a sulfur-based anion, a phosphorous-based anion, a cyan-based anion, a boron-based anion, a fluorine-based anion, a nitrogen oxide-based anion and a carboxylate anion.

7. The method according to claim 6, wherein the anion of the ionic liquid is at least one selected from the group consisting of a carboxylate anion, a sulfonate anion and a phosphate anion.

* * * * *